United States Patent
Demeule et al.

(10) Patent No.: US 9,487,589 B2
(45) Date of Patent: Nov. 8, 2016

(54) ANTI-C-MET-ANTIBODY FORMULATIONS

(71) Applicant: Genentech, Inc., South San Francisco, CA (US)

(72) Inventors: Barthelemy Demeule, San Mateo, CA (US); Bruce Kabakoff, Pacifica, CA (US); Jun Liu, South San Francisco, CA (US); Nicole Piros, San Francisco, CA (US); Qing Zhu, San Jose, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/534,085

(22) Filed: Nov. 5, 2014

(65) Prior Publication Data

US 2015/0064191 A1 Mar. 5, 2015

Related U.S. Application Data

(63) Continuation of application No. 13/538,901, filed on Jun. 29, 2012, now abandoned.

(60) Provisional application No. 61/503,513, filed on Jun. 30, 2011.

(51) Int. Cl.
*A61K 39/395* (2006.01)
*C07K 16/28* (2006.01)
*C07K 16/40* (2006.01)

(52) U.S. Cl.
CPC ..... *C07K 16/2863* (2013.01); *A61K 39/39591* (2013.01); *C07K 16/40* (2013.01); *C07K 2317/52* (2013.01); *C07K 2317/522* (2013.01); *C07K 2317/56* (2013.01); *C07K 2317/76* (2013.01)

(58) Field of Classification Search
CPC ............. C07K 16/00–16/468; C07K 16/2863; A61K 39/395–39/39591
See application file for complete search history.

(56) References Cited

U.S. PATENT DOCUMENTS

| | | | |
|---|---|---|---|
| 4,342,566 A | 8/1982 | Theofilopoulos et al. |
| 4,816,567 A | 3/1989 | Cabilly et al. |
| 5,169,939 A | 12/1992 | Gefter et al. |
| 5,227,158 A | 7/1993 | Jardieu |
| 5,264,365 A | 11/1993 | Georgiou et al. |
| 5,316,921 A | 5/1994 | Godowski et al. |
| 5,328,837 A | 7/1994 | Godowski et al. |
| 5,362,716 A | 11/1994 | Kmiecik et al. |
| 5,500,362 A | 3/1996 | Robinson et al. |
| 5,508,192 A | 4/1996 | Georgiou et al. |
| 5,547,856 A | 8/1996 | Godowski et al. |
| 5,624,821 A | 4/1997 | Winter et al. |
| 5,646,036 A | 7/1997 | Schwall et al. |
| 5,648,237 A | 7/1997 | Carter et al. |
| 5,648,260 A | 7/1997 | Winter et al. |
| 5,686,292 A | 11/1997 | Schwall et al. |
| 5,731,168 A | 3/1998 | Carter et al. |
| 5,789,199 A | 8/1998 | Joly et al. |
| 5,807,706 A | 9/1998 | Carter et al. |
| 5,821,333 A | 10/1998 | Carter et al. |
| 5,821,337 A | 10/1998 | Carter et al. |
| 5,840,523 A | 11/1998 | Simmons et al. |
| 5,859,205 A | 1/1999 | Adair et al. |
| 5,871,959 A | 2/1999 | Rong et al. |
| 5,968,509 A | 10/1999 | Gorman et al. |
| 6,027,888 A | 2/2000 | Georgiou et al. |
| 6,083,715 A | 7/2000 | Georgiou et al. |
| 6,121,022 A | 9/2000 | Presta et al. |
| 6,165,745 A | 12/2000 | Ward et al. |
| 6,171,586 B1 | 1/2001 | Lam et al. |
| 6,207,152 B1 | 3/2001 | Schwall et al. |
| 6,214,344 B1 | 4/2001 | Schwall et al. |
| 6,267,958 B1 | 7/2001 | Andya et al. |
| 6,331,415 B1 | 12/2001 | Cabilly et al. |
| 6,468,529 B1 | 10/2002 | Schwall et al. |
| 6,685,940 B2 | 2/2004 | Andya et al. |
| 7,476,724 B2 | 1/2009 | Dennis et al. |
| 7,615,529 B2 | 11/2009 | Kong-Beltran et al. |
| 7,892,550 B2 | 2/2011 | Dennis et al. |
| 7,951,368 B2 | 5/2011 | Li et al. |
| 8,372,396 B2 | 2/2013 | Andya et al. |
| 8,536,118 B2 | 9/2013 | Kong-Beltran et al. |
| 2002/0055537 A1 | 5/2002 | Gerlach et al. |
| 2004/0208876 A1 | 10/2004 | Kim et al. |
| 2005/0019327 A1 | 1/2005 | Kim et al. |
| 2005/0054019 A1 | 3/2005 | Michaud et al. |
| 2005/0186208 A1 | 8/2005 | Fyfe et al. |
| 2005/0227324 A1 | 10/2005 | Huang et al. |
| 2006/0088523 A1 | 4/2006 | Andya et al. |
| 2006/0216288 A1 | 9/2006 | Chang |
| 2008/0063641 A1 | 3/2008 | Huang et al. |
| 2009/0155807 A1 | 6/2009 | Yauch |

(Continued)

FOREIGN PATENT DOCUMENTS

CN 1612689 A 5/2005
EP 0131424 B1 9/1989

(Continued)

OTHER PUBLICATIONS

Kerwin BA, J. Pharm. Sci. 2008; 97(8): 2924-35.*
Daugherty & Mrsny, Adv Drug Del Rev. 2006; 58:686-706.*
Afanasieva et al., "Single-chain antibody and its derivatives directed against vascular endothelial growth factor: application for antiangiogenic gene therapy" Gene Ther 10(21):1850-1859 (2003).
Amler et al., "Exploratory biomark analyses from a placebo-controlled phase II study of (OAM4558g) of MetMAb in combination with erlotinib in patients with advanced non-small-cell lung cancer (NSCLC)" Slides World Conference on Lung Cancer—14th, (Jul. 3, 2011).
Angeloni et al., "The soluble sema domain of the RON receptor inhibits macrophage-stimulating protein-induced receptor activation" J Biol Chem. 279(5):3726-32.

(Continued)

*Primary Examiner* — Jessica H Roark
(74) *Attorney, Agent, or Firm* — Morrison & Foerster LLP

(57) ABSTRACT

Provided herein are pharmaceutical formulations comprising a one-armed, anti-c-met antibody and uses of the same.

20 Claims, 5 Drawing Sheets

(56) References Cited

U.S. PATENT DOCUMENTS

| | | |
|---|---|---|
| 2009/0226443 A1 | 9/2009 | Filvaroff et al. |
| 2009/0226455 A1 | 9/2009 | Filvaroff |
| 2010/0015157 A1 | 1/2010 | Andya et al. |
| 2010/0016241 A1 | 1/2010 | Kong-Beltran et al. |
| 2010/0028337 A1 | 2/2010 | Kong-Beltran et al. |
| 2011/0008337 A1 | 1/2011 | Curd et al. |
| 2011/0200596 A1 | 8/2011 | Huang et al. |
| 2011/0262436 A1 | 10/2011 | Bender et al. |
| 2011/0287003 A1* | 11/2011 | Patel ............... A61K 31/337 424/133.1 |
| 2011/0300146 A1 | 12/2011 | Dennis et al. |
| 2012/0082662 A1 | 4/2012 | Dennis et al. |
| 2012/0082663 A1 | 4/2012 | Dennis et al. |
| 2012/0089541 A1 | 4/2012 | Patel et al. |
| 2012/0171210 A1 | 7/2012 | Kong-Beltran et al. |
| 2013/0004484 A1 | 1/2013 | Demeule et al. |
| 2013/0071384 A1 | 3/2013 | Andya et al. |
| 2013/0129718 A1 | 5/2013 | Wong et al. |

FOREIGN PATENT DOCUMENTS

| | | |
|---|---|---|
| EP | 0567585 B1 | 11/1993 |
| EP | 1802344 B1 | 8/2012 |
| WO | WO-92/05184 A1 | 4/1992 |
| WO | WO-92/13097 A1 | 8/1992 |
| WO | WO-92/20792 A1 | 11/1992 |
| WO | WO-93/15754 A1 | 8/1993 |
| WO | WO-93/23541 A1 | 11/1993 |
| WO | WO-93/23550 A2 | 11/1993 |
| WO | WO-93/23550 A3 | 11/1993 |
| WO | WO-94/04679 A1 | 3/1994 |
| WO | WO-94/06909 A2 | 3/1994 |
| WO | WO-94/06909 A3 | 3/1994 |
| WO | WO-94/29348 A2 | 12/1994 |
| WO | WO-94/29351 A2 | 12/1994 |
| WO | WO-94/29351 A3 | 12/1994 |
| WO | WO-95/01376 A1 | 1/1995 |
| WO | WO-96/27011 A1 | 9/1996 |
| WO | WO-96/33980 A1 | 10/1996 |
| WO | WO-96/38557 A1 | 12/1996 |
| WO | WO-98/45331 A2 | 10/1998 |
| WO | WO-98/45331 A3 | 10/1998 |
| WO | WO-99/01556 A2 | 1/1999 |
| WO | WO-99/01556 A3 | 1/1999 |
| WO | WO-99/51642 A1 | 10/1999 |
| WO | WO-00/29584 A1 | 5/2000 |
| WO | WO-01/45746 A2 | 6/2001 |
| WO | WO-01/45746 A3 | 6/2001 |
| WO | WO-02/11677 A2 | 2/2002 |
| WO | WO-02/11677 A3 | 2/2002 |
| WO | WO-03/039485 A2 | 5/2003 |
| WO | WO-03/039485 A3 | 5/2003 |
| WO | WO-2004/016769 A2 | 2/2004 |
| WO | WO-2004/016769 A3 | 2/2004 |
| WO | WO-2004/058820 A2 | 7/2004 |
| WO | WO-2004/058820 A3 | 7/2004 |
| WO | WO-2004/072117 A2 | 8/2004 |
| WO | WO-2004/072117 A3 | 8/2004 |
| WO | WO-2005/016382 A1 | 2/2005 |
| WO | WO-2005/063816 A2 | 7/2005 |
| WO | WO-2005/063816 A3 | 7/2005 |
| WO | WO-2006/015371 A2 | 2/2006 |
| WO | WO-2006/015371 A3 | 2/2006 |
| WO | WO-2006/044908 A3 | 4/2006 |
| WO | WO-2007/063816 A1 | 6/2007 |
| WO | WO-2007/066185 A2 | 6/2007 |
| WO | WO-2007/066185 A3 | 6/2007 |
| WO | WO-2007/106503 A2 | 9/2007 |
| WO | WO-2007/106503 A3 | 9/2007 |
| WO | WO-2010/004345 A1 | 1/2010 |
| WO | WO2010/045345 A2 * | 4/2010 |
| WO | WO-2011/143665 A1 | 11/2011 |
| WO | WO-2012/031027 A1 | 3/2012 |
| WO | WO-2006/044908 A2 | 4/2016 |

OTHER PUBLICATIONS

Antibodies, A laboratory manual, Cold Spring Harbor Laboratory, Harlow and Lane pp. 28 (1988).

Antipenko et al., "Structure of the Semaphorin-3A Receptor Binding Module" Neuron 39:589-598 (Aug. 14, 2003).

Arie et al., "Chaperone function of FkpA, a heat shock prolyl isomerase, in the periplasm of *Escherichia coli*" Mol Microbiol 39(1):199-210(2001).

Asami et al., "Purification and Characterization of Hepatocyte Growth Factor from Injured Liver of Carbon Tetrachloride-Treated Rats" J Biol Chem 109(1):8-13 (Jan. 1991).

Atwell et al., "Stable heterodimers from remodeling the domain interface of a homodimer using a phage display library" J. Mol. Biol. 270(1):26-35 (1997).

Baca et al., "Antibody humanization using monovalent phage display" J Biol Chem 1272(16):10678-10684 (1997).

Bai et al., "Population pharmacokinetic analysis from phase I and phase II studies of the American monovalent antibody MetMAb in patients with advanced solid tumors" Poster Society of Clinical Oncology 47th Annual Meeting (ASCO 2011), (Jun. 3, 2011).

Bai et al., "Population pharmacokinetic analysis from phase I and phase II studies of the humanized monovalent antibody MetMAb in patients with advanced solid tumors" Abstract American Society of Clinical Oncology 47th Annual Meeting (ASCO 2011), (Jun. 3, 2011).

Barbas et al., "In Vitro Evolution of a Neutralizing Human Antibody to Human Immunodeficiency Virus Type 1 to Enhance Affinity and Broaden Strain Cross-Reactivity" Natl Acad Sci USA 91(9):3809-3813 (Apr. 1994).

Bardelli et al., "Gab 1 Coupling to the HGF/Met Receptor Multifunctional Docking Site Requires Binding of Grb2 and Correlates with the Transforming Potential" Oncogene 15:3103-3111 ( 1997).

Bean et al. et al., "MET amplification occurs with or without T790M mutations in EGFR mutant lung tumors with acquired resistance to gefitinib or erlotinib" P Natl Acad Sci USA 104(52):20932-7 (Dec. 2007).

Bellusci et al., Creation of an hepatocyte growth factor/scatter factor autocrine loop in carcinoma cells induces invasive properties associated with increased tumorigenicity Oncogene 9(4):1091-9 (1994).

Bendell et al., "A randomized, phase II, multicenter, double-blind, placebo-controlled study evaluating onartuzumab (MetMAb) in combination with mFOLFOX6 plus bevacizumab in patients with metastatic colorectal cancer" Abstract 48th ASCO, (2012).

Bengtsson et al., "18F-FDG PET as a surrogate biomarker in non-small cell lung cancer treated with erlotinib: newly identified lesions are more informative than standardized uptake value" The Journal of Nuclear Medicine 53(4):530 (2012).

Bengtsson et al., "New lesion (NL) status by FDG PET is a strong predictor of survival duration (OS) in second- and third-line non-small-cell lung cancer (NSCLC) patients treated with erlotinib and Met MAb+erlotinib" Slides 14$^{th}$ WCLC, (2011).

Bertotti et al., "Tyrosine Kinase Signal Specificity: Lessons from the HGF Receptor" Trends Biochem Sci 28(10):527-533 (Oct. 2003).

Birchrneier et al., "Met, Metastasis, Motility and More" Nat Rev Mol Cell Bio 4:915-925 (Dec. 2003).

Bladt et al., "Essential Role for the C-met Receptor in the Migration of Myogenic Precursor Cells into the Limb Bud" Nature 376:768-771 (Aug. 31, 1995).

Blechman et al., "The Fourth Immunoglobulin Domain of the Stem Cell Factor Receptor Couples Ligand Binding to the Signal Transduction" Cell 80:103-113 (Jan. 13, 1995).

Bloom et al., "Intrachain disulfide bond in the core hinge region of human IgG4" Protein Sci 6:407-415 (1997).

Boix et al., "C-Met mRNA Overexpression in Human Hepatocellular Carcinoma" Hepatology 19(1):88-91 (Jan. 1994).

Bolt et al., "The generation of a humanized, non mitogenic CD3 monoclonal antibody which retains in vitro immunosuppressive properties" Eur J Immunol 23:403-411 (1993).

Bothmannet al., "The periplasmic *Escherichia coli* peptidylprolyl cis,trans-isomerase FkpA" J Biol Chem 275(22):17100-17105 (Jun. 2000).

(56) References Cited

OTHER PUBLICATIONS

Bottaro et al., "Identification of the Hepatocyte Growth Factor Receptor as the c-met Proto-Oncogene Product" Science 251:802-804 (Feb. 15, 1991).
Brocks et al., "ATNF receptor antagonistic scFv, which is not secreted in mammalian cells, is expressed as a soluble mono-and bivalent scFv derivative in insect cells" Immunotechnology 3(3):173-184 (Oct. 1997).
Brodeur et al. Monoclonal Antibody Production Techniques and Applications New York: Marcel Dekker, Inc.,:51-63 (1987).
Brooke et al., "A randomized, Phase II, multicenter, double-blind, placebo-controlled trial evaluating onartuzumab (MetMAb) and/or bevacizumab in combination with weekly paclitaxel in patients with metastatic triple-negative breast cancer" Poster 34th SABCS, pp. OT3-01-11 (2011).
Bruggemann et al., "Designer Mice: The Production of Human Antibody Repertoires in Transgenic Animals" Year Immunol 7:33-40 (1993).
Bussolino et al., "Hepatocyte Growth Factor is a Potent Angiogenic Factor Which Stimulates Endothelial Cell Motility and Growth" J Cell Biol 119 (3):629-641 (Nov. 1992).
Carter et al., "High level *Escherichia coli* expression and production of a bivalent humanized antibody fragment" Biotechnology 10(2):163-167 (Feb. 1992).
Carter et al., "Humanization of an Anti-p185HER3 Antibody for Human Cancer Therapy" P Natl Acad Sci USA 89(10):4285-4289 (May 1992).
Catenacci et al., "Durable Complete Response of Metastatic Gastric Cancer with Anti-Met Therapy followed by Resistance at Recurrence" Cancer Discovery 1(7):573-9 (2011).
Chowmow et al., "A Humanized, Bispecific Immunoadhesion-Antibody that Retargets CD3[3 +] Effectors to Kill HIV-1-Infected Cells" J Immunol 153(9):4268-4280 (Nov. 1, 1994).
Chan et al., Hepatocyte Growth Factor-Scatter Factor (HGF-SF) and the C-Met Receptor "Isoforms of human HGF and their biological activities" I.D. Goldberg and E.M. Rosen eds., Basel:Birkhauser Verlag,:67-79 (1993).
Chan et al., "Identification of a competitive HGF Antagonist Encoded by an Alternative Transcript" Science 254(5036):1382-1385 (Nov. 29, 1991).
Carlton, K.A., "Expression and isolation of recombinant antibody fragments in *E. coli*" Method Molec Biol 248:245-254 (2003).
Chen et al., "Chaperone Activity of DsbC" J Biol Chem 274(28):19601-19605 (Jul. 1999).
Chothia and Lesk, "Canonical Structures for the hypervariable regions of immunoglobulins" J Mol Biol 196(4):901-917 (1987).
Chothia et al., "Domain Association in Immunoglobulin Molecules. The Packing of Variable Domains" J Mol Biol 186(3):651-663 (Dec. 5, 1985).
Ciardiello et al., "Interaction between the epidermal growth factor receptor (EGFR) and the vascular endothelial growth factor (VEGF) pathways: a rational approach for multi-target anticancer therapy" Ann Oncol 17(7s):vii109-114 ( 2006).
Clark et al., "The improved lytic function and in vivo efficacy of monovalent monoclonal CD3 antibodieS" Eur J Immunol 19:381-388 (1989).
Clynes et al., "Fc receptors are required in passive and active immunity to melanoma" P Natl Acad Sci USA 95(2):652-656 (Jan. 1998).
Cobbold and Waldman, "Therapeutic potential of monovalent monoclonal antibodies" Nature 308(Suppl Mar. 29-Apr. 4):460-462 (1984).
Coltella et al., "Rol of the Met/HGF Receptor in Proliferation and Invasive Behavior of Osteosarcoma" FASEB J 17:1162-1164 (Jun. 2003).
Comoglio, P. Hepatocyte Growth Factor-Scatter Factor (HGF-SF) and the C-Met Receptor "Structure, biosynethesis and biochemical properties of the HGF receptor in normal and malignant cells" I.D. Goldberg and E.M. Rosen eds., Basel:Birkhauser Verlag,:131-16 (1993).
Comoglio, "The HGF Receptor and Its Ligand: Structure, Signal Transduction and Biology" Cell Bio Lint (Abstract S15-3), 18(5):375 (1994).
Cooper et al., "Amplification and Overexpression of the MET Gene in Spontaneously Transformed NIH3T3 Mouse Fibroblasts" EMBO J 5(10):2623-2628 (Oct. 1986).
Cooper et al., "Molecular cloning of a new transforming gene from a chemically transformed human cell line," Nature 311:29-33 (Sep. 6, 1984).
Crepaldi et al., "Targeting of the SF/HGF Receptor to the Basolateral Domain of Polarized Epithelial Cells" J Cell Biol 125(2):313-320 (Apr. 1994).
Danilkovitch-Miagkova & Zbar, "Dysregulation of Met receptor tyrosine kinase activity if invasive tumors" J Clin Invest 109(7):863-867 (Apr. 2002).
Daugherty et al.,"Formulation and delivery issues for monoclonal antibody therapeutics" Adv Drug Deliv Rev. 58:686-706 (2006).
David and Reisfeld, "Protein Iodination with Solid State Lactoperoxidase" Biochemistry—US 13(5):1014-1021 (Feb. 26, 1974).
de Sauvage et al., "Stimulation of Megakaryocytopoiesis and Thrombopoiesis by the c-Mpl Ligand" Nature 369(6481):533-538 (Jun. 16, 1994).
Defrances et al., "The Presence of the Hepatocyte Growth Factor in the Developing Rat" Development 116(2):387-395 (Oct. 1992).
Demignot et al., "Comparison of the Biodistribution of 791T/36 Monoclonal Antibody and Its Fab/c Fragment in BALB/c Mice and Nude Mice Bearing Human Tumor Xenografts" Cancer Res 50:2936-42 (May 1990).
Dennis et al., "Albumin binding as a general strategy for improving the pharmacokinetics of proteins" J Biol Chem 277(38): 35035-35043 (Sep. 20, 2002).
Di Renzo et al., "Overexpression and Amplification of the Met/HGF Receptor Gene During the Progression of Colorectal Cancer" Clin Cancer Res 1:147-154 (Feb. 1995).
Di Renzo et al., "Overexpression of the c-MET/HGF Receptor Gene in Human Thyroid Carcinomas" Oncogene 7(12):2549-2553 (Dec. 1992).
Di Renzo et al., "Selective Expression of the Met/HGF Receptor in Human Central Nervous System Microglia" Oncogene 8:219-222 (1993).
Dugner et al., "Harnessing phage and ribosome display for antibody optimization" Trends Biotechnology 24(11):523-529 (2006).
Duncan and Winter, "The Binding Site for C1q on IgG" Nature 332:738-740 (Apr. 21, 1998).
Eppler et al., "Complete Results from a Phase 1a Dose-Escalation and Dose-Expansion Study of Single-Agent MetMAb, a Monovalent Antagonist Antibody to the Receptor Met, Administered Intravenously in Patients with Locally Advanced or Metastatic Solid Tumors" Poster #2774-101st AACR, (2010).
Fan et al., "Blockade of Epidermal Growth Factor Receptor Function by Bivalent and Monovalent Fragments of 225 Anti-Epidermal Growth Factor Receptor Monoclonal Antibodies" Cancer Res 53(18):4322-4328 (Sep. 15, 1993).
Feng et al., "Anti-MET Targeted Therapy Has Come of Age: The First Durable Complete Response with MetMAb in Metastatic Gastric Cancer" Cancer Discovery 1(7):550-4 (2011).
Ferguson et al., "EGF Activates its Receptor by Removing Interactions that Autoinhibit Ectodomain Dimerization" Mol Cell 11:507-517 (Feb. 2003).
Furge et al., "Met Receptor Tyrosine Kinase: Enhanced Signaling Through Adapter Proteins" Oncogene 19:5582-5589 (2000).
Gallop et al., "Applications of Combinatorial Technologies to Drug Discovery Background and peptide combinatorial libraries" J Med Chem 37(9):1233-1251 (Apr. 29, 1994).
Garrett et al., "Crystal Structure of a Truncated Epidermal Growth Factor Receptor Extracellular Domain Bound to Transforming Growth Factor Alpha" Cell 110:763-773 (Sep. 20, 2002).
Gazzano-Santoro et al., "A non-radioactive complement-dependent cytotoxicity assay for anti-CD20 monoclonal antibody" J Immunol Methods 202:163-171 (1997).

(56) References Cited

OTHER PUBLICATIONS

Gherardi et al., "Functional map and domain structure of MET, the product of the c-met protooncogene and receptor for hepatocyte growth/factor scatter factor" P Natl Acad Sci USA 100(21):12039-12044 (Oct. 14, 2003).
Giancotti et al., "Integrin Signaling" Science 285:1028-1032 (Aug. 13, 1999).
Giordano et al., "Biosynthesis of the Protein Encoded by the C-MET Proto-Oncogene" Oncogene 4:1383-1388 (1989).
Giordano et al., "Different Point Mutations in the MET Oncogene Elicit Distinct Biological Properties" FASEB J 14:399-406 (Feb. 2000).
Giordano et al., "The Semaphorin 4D Receptor Controls Invasive Growth by Coupling with MET" Nat Cell Biol 4:720-724 (Sep. 2002).
Giordano et al., "Transfer of Motogenic and Invasive Response to Scatter Factor/Hepatocyte Growth Factor by Transfection of Human met Protooncogene" P Natl Acad Sci USA 90(2):649-653 (Jan. 15, 1993).
Giordano et al., "Tyrosine Kinase Receptor Indistinguishable from the C-Met Protein" Nature 339:155-156 (May 11, 1989).
Glennie and Stevenson, "Univalent antibodies kill tumor cells in vitro and in vivo" Nature 295:712-714 (1982).
Goding, "Monoclonal Antibodies: Principles and Practice Production and Application of Monoclonal Antibodies in cell Biology, Biochemistry and Immunology" Academic Press,:56-103 (1986).
Gohda et al., "Purification and Partial Characterization of Hepatocyte Growth Factor from Plasma of a Patient with Fulminant Hepatic Failure" J Clin Invest 81(2):414-419 (Feb. 1988).
Gorman, C., DNA Cloning: A Practical Approach "High Efficiency Gene Transfer," Glover, D.M., ed, Washington D.C.:IRL Press, vol. 2:143-190 (1985).
Hakimi et al., "Reduced immunogenicity and improved pharmacokinetics of humanized anti-Tac in cynomolgus monkeys" J Immunol 147(4):1352-1359 (Aug. 15, 1991).
Hamanoue et al., "Neurotrophic Effect of Hepatocyte Growth Factor on Central Nervous System in Vitro" J Neurosci Res 43:554-564 (1996).
Han et al., "Characterization of the DNF15S2 Locus on Human Chromosome 3: Identification of a Gene Coding for Four Kringle Domains with Homology to Hepatocyte Growth Factor" Biochemistry—US 30(40):9768-9780 (Oct. 8, 1991).
Handbook of Monoclonal Antibodies Ferrone et al. eds., Park Ridge, NJ:Noyes Publications,:293-359 and Chapter 22 (1985).
Hara et al., "Overproduction of Penicillin-Binding Protein 7 Suppresses Thermosensitive Growth Defect at Low Osmolarity Due to an spr Mutation of *Escherichia coli*" Microb Drug Resist 2(1):63-72 (1996).
Harris et al., "Therapeutic Antibodies—The Coming of Age" Trends Biotechnol 11(2):42-44 (Feb. 1993).
Hartmann et al., "A Functional Domain in the Heavy Chain of Scatter Factor/Hepatocyte Growth Factor Binds the c-Met Receptor and Induces Cell Dissociation by Not Mitogenesis" P Natl Acad Sci USA 89(23):11574-11578 (Dec. 1, 1992).
Hartmann et al., "The Motility Signal of Scatter Factor/Hepatocyte Growth Factor Mediated Through the Receptor Tyrosine Kinase Met Requires Intercellular Action of Ras" J Biol Chem 269(35):21936-21939 (Sep. 2, 1994).
Hawkins et al., "Selection of phage antibodies by binding affinity mimicking affinity maturation" J Mol Biol 226:889-896 (1992).
Hirsch et al., "A randomized, Phase II, multicenter, double-blind, placebo-controlled study of onartuzumab (MetMAb) in combination with paclitaxel plus cisplatin (or carboplatin) as first-line treatment for patients (pts) with Stage IIIb of IV squamous non-small cell lung cancer (NSCLC)" 37th Congress ESMO—Poster 1365TiP, (2012).
Hirsch et al., "A randomized, Phase II, multicenter, double-blind, placebo-controlled study of onartuzumab (MetMAb) in combination with paclitaxel plus cisplatin (or carboplatin) as first-line treatment for patients (pts) with Stage IIIb of IV squamous non-small cell lung cancer (NSCLC)" 37th Congress ESMO—Abstract 2593, (2012).
Hoogenboom et al., "By-passing immunization. Human antibodies from synthetic repertoires of germline VH gene segments rearranged in vitro" J Mol Biol 227(2):3/81-388 (Sep. 20, 1992).
Humphreys et al., "Formation of dimeric Fabs in *Escherichia coli*: effect of hinge size and isotype, presence of interchain disulphide bond, Fab' expression levels, tail piece sequences and growth conditions" J Immunol Methods 209(2): 193-202 (Dec. 1, 1997).
Hunter et al., "Preparation of Iodine-131 Labelled Human Growth Hormone of High Specific Activity" Nature 194(4827):495-496 (May 5, 1962).
Igawa et al., "Hepatocyte Growth Factor is a Potent Mitogen for Cultured Rabbit Renal Tubular Epithelial Cells" Biochem Bioph Res Co 174(2):831-838 (Jan. 31, 1991).
Iyer et al., "Structure, Tissue-Specific Expression, and Transforming Activity of the Mouse met Protooncogene" Cell Growth Differ 1(2):87-95 (Feb. 1990).
Jackson et al., "In vitro antibody maturation. Improvement of a high affinity, neutralizing antibody against IL-1 beta" J Immunol 154(7):3310-3319 (Apr. 1, 1995).
Jaffers et al., "Monoclonal Antibody Therapy, Anti-Idiotypic and Non-Anti-Idiotypic Antibodies to OKT3 Arising Despite Intense Immunosuppression" Transplantation 41(5):572-578 (May 1986).
Jagoda et al., "Comparison of [89Zr] and [76Br] labeled MetMAb, a one-armed monoclonal antibody targeting the Met receptor tyrosine kinase (Met, in human gastric carcinoma (MKN-45) and glioblastoma (U87 MG) cells and xenogrfts" Abstract $19^{th}$ Int'l Symposium on Radiopharmceutical Sciences, Amsterdam, Netherlands, pp. P-083 (2001).
Jakobovits et al., "Analysis of Homozygous Mutant Chimeric Mice: Deletion of the Immunoglobulin Heavy-Chain Joining Region Blocks B-cell Development and Antibody Production" P Natl Acad Sci USA 90(6):2551-2555 (Mar. 15, 1993).
Jakobovits et al., "Germ-line Transmission and Expression of a Human-Derived Yeast Artificial Chromosome" Nature 362(6417):225-258 (Mar. 18, 1993).
Jeffers et al., "Activating Mutations for the Met Tyrosine Kinase Receptor in Human Cancer" P Natl Acad Sci USA 94:11445-11450 (Oct. 1997).
Jeffers et al., "Enhanced Tumorigenicity and Invasion-Metastasis by Hepatocyte Growth Factor/Scatter Factor-met Signaling in Human Cells Concomitant with Induction of the Urokinase Proteolysis Network" Mol Cell Biol 16(3)1115-1125 (Mar. 1996).
Jin et al., "Expression of Scatter Factor and C-Met Receptor in Benign and Malignant Breast Tissue" Cancer 79(4):749-760 (Feb. 15, 1997).
Jin et al., "MetMab, the One-armed 5D5 anti-c-Met antibody, inhibits orthotopic pancreatic tumor growth and improves survival" Cancer Res 68(11):4360-8 (Jun. 2008).
Junghans et al., "Anti-Tac-H, a Humanized Antibody to the Interleukin 2 Receptor with New Features for Immunotherapy in Malignant and Immune Disorders" Cancer Res 50(5):1495-1502 (Mar. 1, 1990).
Kabat et al., Bethesda, MD:National Institute of Health, :2 pages (1983).
Kerwin et al., "Polysorbates 20 and 80 used in the formulation of protein biotherapeutics: structure and degradation pathways" J Pharm Sci. 97(8):2924-35 (2008).
Khazaeli et al., "Phase I trial of multiple large dose of murine monoclonal antibody CO17-IA. II Pharmacokinetics and immune response" J Natl Cancer Inst 80(12):937-942 (Aug. 17, 1988).
Knudsen and Vande Woude, "Showering c-MET-dependent cancers with drugs" Curr Opin Genet Dev 18:87-96 (2008).
Kohler and Milstein, "Continuous cultures of fused cells secreting antibody of predefined specificity" Nature 256:495-497 (Aug. 7, 1975).
Kong-Beltran et al., "Somatic mutations lead to an oncogenic deletion of met in lung cancer" Cancer Res 66(1):283-289 (Jan. 1, 2006).
Kong-Beltran et al., "The sema domain of Met is Necessary for Receptor Dimerization and Activation" Cancer Cell 6:75-84 (2004).

(56) References Cited

OTHER PUBLICATIONS

Kozbor et al., "A Human Hybrid Myeloma for Production of Human Monoclonal Antibodies" J Immunol 133(6):3001-3005 (Dec. 1, 1984).
Krauss et al., "Specificity grafting of human antibody frameworks selected from a phage display library: generation of a phage display library: generation of a highly stable humanized anti-CD22 single-chain Fv fragment" Protein Engineering 16(10):753-759 (2003).
Kuniyasu et al., "Aberrant Expression of C-met mRNA in Human Gastric Carcinomas" Int J Cancer 55:72-75 (1993).
Lee et al., "High-affinity human antibodies from phage-displayed synthetic Fab libraries with a single framework scaffold" J Mol Biol 340(5):1073-1093 (Jul. 23, 2004).
Lev et al., "A Recombinant Ectodomain of the Receptor for the Stem Cell Factor (SCF) Retains Ligand-induced Receptor Dimerization and Antagonizes SCF-Stimulated Cellular Responses" J Biol Chem 267(15):10866-10873 (May 25, 1992).
Li et al., "Circulating Biomarkers of MetMAb Activity in a Phase la Dose Escalating Clinical Trial" 101$^{st}$ AACR—Poster 1670, (2010).
Lindmark et al., "Binding of immunoglobulins to protein A and immunoglobulin levels in mammalian sera" J Immunol Methods 62:1-13 (1983).
Lindroos et al., "Hepatocyte Growth Factor (Hepatopoietin A) Rapidly Increases in Plasma before DNA Synthesis and Liver Regeneration Stimulated by Partial Hepatectomy and Carbon Tetrachloride Administration" Hepatology 13(4): 743-750 (Apr. 1991).
Liu et al., "A Novel Kinase Inhibitor, INCB28060, Blocks c-MET-Dependent Signaling, Neoplastic Activities, and Cross-Talk with EGFR and HER-3" Clin. Cancer Res.17(22):7127-38 ( 2011).
Liu et al., "Overexpression of C-met Proto-Oncogene But Not Epidermal Growth Factor Receptor or C-erbB-2 in Primary Human Colorectal Carcinomas" Oncogene 7: 181-185 (1992).
Liu et al., "Targeting the c-Met signaling pathway for cancer therapy" Expert Opin Inv Drug 17(7):997-1011 (2008).
Lokker et al., "Generation and Characterization of a Competitive Antagonist of Human Hepatocyte Growth Factor, HGF/NK1" J Biol Chem 268(23):17145-17150 (Aug. 15, 1993).
Lokker et al., "Structure-Function Analysis of Hepatocyte Growth Factor: Identification of Variants that Lack Mitogenic Activity Yet Retain High Affinity Receptor Binding" EMBO J 11(7):2503-2510 (1992).
Lorenzato et al., "Novel Somatic Mutations of the MET Oncogene in Human Carcinoma Metastases Activating Cell Motility and Invasion" Cancer Res 62:7025-7030 (Dec. 1, 2002).
Love et al., "The Ligand-binding Face of the Semaphorins Revealed by the High-Resolution Crystal Structure of SEMA4D" Nat Struct Biol 10(10):843-848 (Oct. 2003).
Maina et al., "Uncoupling of Grb2 from the Met Receptor in Vivo Reveals Complex Roles in Muscle Development" Cell 87:531-542 (Nov. 1, 1996).
Mark et al., "Expression and Characterization of Hepatocyte Growth Factor Receptor-IgG Fusion Proteins" J Biol Chem 267(36):26166-26171 (Dec. 25, 1992).
Martens et al., "A novel one-armed anti-c met antibody inhibits glioblastoma growth in vivo" Clin Cancer Res 12(20):6144-6152 (Oct. 2006).
Masuya et al., "The tumour-stromal interaction between intratumoral c-Met and stromal hepatocyte growth factor associated with tumour growth and prognosis in non-small-cell lung cancer patients" British Journal of Cancer 90: 1555-1562 ( 2004).
Matsumoto et al., "Roles of HGF as a pleiotropic factor in organ regeneration" EXS 65:225-249 (1993).
Matsumoto et al., "Deletion of Kringle Domains or the N-Terminal Hairpin Structure in Hepatocyte Growth Factor Results in Marked Decreases in Related Biological Activities" Biochem Bioph Res Co 181(2):691-699 (Dec. 16, 1991).
Matsumoto et al., "Hepatocyte Growth Factor is a Potent Stimulator of Human Melanocyte DNA Synthesis and Growth" Biochem Bioph Res Co 176(1):45-51 (Apr. 15, 1991).
Maulik et al., "Role of the hepatocyte growth factor receptor, c-Met, in oncogenesis and potential for therapeutic inhibition" Cytokine Growth F R 13(1):41-59 (Feb. 2002).
Meiners et al., "Role of Morphogenetic Factors in Metastasis of Mammary Carcinoma Cells" Oncogene 16:9-20 (1998).
Merchant et al., "Combination efficacy with MetMAb and erlotinib in a NSCLC tumor model highlight therapeutic opportunities for c-Met inhibitors in combination with EGFR inhibitors" Presented at 99th AACR Annual meeting 2008, Apr. 12-16, San Diego, CA (Abstract 1336).
Merchant et al., "An efficient rout to human bispecific IgG" Nat Biotechnol 16(7):677-681 (1998).
Merchant et al., "Monovalent antibody design and mechanism of action of onartuzumab, a MET antagonist with anti-tumor activity as a therapeutic agent" Proc Natl Acad Sci U S A. (Epub Jul. 23, 2013.), 110(32):E2987-96 (Aug. 6, 2013).
Merchant et al., "Proof of concept of immuno-PET molecular imaging of met using 76Br- and 89Zr- labeled MetMAb" 47$^{th}$ ASCO—Poster 10632, (2001).
Merchant et al., "Therapeutic opportunities for MetMAb in breast cancer, based on Met expression and function in cell lines and primary tumors" (Abstract) 23$^{rd}$ AACR, (2011).
Michalopoulos et al., "Control of Hepatocyte Replication by Two Serum Factors" Cancer Res 44(10):4414-4419 (Oct. 1984).
Michieli et al., "Targeting the tumor and its microenvironment by a dual-function decoy Met receptor" Cancer Cell 6(1):61-73 (Jul. 2004).
Miller et al., "Monoclonal antibody therapeutic trials in seven patients with T-cell lymphoma" Blood 62:988-995 (1983).
Miyazawa et al., "An Alternatively Processed mRNA Generated from Human Hepatocyte Growth Factor Gene" Eur J Biochem 197(1):15-22 (Apr. 10, 1991).
Miyazawa et al., "Molecular cloning and sequence analysis of cDNA for human hepatocyte growth factor" Biochem Bioph Res Co 163(2):967-973 (Sep. 15, 1989).
Montesano et al., "Identification of a Fibroblast-Derived Epithelial Morphogen as Hepatocyte Growth Facto" Cell 67:901-908 (Nov. 29, 1991).
Morello et al., "MET Receptor is Overexpressed but not Mutated in Oral Squamous Cell Carcinomas" J Cell Physiol 189:285-290 (2001).
Morimoto et al., "A risk-based approach to the immunogenicity assessment of a novel onearmed antibody" Slides 7th Protein Engineering Summit, (2011).
Morimoto et al., "A risk-based approach to the immunogenicity assessment of a novel one-armed antibody" Abstract 7th Protein Engineering Summit, (2011).
Morrison et al., "Chimeric human antibody molecules: Mouse antigen-binding domains with human constant region domains" P Natl Acad Sci USA 81:6581-6855 (Nov. 1984).
Morton et al., "In vitro and in vivo activity of fully-human monoclonal antibodies to c-Met protein tyrosine kinase" Proceedings Annual Meeting Am Association for Cancer Research (XP-001194900 #5604), 44:1116 (Jul. 2003).
Morton et al., "In vitro and in vivo activity of fully-human monoclonal antibodies to c-Met protein tyrosine kinase" Proceedings of the American Association for Cancer Research (44):1284 (Mar. 2003).
Moss et al., "Complete Results from a Phase I Dose Escalation Study of MetMab, A Monovalent Antagonist Antibody to the Receptor Met, Dosed as Single Agent and in Combination with Bevacizumab in Patients with Advanced Solid Malignancies" 35th ESMO Congress—Abstract 504P, (2010).
Moss et al., "Complete results from phase I dose escalation study of MetMAb, a monovalent antagonist antibody to the receptor Met, dosed as single agent and in combination with Bevacizumab in patients with advanced solid malignancies" 35th ESMO Congress—Abstract viii165, Milan, Italy, ( Oct. 2010).
Moss et al., "Final results from the Phase I study of MetMAb, a monovalent antagonist antibody do the receptor MET, dosed as single agent and in combination with bevacizumab in patients with

(56) References Cited

OTHER PUBLICATIONS advanced solid malignancies" Abstract AACR-NCI-EORTC Symposium on Molecular Targets and Cancer Therapeutics—23rd AACR, (Apr. 23, 2011).
Moss et al., "Phase lb dose-escalation study of MetMAb, a monovalent antagonist antibody to the receptor Met, in combination with Bevacizumab in patients with locally advanced or metastatic solid tumors" Abstract Annual Meeting of the American Society of Clinical Oncology (ASCO),Chicago, IL, pp. e13050 ( Jun. 2010).
Munson and Rodbard, "Ligand: A Versatile Computerized Approach for Characterization of Ligand-Binding Systems" Anal Biochem 107(1):220-239 (Sep. 1, 1980).
Naka et al., "Activation of Hepatocyte Growth Factor by Proteolytic Conversion of a Single Chain Form to a Heterodimer" J Biol Chem 267(28):20114-20119 (Oct. 5, 1992).
Nakamura et al., "Molecular Cloning and Expression of Human Hepatocyte Growth Factor" Nature 342:440-443 (Nov. 23, 1989).
Nakamura et al., "Partial Purification and Characterization of Hepatocyte Growth Factor from Serum of Hepatectomized Rats" Biochem Bioph Res Co 122:1450-1459 (Aug. 16, 1984).
Nakamura et al., "Purification and Characterization of a Growth Factor from Rat Platelets for Mature Parenchymal Hepatocytes in Primary Cultures" P Na Tl Acad Sci USA 83(17):64896493 (Sep. 1986).
Nakamura et al., "Purification and Subunit Structure of Hepatocyte Growth Factor from Rat Platelets" Febs Lett 224(2):311-316 (Nov. 1987).
Naldini et al., "Hepatocyte Growth Factor (HGF) Stimulates the Tyrosine Kinase Activity of the Receptor Encoded by the Proto-Oncogene c-MET" Oncogene 6(4):501-504 (Apr. 1991).
Naldini et al., "Scatter Factor and Hepatocyte Growth Factor are Indistinguishable Ligands for the MET Receptor" EMBO J 10(10):2867-2878 (Oct. 1991).
Natali et al., "Overexpression of the Met/HGF Receptor in Renal Cell Carcinomas" Int J Cancer 69:212-217 (1996).
Nguyen et al., "Association of the Multisubstrate Docking Protein Gab1 with the Hepatocyte Growth Factor Receptor Requires a Functional Grb2 Binding Site Involving Tyrosine 1356" J Biol Chem 272(33):20811-20819 (Aug. 15, 1997).
Nielsen and Routledge, "Human T cells resistant to complement lysis by bivalent antibody can be efficiently lysed by dimers of monovalent antibody." Blood 100(12):4067-4073 (Dec. 1, 2002).
Novotny and Haber, "Structure invariants of antigen binding: comparison of immunoglobulin VL-VH and VL-VL domain dimers" P Natl Acad Sci USA 82(14):4592-4596 (Jul. 1985).
Nusrat et al., "Hepatocyte Growth Factor/Scatter Factor Effects on Epithelia. Regulation of Intercellular Junctions in Transformed and Natural Intestinal Epithelia and Induction of Rapid Wound Repair in a Transformed Model Epithelium" J Clin Invest 93:2056-2065 (May 1994).
Nygren, H., "Conjugation of Horseradish Peroxidase to Fab Fragments with Different Homobifunctional and Heterobifunctional Cross-Linking Reagents" J Histochem Cytochem 30(5):407-412 (May 1982).
Ogiso et al., "Crystal Structure of the Complex of Human Epidermal Growth Factor and Receptor Extracellular Domains" Cell 110:775-787 (Sep. 20, 2002).
Okajlma et al., "Primary Structure of Rat Hepatocyte Growth Factor and Induction of its mRNA During Liver Regeneration Following Hepatic Injury" Eur J Biochem 193(2):375-381 (Oct. 24, 1990).
Okamoto et al., "TAK-701, a Humanized Monoclonal Antibody to Hepatocyte Growth Factor, Reverses Gefitinib Resistance Induced by Tumor-Derived HGF in Non-Small Cell Lung Cancer with and EGFR Mutation" Mol. Cancer Ther. 9(10):2785-92 ( 2010).
Olivero et al., "Novel Mutation in the ATP-Binding Site of the MET Oncogene Tyrosine Kinase in a HPRCC Family" Int J Cancer 82:640-643 (1999).
Olivero et al., "Overexpression and Activation of Hepatocyte Growth Factor/Scatter Factor in Human Non-Small-Cell Lung Carcinomas" Brit J Cancer 74:1862-1868 (1996).

Orian-Rousseau et al., "CD44 is Required for Two Consecutive Steps in HGF/c-MET Signaling" Gene Dev 16:3074-3086 (2002).
Paccjoama et al., "Monovalency Unleashes the Full Therapeutic Potential of the DN-30 Anti-Met Antibody" J. of Biological Chem. 285:46):36149-157 (2010).
Padlan, Eduardo, "Anatomy of the Antibody Molecule" Mol Immunol 31(3):169-217 (Feb. 1994).
Pain and Surolia, "Preparation of Protein A-Peroxidase Monoconjugate Using a Heterobifunctional Reagent, and its Use in Enzyme Immunoassays" J Immunol Methods 40(2):219-230 (1981).
Palacios and Steinmetz, "IL3-Dependent Mouse Clones That Express B-220 Surface Antigen, Contain Ig Genes in Germ-Line Configuration, and Generate B Lymphocytes In Vivo" Cell 41(3):727-734 (Jul. 1985).
Parham, Peter, "On the fragmentation of monoclonal IgG1, IgG2a, and IgG2b from BALB/c mice" J Immunol 131(6):2895-2902 (Dec. 1983).
Park et al., "Mechanism of Met Oncogene Activation" Cell 45:895-904 (Jun. 20, 1986).
Park et al., "Sequence of MET Protooncogene c DNA has Features Characteristic of the Tyrosine Kinase Family of Growth-Factor Receptors" P Natl Acad Sci USA 84(18):6379-6383 (Sep. 1987).
Patel et al., "Results from FDG-PET Imaging in Oam 4558g, a Randomized, Placebo-Controlled, Multi-center Phase II Trial of Erlotinib + MetMAb in Second-and-Third Line NSCLC" Slides World Conference on Lung Cancer—14$^{th}$, (Jul. 3, 2011).
Patel et al., "Results from FDG-PET Imaging in OAM 4558g, a Randomized, Placebo-Controlled, Multi-center Phase II Trial of Erlotinib + MetMAb in Second-and-Third Line NSCLC" Abstract World Conference on Lung Cancer—14$^{th}$, (Jul. 3, 2011).
PCT ISR for PCT/US2012/044829 mailed Sep. 20, 2012.
Peek et al., "Unusual Proteolytic Activation of Pro-hepatocyte Growth Factor by Plasma Kallikrein and Coagulation Factor Xla" J Biol Chem 277(49):47804-9 (Dec. 6, 2002).
Pelicci et al., "The Motogenic and Mitogenic Responses to HGF are Amplified by the Shc Adaptor Protein" Oncogene 10: 1631-1638 (1995).
Plotnikov et al., "Structural Basis for FGF Receptor Dimerization and Activation" Cell 98:641-650 (Sep. 3, 1999).
Ponzetto et al., "Specific Uncoupling of GRB2 from the Met Receptor. Different Effects on Transformation and Motility" J Biol Chem 271(24):14119-14123 (Jun. 14, 1996).
Ponzetto et al., "A Multifunctional Docking Site Mediates Signaling and Transformation by the Hepatocyte Growth Factor/Scatter Factor Receptor Family" Cell 77:261-271 (Apr. 22, 1994).
Ponzetto et al., "A Novel Recognition Motif for Phosphatidylinositol 3-Kinase Binding Mediates Its Association With the Hepatocyte Growth Factor/Scatter Factor Receptor" Mol Cell Biol 13(8):4600-4608 (Aug. 1993).
Ponzetto et al., "c-met is Amp lifted But Not Mutated in a Cell Line with an Activated met Tyrosine Kinase" Oncogene 6(4):553-559 (Apr. 1991).
Portolano et al., "Lack of promiscuity in autoantigen-specific H and L chain combinations as revealed by human H and L chain 'Roulette'"J Immunol 150(3):880-887 (Feb. 1993).
Prat et al., "Agonistic monoclonal antibodies against the Met receptor dissect the biological responses to HGF" J Cell Sci (111):237-247 (1998).
Prat et al., "C-Terminal Truncated Forms of Met, the Hepatocyte Growth Factor Receptor" Mol Cell Biol 11(12):5954-5962 (Dec. 1991).
Prat et al., "The HGF Receptor (Met): Transduction of Signals for Invasive Cell Growth" Antibody Immunoconj 8(4):341-361 (1995).
Prat et al., "The Receptor Encoded by the Human c-Met Oncogene is Expressed in Hepatocytes, Epithelial Cells and Solid Tumors" Int J Cancer 49(3):323-328(Sep. 30, 1991).
Presta et al., "Humanization of an Antibody Directed Against IgE" J Immunol 151(5):2623-2632 (Sep. 1, 1993).
Ramlau et al., "Efficacy and Safety in the Cross-over Arm of OAM455Sg; a Phase II Study Evaluating MetMAb in Combination with Erlotinib in Advanced NSCLC" World Conference on Lung Cancer—Poster 1672, (Jul. 3, 2011).

(56) References Cited

OTHER PUBLICATIONS

Ramlau et al., "Efficacy and Safety in the Cross-over Arm of OAM455Sg; a Phase II Study Evaluating MetMAb in Combination with Erlotinib in Advanced NSCLC" (Abstract) World Conference on Lung Cancer, (Jul. 3, 2011).
Ramm et al., "The periplasmic Escherichia coli peptidylprolyl cis, trans isomerase FkpA" J Biol Chem 275(22):17106-17113 (Jun. 2000).
Ravetch et al., "Fc receptors" Annu Rev Immunol 9:457-492 (1991).
Ridgway et al., "'Knobs-into-holes' Engineering of Antibody CH3 Domains for Heavy Chain Heterodimerization" Protein Eng 9(7):617-621 (1996).
Riechmann et al., "Reshaping human antibodies for therapy" Nature 332:323-337 (1988).
Robertson et al., "RTK Mutations and Human Syndromes when Good Receptors Turn Bad" Trends Genet 16(8):265-271 (Aug. 16, 2000).
Rodrigues et al., "Alternative Splicing Generates Isoforms of the met Receptor Tyrosine Kinase Which Undergo Differential Processing" Mol Cell Biol 11 ( 6):2962-2970 (Jun. 1991).
Rodriques et al., "Development of a humanized disulfide-stabilized anti-p185HER2 Fv-beta-lactamase fusion protein for activation of a cephalosporin doxorubicin prodrug" Cancer Res 55(1):63-70 (Jan. 1, 1995).
Rosen et al., "AMG102, an HGF/SF antagonist, in combination with anti-angiogenesis targeted therapies in adult patients with advanced solid tumors" J Clin Oncol 26(15s):3570 (May 2008).
Routledge et al., "A Humanized Monovalent CD3 Antibody which Can Activate Homologous Complement" Eur J Immunol 21 :2717-2725 (1991).
Routledge et al., "The effect of aglycosylation on the immunogenicity of a humanized therapeutic CD3 monoclonal antibody" Transplantation 60(8):847-853 (Oct. 27, 1995).
Royal and Park, "Hepatocyte Growth Factor-Induced Scatter of Madin-Darby Canine Kidney Cells Requires Phosphatidylinositol 3-Kinase" J Biol Chem 270(46):27780-27787 (Nov. 17, 1995).
Rubin et al., "A Broad-Spectrum Human Lung Fibroblast-Derived Mitogen is a Variant of Hepatocyte Growth Factor" P Natl Acad Sci USA 88(2):415-419 (Jan. 15, 1991).
Russel et al., "Partial Characterization of a Hepatocyte Growth Factor From Rat Platelets" J Cell Physiol 119(2):183-192 (May 1984).
Salgia et al., "Complete results from a phase la dose-escalation and dose-expansion study of single-agent MetMab, a monovalent antagonist antibody to the receptor MET, administered intravenously in patients with locally advanced or metastatic solid tumors" Abstract AACR 101$^{st}$ Annual Meeting, Washington, D.C., pp. 2774 (2010).
Sano et al., "Abstract 2728: Onartuzumab (MetMab) restores sensitivity to erlotinib in EGFR mutant NSCLC cells expressing HGF" Cancer Research 72(8 Suppl 1) (Apr. 15, 2012).
Schier et al., "Identification of functional and structural amino-acid residues by parsimonious mutagenesis" Gene 169:147-155 (1996).
Schlom Molecular Foundations Oncology "6" Broder, S. ed., Baltimore, MD:Williams & Wilkins,:95-134 (1991).
Schmidt et al., "Germline and Somatic Mutations in the Tyrosine Kinase Domain of the MET Proto-oncogene in Papillary Renal Carcinomas" Nat Genet 16:68-73 (May 1997).
Schmidt et al., "Novel Mutations of the MET Proto-oncogene in Papillary Renal Carcinomas" Oncogene 18:2343-2350 (1999).
Schmidt et al., "Scatter factor/hepatocyte growth factor is essential for liver development" Nature 373:699-702 (Feb. 23, 1995).
Schwall et al., "Heparin induces dimerization and confers proliferative activity onto the hepatocyte growth factor antagonists NK1 and NK2" J Cell Biol 133:709-718 (May 1996).
Sears et al., "Effects of monoclonal antibody immunotherapy on patients with gastrointestinal adenocarcinoma" J Biol Response Mod 3(2):138-150 (1984).

Seki et al., "Isolation and Expression of cDNA for Different Forms of Hepatocyte Growth Factor from Human Leukocyte" Biochem Bioph Res Co 172(1):321-327 (Oct. 15, 1990).
Sharma et al., "In the Clinic: Ongoing Clinical Trials Evaluating c-MET-inhibiting Drugs" Ther. Adv. Med. Oncol. 3(S1):S37-550 (2011).
Shawler et al., "Human immune response to multiple injections of murine monoclonal IgG" J Immunol 135(2):1530-1535 (1985).
Simmons and Yansura, "Translational level is a critical factor for the secretion of heterologous proteins in *Escherichia coli*" Nat Biotechnol 14:629-634 (May 1996).
Simmons et al., "Expression of full-length immunoglobulins in *Escherichia coli*: Rapid and efficient production of aglycosylated antibodies" J Immunol Methods 263:133-147 (2002).
Sims et al., "A Humanized CD18 Antibody Can Block Function Without Cell Destruction" J Immunol 151(4):2296-2308 (Aug. 15, 1993).
Smith et al., "Cardiac Glycoside-Specific Antibodies in the Treatment of Digitalis Intoxication" Antibodies Human Diagnosis Therapy:365-389 (1977).
Spigel et al., "Treatment rationale study design for the MetLung trial: A randomized, double-blind Phase III study of onartuzumab (MetMAb) in combination with erlotinib versus erlotinib alone in patients who have received standard chemotherapy for stage IIIB or IV Met-positive non-small-cell lung cancer" Clinical Lung Cancer:500-03 (Nov. 2012).
Spigel et al., "Final efficacy results from a randomized phase II study (OAM4558g) evaluating MetMAb or placebo in combination with erlotinib in advanced NSCLC" WCLC Abstract, ( Feb. 21, 2011).
Spigel et al., "Final efficacy results from OAM4558g, a randomized Phase II study evaluating MetMAb or placebo in combination with erlotinib in advanced NSCLC" (Slides) World Conference on Lung Cancer, (Jul. 3, 2011).
Spigel et al., "Final efficacy results from OAM4558g, a randomized phase II study evaluating MetMAb or placebo in combination with erlotinib in advanced NSCLC" J. of Clinical Oncology 28(155):7505 (2011).
Spigel et al., "Randomized global double-blind phase II study evaluating MetMAb in combination with Erlotinib, in patients with advanced non-small-cell lung cancer" Journal of Thoracic Oncology 5(12 Suppl 7):S557 (Dec. 2010).
Spigel et al., "Randomized multicenter double-blind placebo controlled phase II study evaluating MetMAb, an antibody to Met receptor, in combination with Erlotinib, in patients with advanced non-small-cell lung cancer" (Abstract) 35th ESMO Congress, Milan, Italy, (Oct. 2010).
Spigel et al., "Randomized multicenter double-blind placebo-controlled phase II study evaluating MetMAb, an antibody to Met receptor, in combination with Erlotinib, in patients with advanced non-small-cell lung cancer" Annals of Oncology 21 ( Suppl 8):LBA15 (Oct. 2010).
Spigel et al., "The MetLUNG study: A randomized, double-blind, phase III study of onartuzumab (MetMAb) + erlotinib versus placebo+ erlotinib in patients with advanced, Met-positive non-small cell lung cancer (NSCLC)" (Abstract) 48th ASCO, (2012).
Staerz et al., "Hybrid antibodies can target sites for attack by T cells" Nature 314(6012SUPPL Apr. 18-24):628-631 ( 1985).
Stevenson et al., "A Chimeric Antibody With Dual Fc Regions (bisFabFc) Prepared by manipulations at the IgG Hinge" Anti-Cancer Drug Des 3(4):219-230 ( 1989).
Stoker et al., "Scatter Factor is a Fibroblast-Derived Modulator of Epithelial Cell Mobility" Nature 327(6119):239-242 (May 21, 1987).
Sunitha et al., "Hepatocyte Growth Factor Stimulates Invasion Across Reconstituted Basement Membranes by a New Human Small Intestinal Cell Line" Cline XP Metastasis 12(2):143-154 (Mar. 1994).
Suzuki et al., "Expression of the C-Met Protooncogene in Human Hepatocellular Carcinoma" Hepatology 20:1231-1236 (Nov. 1994).
Tamagnone et al., "Plexins are a Large Family of Receptors for Transmembrane, Secreted, and GPI-Anchored Semaphorins in Vertebrates" Cell 99:71-80 (Oct. 1, 1999).

(56) References Cited

OTHER PUBLICATIONS

Tanizaki et al., "MET Tyrosine Kinase Inhibitor Crizotinib (PF-02341066) Shows Differential Antitumor Effects in Non-small Cell Lung Cancer According to MET Alterations" Journal of Thoracic Oncology 6(10):1624-31 (2011).
Tashiro et al., "Deduced Primary Structure of Rat Hepatocyte Growth Factor and Expression of the mRNA in Rat Tissues" P Natl Acad Sci USA 87(8):3200-3204 (Apr. 1990).
Tempest et al., "Structure of the Met Protein and Variation of Met Protein Kinase Activity Among Human Tumour Cell Lines" Brit J Cancer 58(1):3-7 (Jul. 1988).
Tramontano et al., "Framework residue 71 is a major determinant of the position and conformation of the second hypervariable region in the $V_H$ domains of immunoglobulins" J Mol Biol 215(1):175-182 (Sep. 5, 1990).
Trusolino & Comoglio, "Scatter-Factor and Semaphorin Receptors: Cell Signaling for Invasive Growth" Nature Rev Cancer 2(4):289-300 (Apr. 2002).
Trusolino et al., "A Signaling Adapter Function for Alpha6beta4 Integrin in the Control of HGF-Dependent Invasive Growth" Cell 107:643-654 (Nov. 30, 2001).
Uehara et al., "Placental defect and embryonic lethality in mice lacking hepatocyte growth factor/scatter factor" Nature 373:702-705 (Feb. 23, 1995).
Upstate Biotechnology Inc. (1993-2016). "Anti-Human Met Monoclonal Antibodies (product literature)," located at <http://upstatebiotech.com>, last visited on Mar. 1, 2016, 3 pages.
Vajdos et al., "Comprehensive functional maps of the antigen-binding site of an anti-ErbB2 antibody obtained with shotgun scanning mutagenesis" J Mol Biol 320:415-428 (2002).
Van Vactor and Lorenz, "Neural Development: The Semantics of Axon Guidance" Curr Biol 9(6):R201-204 (1999).
Vanhove et al., "Selective blockade of CD28 and not CTLA-4 with a single-chain Fv-alpha1-antitrypsin fusion antibody" Blood 102(2):564-570 (Jul. 15, 2003).
Vashishtha et al., "Adverse events and patterns of tumor progression in Met diagnostic subgroups in OAM4558g; a phase II study evaluating MetMAb or placebo in combination with erlotinib in advanced NSCLC" (Abstract) World Conference on Lung Cancer, (Jul. 3, 2011).
Vashishtha et al., "Adverse events and patterns of tumor progression in Met diagnostic subgroups in OAM4558g: a phase II study evaluating MetMAb or placebo in combination with erlotinib in advanced NSCLC" (Poster 1985) World Conference on Lung Cancer, (Jul. 3, 2011).
Vashishtha et al., "Safety data and patterns of progression in Met diagnostic subgroups in OAM4558g: a phase II study evaluating MetMAb in combination with erlotinib in advanced NSCLC" (Poster 7604) American Society of Clinical Oncology 47th Annual Meeting, (Jun. 3, 2011).
Verhoeyen et al., "Reshaping human antibodies: Grafting an antilysozyme activity" Science 239:1534-1536 (Mar. 1988).
Wakelee et al., "A randomized, Phase II, multicentre, double-blind, placebo-controlled study of onartuzumab (MetMAb) with either bevacizumab plus platinum plus paclitaxel or pemetrexed plus platinum as first-line treatment for patients (pts) with Stage IIIb or IV non-squamous non-small cell lung cancer (NSCLC)" (Poster 1364TiP) ESMO, (2012).
Wakelee et al., "A randomized, Phase II, multicentre, double-blind, placebo-controlled study of onartuzumab (MetMAb) with either bevacizumab + platinum + paclitaxel or pemetrexed + platinum as first-line treatment for patients (pts) with Stage IIIB or IV non-squamous non-small cell lung cancer (NSCLC)" ((Abstract 2514)) 37th Congress ESMO, (2012).
Weidner et al., "Interaction Between Gab1 and the C-Met Receptor Tyrosine Kinase is Responsible for Epithelial Morphogenesis" Nature 384:173-176 (Nov. 14, 1996).
Weidner et al., "Scatter Factor: Molecular Characteristics and Effect on the Invasiveness of Epithelial Cells" J Cell Biol 111(5 Pt 1):2097-2108 (Nov. 1990).
Wiesmann et al., "Crystal Structure at 1.7 A Resolution of VEGF in Complex with Domain 2 of the Flt-1 Receptor." Cell 91:695-704 (Nov. 28, 1997).
Wiesmann et al., "Crystal Structure of Nerve Growth Factor in Complex with the Ligand-Binding Domain of the TrkA Receptor" Nature 401:184-188 (Sep. 9, 1999).
Yamada et al., "Immunohistochemistry with Antibodies to Hepatocyte Growth Factor and its Receptor Protein (c-Met) in Human Brain Tissues" Brain Res 637(1-2):308-312 (Feb. 21, 1994).
Yansura et al., "Nucleotide sequence selection for increased expression of heterologous genes in *Escherichia coli*" Methods: A Companion to Methods in Enzymology 4(2):151-158 (1992).
Yelton et al., "Affinity maturation of the BR96 anti-carcinoma antibody by codon-based mutagenesis" J Immunol 155: 1994-2004 ( 1995).
Yu et al., "Exploratory Biomarker Analyses from a Placebo-controlled Phase II Study (OAM4558g) of MetMAb in Combination with Erlotinib in Patients with Advanced Non-Small-Cell Lung Cancer (NSCLC)" World Conference on Lung Cancer—14th, (Jul. 3, 2011).
Yu et al., "Exploratory biomarker analyses from OAM4558g: a placebo-controlled Phase II study of erlotinib + MetMAb in patients with advanced non-small-cell lung cancer (NSCLC)" (Abstract) American Society of Clinical Oncology 47th Annual Meeting, (Jun. 3, 2011).
Yu et al., "Exploratory biomarker analyses from OAM4558g: a placebo-controlled Phase II study of erlotinib + MetMAb in patients with advanced non-small-cell lung cancer (NSCLC)" (Poster 7529) American Society of Clinical Oncology 47th Annual Meeting, (Jun. 3, 2011).
Zhu et al., "Remodeling domain interfaces to enhance heterodimer formation" Protein Sci 6(4):781-788 (Apr. 1997).
Zola Monoclonal Antibodies: A Manual of Techniques "Chapter 6 using Monoclonal Antibodies: soluble Antigens" CRC Press,: 147-158 (1987).
Comoglio et al., (1992). "The Met/HGF Receptor" Positive Growth Control, Keystone Symposia on Molecular & Cellular Biology, Keystone, Colorado, Jan. 13-26, 1992, Journal of Cellular Biochemistry, 50: (Supplement 5168):192: Abstract No. H215 (Abstract Only), 8 pages total.

\* cited by examiner

5D5.v2 Light Chain

FR1-LC: DIQMTQSPSSLSASVGDRVTITC (SEQ ID NO:7)
FR2-LC: WYQQKPGKAPKLLIY (SEQ ID NO:8)
FR3-LC: GVPSRFSGSGSGTDFTLTISSLQPEDFATYYC (SEQ ID NO:9)
FR4-LC: FGQGTKVEIKR (SEQ ID NO:10)
HVR1-LC: KSSQSLLYTSSQKNYLA (SEQ ID NO:1)
HVR2-LC: WASTRES (SEQ ID NO:2)
HVR3-LC: QQYYAYPWT (SEQ ID NO:3)
CL1: TVAAPSVFIFPPSDEQLKSGTASVVCLLNNFYPREAKVQWKVDNALQSGNSQESVTEQDSKDSTYSLSSTLTLSKADYEK
HKVYACEVTHQGLSSPVTKSFNRGEC (SEQ ID NO:15)

5D5.v2 Heavy Chain

FR1-HC: EVQLVESGGGLVQPGGSLRLSCAAS (SEQ ID NO:11)
FR2-HC: WVRQAPGKGLEWV (SEQ ID NO:12)
FR3-HC: RFTISADTSKNTAYLQMNSLRAEDTAVYYC (SEQ ID NO:13)
FR4-HC: WGQGTLVTVSS (SEQ ID NO:14)
HVR1-HC: GYTFTSYWLH (SEQ ID NO:4)
HVR2-HC: GMIDPSNSDTRFNPNFKD (SEQ ID NO:5)
HVR3-HC: ATYRSYVTPLDY (SEQ ID NO:6)
CH1: ASTKGPSVFPLAPSSKSTSGGTAALGCLVKDYFPEPVTVSWNSGALTSGVHTFPAVLQSSGLYSLSSVVTVPSSSLGTQ
TYICNVNHKPSNTKVDKKVEPKSCDKTHT (SEQ ID NO:16)
Fc: CPPCPAPELLGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLWCLVKGFYPSDIAVEWESNG
QPENNYKTTPPVLDSDGSFFLYSKLTVDKSRWQQGNVFSCSVMHEALHNHYTQKSLSLSPGK (SEQ ID NO:17)

FIG. 2

CPPCPAPELLGGPSVFLFPPKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPREEMTKNQVSLWCLVKGFYPSDIAVEWESNGQPEN
NYKTTPPVLDSDGSFFLYSKLTVDKSRWQQGNVFSCSVMHEALHNHYTQKSLSLSPGK (SEQ ID NO:18)

FIG. 3

SEQUENCE LISTING

```
<160> NUMBER OF SEQ ID NOS: 34

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

```
Lys Ser Ser Gln Ser Leu Leu Tyr Thr Ser Ser Gln Lys Asn Tyr Leu
1               5                   10                  15

Ala

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Trp Ala Ser Thr Arg Glu Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Tyr Tyr Ala Tyr Pro Trp Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Ser Tyr Trp Leu His
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Met Ile Asp Pro Ser Asn Ser Asp Thr Arg Phe Asn Pro Asn Phe
1               5                   10                  15

Lys Asp

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Thr Tyr Arg Ser Tyr Val Thr Pro Leu Asp Tyr
1               5                   10
```

```
<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Tyr Gln Gln Lys Pro Gly Lys Ala Pro Lys Leu Leu Ile Tyr
1               5                   10                  15

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Gly Gln Gly Thr Lys Val Glu Ile Lys Arg
1               5                   10

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25
```

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Trp Val Arg Gln Ala Pro Gly Lys Gly Leu Glu Trp Val
1               5                   10

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Trp Gly Gln Gly Thr Leu Val Thr Val Ser Ser
1               5                   10

<210> SEQ ID NO 15
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 16
<211> LENGTH: 108

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr
            100                 105

<210> SEQ ID NO 17
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Ser Cys Ala Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Val Ser Lys Leu Thr Val Asp Lys Ser Arg Trp
            180                 185                 190

Gln Gln Gly Asn Val Phe Ser Cys Ser Val Met His Glu Ala Leu His
        195                 200                 205
```

```
Asn His Tyr Thr Gln Lys Ser Leu Ser Leu Ser Pro Gly Lys
    210                 215                 220

<210> SEQ ID NO 18
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45
```

```
Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Thr Tyr Arg Ser Tyr Val Thr Pro Leu Asp Tyr Trp Gly Gln Gly
            100                 105                 110

Thr Leu Val Thr Val Ser Ser
            115

<210> SEQ ID NO 20
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Leu Leu Tyr Thr
                20                  25                  30

Ser Ser Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Ala Tyr Pro Trp Thr Phe Gly Gln Gly Thr Lys Val Glu Ile
            100                 105                 110

Lys Arg

<210> SEQ ID NO 21
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Tyr
                20                  25                  30

Trp Leu His Trp Val Arg Gln Ala Pro Gly Lys Gly Leu Glu Trp Val
            35                  40                  45

Gly Met Ile Asp Pro Ser Asn Ser Asp Thr Arg Phe Asn Pro Asn Phe
 50                  55                  60

Lys Asp Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Thr Tyr Arg Ser Tyr Val Thr Pro Leu Asp Tyr Trp Gly Gln Gly
```

```
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Ser
        355                 360                 365
Cys Ala Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Val Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 22
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly
```

```
                1               5                   10                  15
            Asp Arg Val Thr Ile Thr Cys Lys Ser Ser Gln Ser Leu Leu Tyr Thr
                                20                  25                  30

Ser Ser Gln Lys Asn Tyr Leu Ala Trp Tyr Gln Gln Lys Pro Gly Lys
                                35                  40                  45

Ala Pro Lys Leu Leu Ile Tyr Trp Ala Ser Thr Arg Glu Ser Gly Val
                                50                  55                  60

Pro Ser Arg Phe Ser Gly Ser Gly Ser Gly Thr Asp Phe Thr Leu Thr
            65                  70                  75                  80

Ile Ser Ser Leu Gln Pro Glu Asp Phe Ala Thr Tyr Tyr Cys Gln Gln
                                85                  90                  95

Tyr Tyr Ala Tyr Pro Trp Thr Phe Gly Gln Gly Thr Lys Val Glu Ile
                                100                 105                 110

Lys Arg Thr Val Ala Ala Pro Ser Val Phe Ile Phe Pro Pro Ser Asp
                                115                 120                 125

Glu Gln Leu Lys Ser Gly Thr Ala Ser Val Val Cys Leu Leu Asn Asn
                                130                 135                 140

Phe Tyr Pro Arg Glu Ala Lys Val Gln Trp Lys Val Asp Asn Ala Leu
            145                 150                 155                 160

Gln Ser Gly Asn Ser Gln Glu Ser Val Thr Glu Gln Asp Ser Lys Asp
                                165                 170                 175

Ser Thr Tyr Ser Leu Ser Ser Thr Leu Thr Leu Ser Lys Ala Asp Tyr
                                180                 185                 190

Glu Lys His Lys Val Tyr Ala Cys Glu Val Thr His Gln Gly Leu Ser
                                195                 200                 205

Ser Pro Val Thr Lys Ser Phe Asn Arg Gly Glu Cys
                                210                 215                 220

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ser Ser Gln Ser Leu Leu Tyr Thr Ser Ser Gln Lys Asn Tyr Leu
1               5                   10                  15

Ala

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Ala Ser Thr Arg Glu Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 25

Gln Gln Tyr Tyr Ala Tyr Pro Trp Thr
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Tyr Thr Phe Thr Ser Tyr Trp Leu His
1               5                   10

<210> SEQ ID NO 27
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Met Ile Asp Pro Ser Asn Ser Asp Thr Arg Phe Asn Pro Asn Phe
1               5                   10                  15

Lys Asp

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Arg

<400> SEQUENCE: 28

Xaa Tyr Gly Ser Tyr Val Ser Pro Leu Asp Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Thr Tyr Gly Ser Tyr Val Ser Pro Leu Asp Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Ser Tyr Gly Ser Tyr Val Ser Pro Leu Asp Tyr
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Asp Ala Gln Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Leu Thr Glu Lys Arg Lys Lys Arg Ser
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Pro Asp Ser Ala Glu Pro Met
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Asn Val Arg Cys Leu Gln His Phe
1               5
```

ANTI-C-MET-ANTIBODY FORMULATIONS

CROSS REFERENCE TO RELATED APPLICATIONS

This application is a continuation of U.S. application Ser. No. 13/538,901, filed Jun. 29, 2012 which claims benefit of priority to U.S. Patent Application 61/503,513, filed Jun. 30, 2011, the entire contents of which is incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Nov. 5, 2014, is named P4690R1C1US_SequenceListing.TXT and is 21,849 bytes in size.

TECHNICAL FIELD

Provided herein are pharmaceutical formulations comprising an anti-c-met antibody and uses of the same.

BACKGROUND

Excipients are added to pharmaceutical formulations to aid in the stabilization of the active compound. The compatibility of the excipients with the active compound is crucial for the quality and stability of the pharmaceutical formulation. While excipients are important in the stabilization of the active compound, excipients can cause problems: the excipient may degrade and thus lose its mechanism of stabilization or it may produce degradants that interact with the active compound.

Pharmaceutical formulations in which the active compound is a polypeptide, e.g. an antibody, can pose special problems as polypeptides generally are larger and more complex than traditional organic and inorganic molecules (for example, polypeptides possess multiple functional groups, in addition to complex three-dimensional structures). In addition, for a polypeptide to remain biologically active, the pharmaceutical polypeptide formulation must preserve intact the conformational integrity of at least a core sequence of the polypeptide's amino acids, while at the same time maintaining physical and chemical stability of the pharmaceutical polypeptide formulation. Excipients are generally stable in aqueous solution; however, excipients in a pharmaceutical polypeptide formulation can interact with the polypeptide to undergo degradation in a formulation and can prevent the stabilization of the protein or the degradants could interact with the polypeptide to pose challenges (such as a loss in activity). Therefore, the evaluation of the interaction of the non-active components of the pharmaceutical formulation and polypeptide active agent is crucial for ensuring chemical and physical stability.

Polysorbates are non-ionic surfactants used to stabilize an active compound against interface induced aggregation and surface adsorption. Polysorbates can be effective against various stresses such as agitation (for example, shaking or stirring), freeze/thawing, and lyophilization. In pharmaceutical polypeptide formulations, polysorbates minimize adsorption to surfaces and reduce the air-liquid interfacial surface tension and thus the rate of protein denaturation. Loss of polysorbate in the pharmaceutical formulation can result in instability of the formulation. Further, polysorbates can be degraded by oxidation and hydrolysis which can lead to a decrease in the apparent concentration of polysorbate in the pharmaceutical formulation over long shelf life. Polysorbates (e.g., polysorbate 20) can be cleaved to produce degradants (e.g., free lauric acid and sorbitan polyoxyethylene side chain). These polysorbate degradants are less surface-active than nondegraded polysorbate and hence the chemical and physical stability of the pharmaceutical formulation may be compromised. Further, some polysorbate degradants are insoluble and may form particles if they are not solubilized by intact polysorbate, i.e., if the ratio of degraded polysorbate 20:intact polysorbate 20 is too high.

The rate and extent of degradation of polysorbate is influenced by the chemical and physical properties of the active compound, and the stabilizing ability of polysorbate can vary between different pharmaceutical formulations comprising different active compounds. Particularly since polysorbates are included in protein formulations to stabilize the protein, the decrease in the concentration of polysorbate and the accumulation of degradant molecules in a pharmaceutical polypeptide formulation is of potential concern for protein stability.

Numerous molecules targeted at the HGF/c-met pathway have been reported. These molecules include a portion of the extracellular domain of c-met and anti-c-met antibodies such as those described in U.S. Pat. No. 5,686,292, Martens, T. et al., *Clin. Cancer Res.* 12 (20 Pt. 1):6144 (2006); U.S. Pat. No. 6,468,529; WO2006/015371; WO2007/063816, and WO2010/045345. Bivalent forms of anti-c-met antibodies have been shown to promote dimerization and lead to activation of c-met (agonistic function), while conversely monovalent antibodies have been shown to inhibit c-met activity (antagonistic function). For treatment of pathological conditions requiring an antagonistic function, bivalency of an anti-c-met antibody could result in an undesirable agonistic effect, and therefore, the monovalent trait is required to ensure an antagonistic activity upon binding of the anti-c-met antibody to the target for treatment of the pathological condition. Fab fragments and one-armed antibodies are examples of monovalent antibodies. One-armed antibodies generally have a longer half-life than Fabs. However, as a one-armed antibody comprises a single light chain and a single heavy chain (as well as an additional Fc region), if the one-armed antibody structure is not stabilized, the polypeptides could potentially form a bivalent antibody with two heavy chain and two light chains. Aggregation of monovalent antibodies (formation of multimer and oligomers) and/or failure to maintain monovalent structure in a pharmaceutical formulation comprising anti-c-met antibodies could lead to an undesirable agonistic effect. Minimization of anti-c-met antibody aggregation in the pharmaceutical formulation is thus particularly important. Therefore, despite the significant advancement in the molecules which target the HGF/c-met pathway, stable pharmaceutical formulations, which minimize aggregation of c-met antibodies, are still needed.

All references cited herein, including patent applications and publications, are incorporated by reference in their entirety.

DISCLOSURE OF THE INVENTION

Provided herein are pharmaceutical formulations comprising an anti-c-met antibody. In some embodiments, the pharmaceutical formulation is a liquid pharmaceutical formulation. In some embodiments, the pharmaceutical formulation is a stable pharmaceutical formulation. In some embodiments, the pharmaceutical formulation is a stable liquid pharmaceutical formulation. In some embodiments, the anti-c-met antibody is an antagonist anti-c-met antibody.

For example, provided herein are pharmaceutical formulations comprising: (a) an anti-c-met antibody; (b) a histidine buffer at pH 5.0-5.4; (c) a saccharide; and (d) a polysorbate, wherein the polysorbate is present at greater than 0.02% w/v.

In some embodiments of any of the formulations, the anti-c-met antibody comprising a HVR-L 1 comprising sequence KSSQSLLYTSSQKNYLA (SEQ ID NO:1), a HVR-L2 comprising sequence WASTRES (SEQ ID NO:2), a HVR-L3 comprising sequence QQYYAYPWT (SEQ ID NO:3), a HVR-H1 comprising sequence GYTFTSYWLH (SEQ ID NO:4), a HVR-H2 comprising sequence GMIDPSNSDTRFNPNFKD (SEQ ID NO:5), and a HVR-H3 comprising sequence ATYRSYVTPLDY (SEQ ID NO:6). In some embodiments, the anti-c-met antibody comprises (a) a heavy chain variable domain comprising the sequence: EVQLVESGGGLVQPGGSLRLSCAASGYTFT-SYWLHWVRQAPGKGLEWVGMIDPSNSDTRF NPN-FKDRFTISADTSKNTAYLQMNSLRAEDTAVYY-CATYRSYVTPLDYWGQGTLVTVSS (SEQ ID NO:19) and (b) a light chain variable domain comprising the sequence: DIQMTQSPSSLSAS-VGDRVTITCKSSQSLLYTSSQKNYLAWYQQKPGKAP-KLLIYWASTR ESGVPSRFSGSGSGTDFTLTISSLQPED-FATYYCQQYYAYPWTFGQGTKVEIKR (SEQ ID NO:20). In some embodiments, the anti-c-met antibody comprises a single antigen binding arm and comprises a Fc region, wherein the Fc region comprises a first and a second Fc polypeptide, and wherein the first and second Fc polypeptides are present in a complex. In some embodiments, the first and second Fc polypeptides form a Fc region that increases stability of said antibody fragment compared to a Fab molecule comprising said antigen binding arm. In some embodiments, the anti-c-met antibody comprises (a) a first polypeptide comprising the amino acid sequence of SEQ ID NO:19, a CH1 sequence, and a first Fc polypeptide and (b) a second polypeptide comprising the amino acid sequence of SEQ ID NO:20 and CL1 sequence. In some embodiments, the anti-c-met antibody further comprises (c) a third polypeptide comprising a second Fc polypeptide. In some embodiments, the first Fc polypeptide comprises the Fc sequence depicted in FIG. 2 (SEQ ID NO: 17) and the second Fc polypeptide comprises the Fc sequence depicted in FIG. 3 (SEQ ID NO: 18). In some embodiments, the anti-c-met antibody is onartuzumab. In some embodiments, the anti-c-met antibody binds the same epitope as onartuzumab.

In some embodiments of any of the formulations, the anti-c-met antibody is present at a concentration between about 10 mg/mL and about 100 mg/mL (e.g. about 15 mg/mL and about 75 mg/mL). In some embodiments, the anti-c-met antibody is present at a concentration of about 60 mg/mL.

In some embodiments of any of the formulations, the saccharide is present at a concentration of about 75 mM to about 200 mM (e.g., about 100 mM to about 150 mM). In some embodiments, the saccharide is present at a concentration of about 120 mM. In some embodiments, the saccharide is a disaccharide. In some embodiments, the disaccharide is trehalose. In some embodiments, the disaccharide is sucrose.

In some embodiments of any of the formulations, the histidine buffer is at a concentration of about 1 mM to about 50 mM (e.g. about 1 mM to about 25 mM). In some embodiments, the histidine buffer is at a concentration of about 10 mM. In some embodiments, the histidine buffer is histidine acetate.

In some embodiments of any of the formulations, the polysorbate is present at a concentration greater than 0.02% and less than about 0.1%. In some embodiments, the polysorbate is present at a concentration of about 0.04%. In some embodiments, the polysorbate is polysorbate 20.

In some embodiments of any of the formulations, the formulation is diluted with a diluent (e.g., 0.9% NaCl). In some embodiments, the anti-c-met antibody is present at a concentration of about 1 mg/mL.

Provided herein are methods of inhibiting c-met activated cell proliferation, said method comprising contacting a cell or tissue with an effective amount of the pharmaceutical formulation described herein (e.g., upon dilution).

Also provided herein are methods of modulating a disease associated with dysregulation of the HGF/c-met signaling axis, said method comprising administering to a subject an effective amount of the pharmaceutical formulation described herein (e.g., upon dilution).

Further provided are methods of treating a subject having a proliferative disorder, said method comprising administering to the subject an effective amount of the pharmaceutical formulation described herein (e.g., upon dilution). In some embodiments, the proliferative disorder is cancer. In some embodiments, the cancer is lung cancer (non-small cell lung cancer (NSCLC)), glioblastoma, pancreatic cancer, sarcoma, renal cell carcinoma, hepatocellular carcinoma, gastric cancer, colorectal cancer, and/or breast cancer. In some embodiments, the methods further comprise a second therapeutic agent.

Provided are methods of making the pharmaceutical formulation described herein.

In addition, provided herein are articles of manufacture comprising a container with a pharmaceutical formulation described herein (e.g., upon dilution) contained therein. Provided herein are also methods of making the articles of manufacture comprising a pharmaceutical formulation described herein (e.g., upon dilution).

DESCRIPTION OF THE DRAWINGS

FIG. 2 depicts amino acid sequences of the framework (FR), hypervariable region (HVR), first constant domain (CL or CH1) and Fc region (Fc) of MetMAb (onartuzumab or OA5D5.v2). The Fc sequence depicted comprises "hole" (cavity) mutations T366S, L368A and Y407V, as described in WO 2005/063816.

FIG. 3 depicts sequence of an Fc polypeptide comprising "knob" (protuberance) mutation T366W, as described in WO 2005/063816. In some embodiments, an Fc polypeptide comprising this sequence forms a complex with an Fc polypeptide comprising the Fc sequence of FIG. 1 to generate an Fc region. The sequence disclosed in FIG. 3 represents residues 6-227 of SEQ ID NO: 18.

Figure 6:
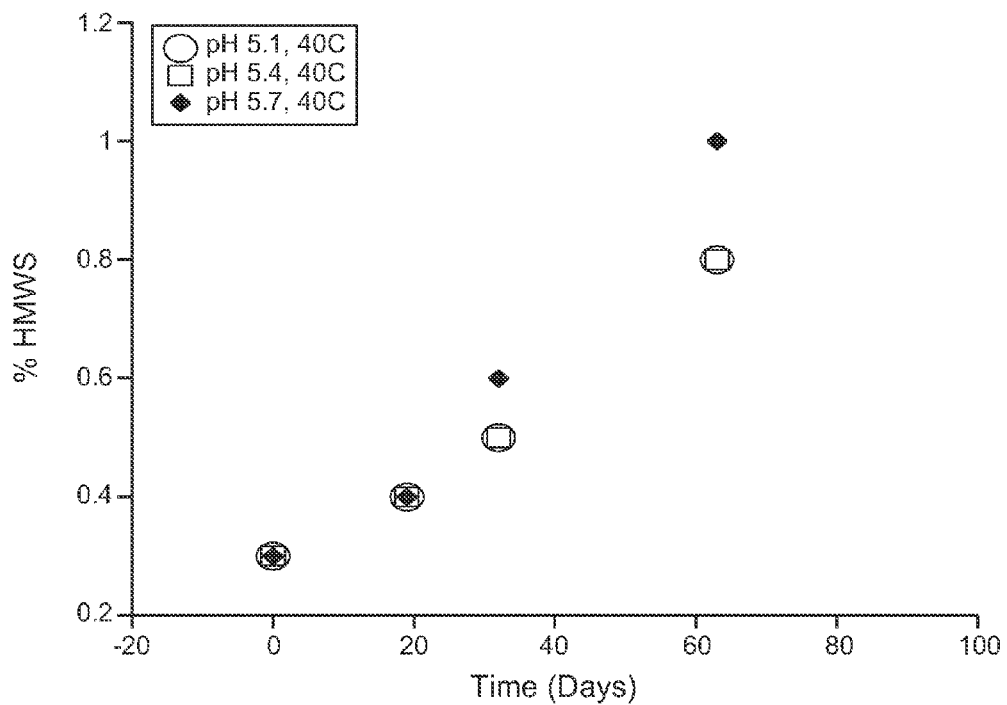

FIG. 6 depicts the rate of aggregate formation as indicated by the percentage of high molecular weight species (HMWS) over time (days) at 40° C. for formulations of 40 mg/mL onartuzumab, 10 mM histidine acetate, 120 mM trehalose, and 0.02% polysorbate 20 at pH 5.1, 5.4, and 5.7.

Figure 7:
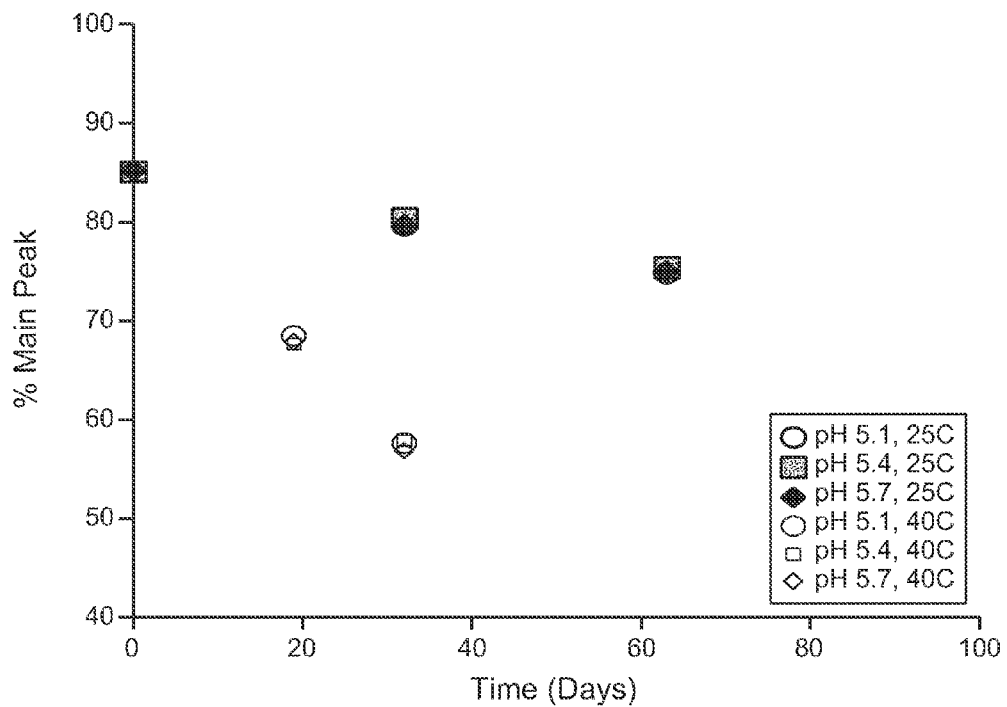

FIG. 7 depicts the chemical stability as measured by ion-exchange chromatography (IEC) as indicated by the percent main peak over time (days) at 25° C. and 40° C. for formulations of 40 mg/mL onartuzumab, 10 mM histidine acetate, 120 mM trehalose, and 0.02% polysorbate 20 at pH 5.1, 5.4, and 5.7.

Figure 8:
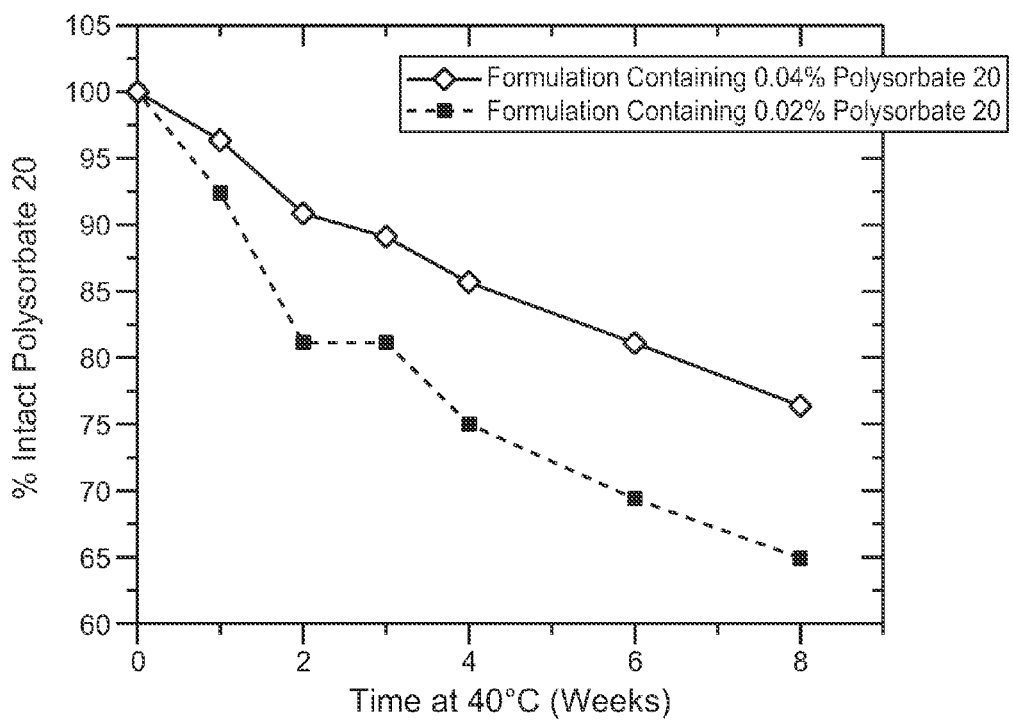

FIG. 8 depicts the percentage of intact polysorbate over time (weeks) at 40° C. for formulations of 60 mg/mL onartuzumab, 10 mM histidine acetate, pH 5.4, and 120 mM sucrose with 0.02% polysorbate 20 or 0.04% polysorbate 20.

Figure 9:
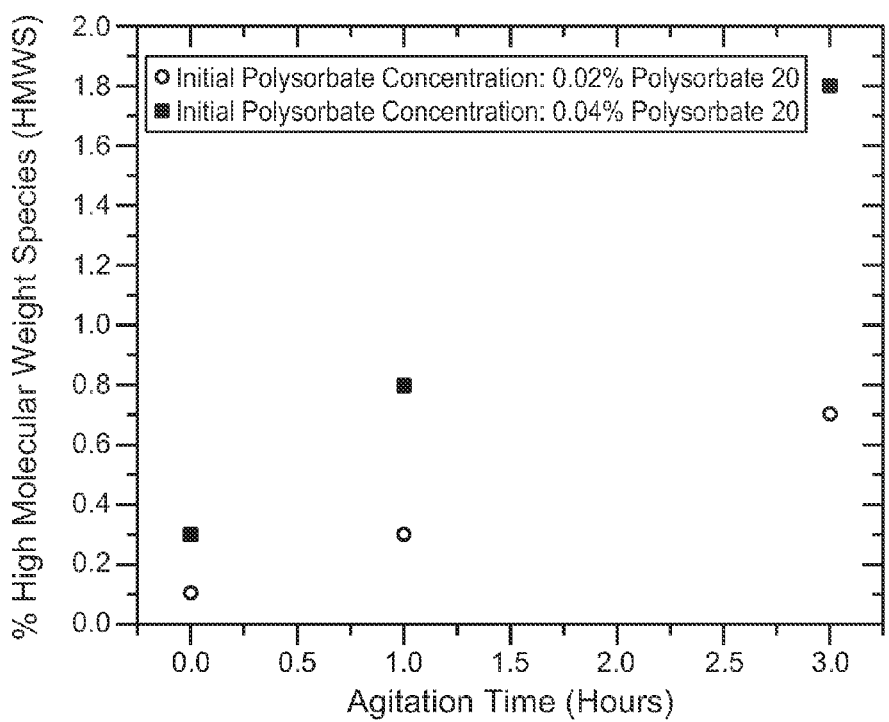

FIG. 9 depicts the rate of aggregate formation of onartuzumab diluted to 1 mg/mL in IV bags containing 0.9% NaCl. The rate of aggregation is indicated by the percentage of high molecular weight species (HMWS) over time (hours) of agitation for diluted formulations of (a) 60 mg/mL onartuzumab, 10 mM histidine acetate, 120 mM trehalose, and 0.02% polysorbate 20 at pH 5.4 kept at room temperature as shown by squares and (b) 60 mg/mL onartuzumab, 10 mM histidine acetate, 120 mM sucrose, and 0.04% polysorbate 20 at pH 5.4 kept at 30° C. as shown by circles.

DETAILED DESCRIPTION

Provided herein are stable pharmaceutical formulations comprising an anti-c-met antibody. In some embodiments, the anti-c-met antibody is an antagonist anti-c-met antibody. In some embodiments, the anti-c-met antibody is a monovalent anti-c-met antibody. In addition, kits and articles of manufacture comprising the anti-c-met antibody pharmaceutical formulations and uses of the anti-c-met antibody pharmaceutical formulations are provided.

I. DEFINITIONS

The term "pharmaceutical formulation" refers to preparations which are in such form as to permit the biological activity of the active compound(s) to be effective, and which contain no additional components which are toxic to the subjects to which the formulation is administered. "Pharmaceutically acceptable" excipients (vehicles, additives) are those which can reasonably be administered to a subject to provide an effective dose of the active compound.

A "stable" formulation is one in which the polypeptide therein essentially retains its physical stability and/or chemical stability and/or biological activity upon storage and/or during administration (e.g., after dilution in an IV bag). Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected temperature for a selected time period.

A polypeptide "retains its physical stability" in a pharmaceutical formulation if the chemical stability at a given time is such that the protein is considered to still retain its biological activity and an acceptable safe profile, for example, as determined by International Conference on Harmonisation of Technical Requirements for Registration of Pharmaceuticals for Human Use Guidelines (e.g., commercially acceptable levels of aggregation, precipitation and/or denaturation, for example, upon visual examination of color and/or clarity or as measured by UV light scattering or by size exclusion chromatography).

A polypeptide "retains its chemical stability" in a pharmaceutical formulation, if the chemical stability at a given time is such that the protein is considered to still retain its biological activity. Chemical stability can be assessed by detecting and quantifying chemically altered forms of the protein. Chemical alteration may involve size modification (e.g., clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration which can be evaluated by ion-exchange chromatography, for example.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "histidine buffer" is a buffer comprising histidine ions.

A "saccharide" herein comprises the general composition $(CH_2O)_n$ and derivatives thereof.

An "anti-c-met antibody" and "an antibody that binds to c-met" refer to an antibody that is capable of binding c-met with sufficient affinity such that the antibody is useful as a diagnostic and/or therapeutic agent in targeting c-met. In some embodiments, the extent of binding of an anti-c-met antibody to an unrelated, non-c-met protein is less than about 10% of the binding of the antibody to c-met as measured, e.g., by a radioimmunoassay (RIA). In some embodiments, an antibody that binds to c-met has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g. from $10^{-8}$ M to $10^{-13}$ M, e.g., from $10^{-9}$ M to $10^{-13}$ M). In some embodiments, an anti-c-met antibody binds to an epitope of c-met that is conserved among c-met from different species.

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region as defined herein.

A "blocking" antibody or an "antagonist" antibody is one which significantly inhibits (either partially or completely) a biological activity of the antigen it binds.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The phrase "N-terminally truncated heavy chain", as used herein, refers to a polypeptide comprising parts but not all of a full length immunoglobulin heavy chain, wherein the missing parts are those normally located on the N terminal region of the heavy chain. Missing parts may include, but are not limited to, the variable domain, CH1, and part or all of a hinge sequence. Generally, if the wild type hinge sequence is not present, the remaining constant domain(s) in the N-terminally truncated heavy chain would comprise a component that is capable of linkage to another Fc sequence (i.e., the "first" Fc polypeptide as described herein). For example, said component can be a modified residue or an added cysteine residue capable of forming a disulfide linkage.

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain may vary, the human IgG heavy chain Fc sequence is usually defined to stretch from an amino acid residue at about position Cys226, or from about position Pro230, to the carboxyl-terminus of the Fc sequence. However, the C-terminal lysine (Lys447) of the Fc sequence may or may not be present. The Fc sequence of an immunoglobulin generally comprises two constant domains, a CH2 domain and a CH3 domain, and optionally comprises a CH4 domain. By "Fc polypeptide" herein is meant one of the polypeptides that make up an Fc region. An Fc polypeptide may be obtained from any suitable immunoglobulin, such as IgG1, IgG2, IgG3, or IgG4 subtypes, IgA, IgE, IgD or IgM. In some embodiments, an Fc polypeptide comprises part or all of a wild type hinge sequence (generally at its N terminus). In some embodiments, an Fc polypeptide does not comprise a functional or wild type hinge sequence.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991);

Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

The "hinge region," "hinge sequence", and variations thereof, as used herein, includes the meaning known in the art, which is illustrated in, for example, Janeway et al., Immuno Biology: the immune system in health and disease, (Elsevier Science Ltd., NY) (4th ed., 1999); Bloom et al., *Protein Science* (1997), 6:407-415; Humphreys et al., J. Immunol. Methods (1997), 209:193-202.

Unless indicated otherwise, the expression "multivalent antibody" is used throughout this specification to denote an antibody comprising three or more antigen binding sites. The multivalent antibody is preferably engineered to have the three or more antigen binding sites and is generally not a native sequence IgM or IgA antibody.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three HVRs of each variable domain interact to define an antigen binding site on the surface of the $V_H$-$V_L$ dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

The phrase "antigen binding arm", as used herein, refers to a component part of an antibody fragment that has an ability to specifically bind a target molecule of interest. Generally and preferably, the antigen binding arm is a complex of immunoglobulin polypeptide sequences, e.g., HVR and/or variable domain sequences of an immunoglobulin light and heavy chain.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The expression "linear antibodies" refers to the antibodies described in Zapata et al., *Protein Eng.*, 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more HVRs, compared to a parent antibody which does not possess such alterations, such alterations resulting in an improvement in the affinity of the antibody for antigen.

An antibody having a "biological characteristic" of a designated antibody is one which possesses one or more of the biological characteristics of that antibody which distinguish it from other antibodies that bind to the same antigen.

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For the multimeric antibodies herein, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1\times10^{-7}$ M, preferably no more than about $1\times10^{-8}$ M and most preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above. In some embodiments, the species-dependent antibody is a humanized or human antibody.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

The term "substantially similar" or "substantially the same," as used herein, refers to a sufficiently high degree of similarity between two numeric values (for example, one associated with an antibody and the other associated with a reference/comparator antibody), such that one of skill in the art would consider the difference between the two values to be of little or no biological and/or statistical significance within the context of the biological characteristic measured by said values (e.g., Kd values).

The phrase "substantially reduced" or "substantially different," as used herein, refers to a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values).

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment with a substance/molecule or method described herein. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all pre-cancerous and cancerous cells and tissues. The terms "cancer", "cancerous," "cell proliferative disorder," "proliferative disorder," and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer. In some embodiments, the cancer is triple-negative (ER-, PR-, HER2-) cancer. In some embodiments, the cancer is triple-negative metastatic breast cancer, including any histologically confirmed triple-negative (ER-, PR-, HER2-) adenocarcinoma of the breast with locally recurrent or metastatic disease, e.g., where the locally recurrent disease is not amenable to resection with curative intent.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies are used to delay development of a disease or to slow the progression of a disease.

An "effective amount" of an agent, e.g., a pharmaceutical formulation, refers to an amount effective, at dosages and for periods of time necessary, to achieve the desired therapeutic or prophylactic result.

A "therapeutically effective amount" refers to an amount of a therapeutic agent to treat or prevent a disease or disorder in a mammal. In the case of cancers, the therapeutically effective amount of the therapeutic agent may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the drug may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets PDGFR-beta, BlyS, APRIL, BCMA receptor(s), TRAIL/Apo2, and other bioactive and organic chemical agents, etc. Combinations thereof are also included.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), pegylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use include, but are not limited to, those chemotherapeutic agents described above.

A "growth inhibitory agent" when used herein refers to a compound or composition which inhibits growth of a cell (e.g., a cell whose growth is dependent upon HGF/c-met activation either in vitro or in vivo). Thus, the growth inhibitory agent may be one which significantly reduces the percentage of HGF/c-met-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

The term "concurrently" is used herein to refer to administration of two or more therapeutic agents, where at least part of the administration overlaps in time. Accordingly, concurrent administration includes a dosing regimen when the administration of one or more agent(s) continues after discontinuing the administration of one or more other agent(s).

By "reduce or inhibit" is meant the ability to cause an overall decrease of 20%, 30%, 40%, 50%, 60%, 70%, 75%, 80%, 85%, 90%, 95%, or greater. Reduce or inhibit can refer to the symptoms of the disorder being treated, the presence or size of metastases, or the size of the primary tumor.

The term "package insert" is used to refer to instructions customarily included in commercial packages of therapeutic products, that contain information about the indications, usage, dosage, administration, combination therapy, contraindications and/or warnings concerning the use of such therapeutic products.

It is understood that aspect and embodiments of the invention described herein include "consisting" and/or "consisting essentially of" aspects and embodiments.

As used herein, the singular form "a", "an", and "the" includes plural references unless indicated otherwise.

As is understood by one skilled in the art, reference to "about" a value or parameter herein includes (and describes) embodiments that are directed to that value or parameter per se. For example, description referring to "about X" includes description of "X".

II. PHARMACEUTICAL FORMULATIONS

Provided herein are pharmaceutical formulations comprising an anti-c-met antibody. In some embodiments, the pharmaceutical formulation is a liquid pharmaceutical formulation. In some embodiments, the pharmaceutical formulation is a stable pharmaceutical formulation. In some embodiments, the pharmaceutical formulation is a stable liquid pharmaceutical formulation. In some embodiments, the anti-c-met antibody is an antagonist anti-c-met antibody. In some embodiments, the anti-c-met antibody is a monovalent anti-c-met antibody. Minimization in the pharmaceutical formulation of anti-c-met antibody aggregation is particularly important. Bivalent forms of anti-c-met antibodies have been shown to promote dimerization and lead to activation of c-met (agonistic function), while conversely monovalent antibodies inhibit c-met activity (antagonistic function). Aggregation of monovalent antibodies (formation of multimer and oligomers) and/or failure to maintain monovalent structure in a pharmaceutical formulation comprising anti-c-met antibodies could lead to an undesirable agonistic effect.

In particular, provided herein are pharmaceutical formulations comprising (a) an anti-c-met antibody and (b) a polysorbate, wherein the polysorbate concentration is greater than 0.02% w/v. In some embodiments, the pharmaceutical formulation comprises (a) an anti-c-met antibody; (b) a polysorbate, wherein the polysorbate concentration is greater than 0.02% w/v; and (c) a histidine buffer (e.g., a histidine buffer at a pH between 5.0 and 5.4). In some embodiments, the pharmaceutical formulation comprises (a) an anti-c-met antibody; (b) a histidine buffer at pH 5.0-5.4; (c) a saccharide; and (d) a polysorbate, wherein the polysorbate concentration is greater than 0.02% w/v. In some embodiments, the pharmaceutical formulation is a liquid pharmaceutical formulation. In some embodiments, the pharmaceutical formulation is a stable pharmaceutical formulation. In some embodiments, the pharmaceutical formulation is a stable liquid pharmaceutical formulation.

Anti-c-met antibodies useful in the pharmaceutical formulations are described in Section III. In some embodiments, the anti-c-met antibody is an antagonist anti-c-met antibody. In some embodiments, the anti-c-met antibody is a monovalent anti-c-met antibody. For example, in some embodiments, the anti-c-met antibody comprises a single antigen binding arm. In some embodiments, the anti-c-met antibody comprises a single antigen binding arm and comprises a Fc region, wherein the Fc region comprises a first and a second Fc polypeptide, wherein the first and second Fc polypeptides are present in a complex. In some embodiments, the first and second Fc polypeptides form a Fc region that increases stability of said antibody fragment compared to a Fab molecule comprising said antigen binding arm. In some embodiments, the anti-c-met antibody comprises a HVR-L1 comprising the amino acid sequence of SEQ ID NO:1, a HVR-L2 comprising the amino acid sequence of SEQ ID NO:2, a HVR-L3 comprising the amino acid sequence of SEQ ID NO:3, a HVR-H1 comprising the amino acid sequence of SEQ ID NO:4, a HVR-H2 comprising the amino acid sequence of SEQ ID NO:5, and a HVR-H3 comprising the amino acid sequence of SEQ ID NO:6. In some embodiments, the anti-c-met antibody comprises (a) a heavy chain variable domain comprising the amino acid sequence of SEQ ID NO:19 and (b) a light chain variable domain comprising the amino acid sequence of SEQ ID NO:20. In some embodiments, the anti-c-met antibody comprises (a) a first polypeptide comprising the amino acid sequence of SEQ ID NO:19, a CH1 sequence, and a first Fc polypeptide, (b) a second polypeptide comprising the amino acid sequence of SEQ ID NO:20 and CL1 sequence, and (c) a third polypeptide comprising a second Fc polypeptide. In some embodiments, the first Fc polypeptide comprises the Fc sequence depicted in FIG. 2 (SEQ ID NO: 17) and the second Fc polypeptide comprises the Fc sequence depicted in FIG. 3 (SEQ ID NO: 18). In some embodiments, the anti-c-met antibody is onartuzumab.

In some embodiments of any of the pharmaceutical formulations described herein, the anti-c-met antibody of the pharmaceutical formulation is present at a concentration between about 10 mg/mL and about 100 mg/mL. In some embodiments, the concentration of the anti-c-met antibody (e.g., onartuzumab) is between about any of 10 mg/mL to 50 mg/mL, 10 mg/mL to 75 mg/mL, 25 mg/mL to 75 mg/mL, 50 mg/mL to 100 mg/mL, 50 mg/mL to 75 mg/mL, and/or 75 mg/mL to 100 mg/mL. In some embodiments, the concentration of the anti-c-met antibody (e.g., onartuzumab) is greater than about any of 20 mg/mL, 30 mg/mL, 40 mg/mL, 50 mg/mL, 60 mg/mL, 70 mg/mL, or 100 mg/mL. For example, in some embodiments, the pharmaceutical formulation comprises (a) an anti-c-met antibody (e.g., onartuzumab), wherein the anti-c-met antibody is present at a concentration between about 50 mg/mL and about 75 mg/mL; (b) a histidine buffer at pH 5.0-5.4; (c) a saccharide; and (d) a polysorbate, wherein the polysorbate concentration is greater than 0.02% w/v. In some embodiments, the concentration of the anti-c-met antibody (e.g., onartuzumab) is less than about any of 150 mg/mL, 125 mg/mL, 100 mg/mL, or 75 mg/mL. In some embodiments, the concentration of the anti-c-met antibody (e.g., onartuzumab) is about any of 20 mg/mL, 30 mg/mL, 40 mg/mL, 50 mg/mL, 60 mg/mL, 70 mg/mL, or 80 mg/mL. In some embodiments, the concentration of the anti-c-met antibody (e.g., onartuzumab) is about 60 mg/mL.

The pharmaceutical formulation preferably comprises a polysorbate. The polysorbate is generally included in an amount which reduces aggregate formation (such as that which occurs upon shaking or shipping). Examples of polysorbate include, but are not limited to, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and/or polysorbate 80 (polyoxyethylene (20) sorbitan monooleate). In some embodiments, the polysorbate is polysorbate 20 (polyoxyethylene (20) sorbitan monolaurate). In some embodiments of any of the pharmaceutical formulations described herein, the polysorbate concentration is sufficient to minimize aggregation and/or maintain stability upon long term storage and/or during administration (e.g., after dilution in an IV bag). In some embodiments, the polysorbate concentration is greater than 0.02% w/v, greater than or equal to about 0.03% w/v, or greater than or equal to about 0.04% w/v. In some embodiments, the polysorbate concentration is greater than 0.02% w/v and less than about 0.1% w/v. In some embodiments, the polysorbate concentration is greater than 0.03% w/v and less than about 0.1% w/v. In some embodiments, the polysorbate concentration is about any of 0.03% w/v, 0.04% w/v, or 0.05% w/v. In some embodiments, the polysorbate is present at a concentration of about 0.04% w/v. For example, in some embodiments, the pharmaceutical formulation comprises (a) an anti-c-met antibody (e.g., onartuzumab); (b) a histidine buffer at pH 5.0-5.4; (c) saccharide; and (d) polysorbate 20, wherein the polysorbate 20 concentration is about 0.04% w/v.

The pharmaceutical formulation preferably comprises a saccharide. Saccharides include monosaccharides, disaccharides, trisaccharides, polysaccharides, sugar alcohols, reducing sugars, nonreducing sugars, etc. Further examples of saccharides include, but are not limited to, glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. In some embodiments, the saccharide is a disaccharide. In some embodiments, the saccharide is a nonreducing disaccharide. In some embodiments, the saccharide is trehalose. In some embodiments, the saccharide is sucrose. For example, in some embodiments, the pharmaceutical formulation comprises (a) an anti-c-met antibody (e.g., onartuzumab); (b) a histidine buffer at pH 5.0-5.4; (c) sucrose; and (d) a polysorbate, wherein the polysorbate concentration is greater than 0.02% w/v.

The saccharide is generally included in an amount which reduces aggregate formation. In some embodiments of any of the pharmaceutical formulations described herein, the saccharide is present at a concentration of between about any of 50 mM to 250 mM, 75 mM to 200 mM, 75 mM to 150 mM, 100 mM to 150 mM, or 110 mM to 130 mM. In some embodiments, the saccharide is present at a concentration greater than about any of 50 mM, 75 mM, 100 mM, 110 mM, or 115 mM. In some embodiments, the saccharide is present at a concentration of about any of 100 mM, 110 mM, 120 mM, 130 mM, or 140 mM. In some embodiments, the saccharide is present at a concentration of about 120 mM. For example, in some embodiments, the pharmaceutical formulation comprises (a) an anti-c-met antibody (e.g., onartuzumab); (b) a histidine buffer at pH 5.0-5.4; (c) sucrose, wherein the sucrose is present at a concentration of about 120 mM; and (d) a polysorbate, wherein the polysorbate concentration is greater than 0.02% w/v.

The pharmaceutical formulation preferably comprises a histidine buffer. Examples of histidine buffers include, but are not limited to, histidine chloride, histidine succinate, histidine acetate, histidine phosphate, histidine sulfate. In some embodiments, the histidine buffer is histidine acetate. In some embodiments of any of the pharmaceutical formulations described herein, the histidine buffer concentration is between about any of 1 mM to 50 mM, 1 mM to 35 mM, 1 mM to 25 mM, 1 mM to 20 mM, 7.5 mM to 12.5 mM, or 5 mM to 15 mM. In some embodiments, the histidine buffer concentration is greater than or equal to about any of 5 mM, 7.5 mM, or 10 mM. In some embodiments, the histidine buffer concentration is about any of 5 mM, 7.5 mM, 10 mM, 12.5 mM, or 15 mM. In some embodiments, the histidine buffer concentration is about 10 mM. In some embodiments of any of the pharmaceutical formulations described herein, the histidine buffer is at a pH of between pH 5.0 and 5.4, for example, about any of pH 5.0, pH 5.1, pH 5.2, pH 5.3, or pH 5.4. In some embodiments, the pH is between pH 5.1 and 5.4. For example, in some embodiments, the pharmaceutical formulation comprises (a) an anti-c-met antibody (e.g., onartuzumab); (b) a histidine acetate buffer at pH 5.4, wherein the histidine acetate buffer is at a concentration of about 10 mM; (c) saccharide; and (d) a polysorbate, wherein the polysorbate concentration is greater than 0.02% w/v.

In some embodiments, the pharmaceutical formulation comprises (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v. In some embodiments, the pharmaceutical formulation comprises (a) an anti-c-met antibody (e.g., onartuzumab), wherein the anti-c-met antibody is present at a concentration of about 60 mg/mL; (b) a histidine acetate buffer at pH 5.4, wherein the histidine acetate buffer is at a concentration of about 10 mM; (c) sucrose, wherein the sucrose is at a concentration of about 120 mM; and (d) polysorbate 20, wherein the polysorbate 20 concentration is about 0.04% w/v.

The pharmaceutical formulation herein may also contain more than one active compound as necessary for the particular indication being treated, preferably those with complementary activities that do not adversely affect each other. Such molecules are suitably present in combination in amounts that are effective for the purpose intended.

Further, provided herein are vials and methods of filing a vial comprising a pharmaceutical formulation described herein. In some embodiments, the pharmaceutical formulation is provided inside a vial with a stopper pierceable by a syringe, preferably in aqueous form. The vial is desirably stored at about 2-8° C. as well as up to 30° C. for 24 hours until it is administered to a subject in need thereof. The vial may for example be a 15 cc vial (for example for a 600 mg dose) or 20 cc vial (for example for a 900 mg dose).

The pharmaceutical formulation for administration is preferably a liquid formulation (not lyophilized) and has not been subjected to prior lyophilization. While the pharmaceutical formulation may be lyophilized, preferably it is not. In some embodiments of any of the pharmaceutical formulations, the pharmaceutical formulation, the pharmaceutical formulation is a lyophilized pharmaceutical formulation. In some embodiments, the pharmaceutical formulation is a liquid formulation. In some embodiments, the pharmaceutical formulation does not contain a tonicifying amount of a salt such as sodium chloride. In some embodiments of any of the pharmaceutical formulations, the pharmaceutical formulation is diluted.

In some embodiments of any of the pharmaceutical formulations, the pharmaceutical formulation comprising the anti-c-met antibody is stable. In some embodiments, the pharmaceutical formulation comprising the anti-c-met antibody is physically stable. In some embodiments, the pharmaceutical formulation comprising the anti-c-met antibody is chemically stable. In some embodiments, the pharmaceutical formulation comprising the anti-c-met antibody is physically stable and chemically stable. In some embodiments, the pharmaceutical formulation comprises an antagonistic anti-c-met antibody and agonistic activity of the pharmaceutical formulation is substantially undetectable. Methods of detecting agonistic and/or agonistic activity are known in the art, for example, U.S. Pat. No. 6,207,152, which is incorporated by reference in its entirety. In some embodiments, the pharmaceutical formulation is substantially nonimmunogenic.

In some embodiments of any of the pharmaceutical formulations, the pharmaceutical formulation does not significantly result in increased aggregate formation after storage at about 40° C. for about two weeks or about four weeks, at about 25° C. for about one month or about three months; at about 5° C. for about six months, about one year, or about two years, and/or about −20° C. for about three months, about six months, or about a year. In some embodiments, the pharmaceutical formulation has reduced or lower levels of aggregate formation after storage at about 40° C. for about two weeks or about four weeks, at about 25° C. for about one month or about three months; at about 5° C. for about six months, about one year, or about two years, and/or about −20° C. for about three months, about six months, or about a year (e.g., compared to a similar formulation at pH 5.7).

High Molecular Weight Species (HMWS) are generally larger than the reference molecule. For example, onartuzumab is about 100 kDa (99,161 Daltons), therefore, a HMWS is greater than about 100 kDa. The size of a bivalent antibody is approximately 150 kDa and a dimer of onartuzumab is about 200 kDa. In some embodiments of any of the pharmaceutical formulations, the pharmaceutical formulation comprises less than about any of 1.5%, 1.25%, 1%, 0.75%, 0.5%, 0.25%, 0.20% or 0.15% HMWS (e.g., upon storage). In some embodiments of any of the pharmaceutical formulations, the pharmaceutical formulation does not significantly increase the percentage of HMWS after storage at about 40° C. for about two weeks or about four weeks, at about 25° C. for about one month or about three months; at about 5° C. for about six months, about one year, or about two years, and/or about −20° C. for about three months, about six months, or about a year. In some embodiments, the pharmaceutical formulation has reduced or lower levels of HMWS after storage at about 40° C. for about two weeks or about four weeks, at about 25° C. for about one month or about three months; at about 5° C. for about six months, about one year, or about two years, and/or about −20° C. for about three months, about six months, or about a year (e.g., compared to a similar formulation at pH 5.7). In some embodiments of any of the pharmaceutical formulations, the pharmaceutical formulation does not significantly increase the percentage of HMWS after storage at about 40° C. for about any of 15 days, 30 days, 45 days, or 60 days or at about 25° C. for about 30 days or about 60 days. In some embodiments, the pharmaceutical formulation has reduced or lower levels of HMWS after storage at about 40° C. for about any of 15 days, 30 days, 45 days, or 60 days or at about 25° C. for about 30 days or about 60 days (e.g., compared to a similar formulation at pH 5.7).

Low Molecular Weight Species (LMWS) are generally smaller than the reference molecule. For example, onartuzumab is about 100 kDa (99,161 Daltons), therefore, a LMWS is less than about 100 kDa. In some embodiments of any of the pharmaceutical formulations, the pharmaceutical formulation does not significantly increase degradation and/or percentage of LMWS after storage at about 40° C. for about two weeks or about four weeks, at about 25° C. for about one month or about three months; at about 5° C. for about six months, about one year, or about two years, and/or about −20° C. for about three months, about six months, or about a year (e.g., compared to a similar formulation at pH 5.7). In some embodiments of any of the pharmaceutical formulations, the pharmaceutical formulation does not significantly increase degradation and/or percentage of LMWS after storage at about 40° C. for about any of 15 days, 30 days, 45 days, or 60 days, at about 25° C. for a for about 30 days or about 60 days (e.g., compared to a similar formulation at pH 5.7).

In some embodiments of any of the pharmaceutical formulations, the percentage of intact polysorbate in the pharmaceutical formulation is greater than about any of 75%, 80%, 85%, or 90% after storage at about 40° C. for about two weeks or about four weeks, at about 25° C. for about one month or about three months; at about 5° C. for about six months, about one year, or about two years, and/or about −20° C. for about three months, about six months, or about a year. In some embodiments of, the percentage of intact polysorbate in the pharmaceutical formulation is greater than about any of 75%, 80%, 85%, or 90% after storage at about 40° C. for about any of one, two, three, four, five, six, seven, or eight weeks.

In some embodiments of any of the pharmaceutical formulations, the percentage of degraded polysorbate in the pharmaceutical formulation is less than about any of 25%, 20%, 15%, or 10% after storage at about 40° C. for about two weeks or about four weeks, at about 25° C. for about one month or about three months; at about 5° C. for about six months, about one year, or about two years, and/or about −20° C. for about three months, about six months, or about a year. In some embodiments, the percentage of degraded polysorbate in the pharmaceutical formulation is less than about any of 25%, 20%, 15%, or 10% after storage at about 40° C. for one, two, three, four, five, six, seven, or eight weeks.

In some embodiments, the ratio of degraded polysorbate to intact polysorbate in the pharmaceutical formulation is less than about any of 0.25, 0.20, 0.15 or 0.10 after storage at about 40° C. for about two weeks or about four weeks, at about 25° C. for about one month or about three months; at about 5° C. for about six months, about one year, or about two years, and/or about −20° C. for about three months, about six months, or about a year. In some embodiments, the ratio of degraded polysorbate to intact polysorbate in the pharmaceutical formulation is less than about any of 0.25, 0.20, 0.15 or 0.10 after storage at about 40° C. for about any of one, two, three, four, five, six, seven, or eight weeks. In some embodiments, the pharmaceutical formulation comprising the anti-c-met antibody is more stable than a similar formulation at pH 5.7 and/or with a polysorbate concentration of 0.02% or less.

Moreover, the pharmaceutical formulation is desirably one which has been demonstrated to be stable upon storage and/or during administration (e.g., after dilution in an IV bag). Various stability assays are available to the skilled practitioner for confirming the stability of the formulation. For example, the formulation may be one which is found to be stable upon storage: at about 25° C. for at least about one month or at least about three months, about 5° C. for at least about six months or at least about one year; and/or about −20° C. for at least about six months or at least about one year. Furthermore, the pharmaceutical formulation is preferably stable following freezing (to, e.g., −70° C.) and thawing of the pharmaceutical formulation. Freezing of the aqueous pharmaceutical formulation, without simultaneous drying that occurs during freeze-drying, is specifically contemplated herein, facilitating longer term storage thereof, for instance in a stainless steel tank. Freezing of the pharmaceutical formulation is specifically contemplated herein. Hence, the pharmaceutical formulation can be tested for stability upon freezing and thawing. In another embodiment, the formulation is provided inside a stainless steel tank. The formulation in the stainless steel tank is optionally frozen and not freeze-dried.

The pharmaceutical formulation to be used for in vivo administration should be sterile. This can be achieved according to the procedures known to the skilled person for generating sterile pharmaceutical formulations suitable for administration to human subjects, including filtration through sterile filtration membranes, prior to, or following, preparation of the formulation.

In some embodiments of any of the pharmaceutical formulations, the pharmaceutical formulation comprising the anti-c-met antibody is stable upon dilution with a diluent (e.g., saline). For example, provided herein are IV bags comprising a diluted pharmaceutical formulation described herein. In some embodiments, the diluent is saline (e.g., 0.9% sodium chloride). In some embodiments, the concentration of the anti-c-met antibody is diluted to about any of 0.5 mg/mL, 1 mg/mL, 1.5 mg/mL, 2 mg/mL, 3 mg/mL, 4 mg/mL or 5 mg/mL. In some embodiments, the concentration of the anti-c-met antibody is diluted to between about any of 0.5-5 mg/mL, 0.5-2.5 mg/mL, or 0.5-1.5 mg/mL. Therefore, for example, provided herein are pharmaceutical formulations comprising a) an anti-c-met antibody, wherein the antibody concentration is about 1 mg/mL, and (b) a polysorbate, wherein the polysorbate concentration is greater than 0.00033% w/v. In some embodiments, the pharmaceutical formulation comprises (a) an anti-c-met antibody, wherein the antibody concentration is about 1 mg/mL; (b) a polysorbate, wherein the polysorbate concentration is greater than 0.00033% w/v; (c) a histidine buffer (e.g., a histidine buffer at a pH between 5.0 and 5.4). In some embodiments of any of the pharmaceutical formulations, the pharmaceutical formulation is stable (e.g., physically stable) in an IV bag and/or IV administration set.

In some embodiments of any of the pharmaceutical formulations, the pharmaceutical formulation (for example, after dilution) is stable upon agitation for any of about thirty minutes, one hour, 1.5 hours, or two hours at about any of 75, 100, 125, or 150 rpm. In some embodiments of any of the pharmaceutical formulations, the pharmaceutical formulation (for example, after dilution) comprises less than about any of 1.5%, 1.25%, 1%, 0.75%, 0.5%, 0.25%, 0.20% or 0.15% HMWS (for example, upon agitation).

Provided herein are also methods of making a pharmaceutical formulation comprising preparing the formulation as described herein. In some embodiments, the methods further comprise evaluating physical stability, chemical stability, or biological activity of the anti-c-met antibody in the formulation.

Stability can be tested by evaluating physical stability, chemical stability, and/or biological activity of the antibody in the formulation around the time of formulation as well as following storage, during administration, and/or upon agitation at the noted temperatures. Physical and/or stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may result in aggregation, deamidation (e.g., Asn deamidation), oxidation (e.g., Met oxidation), isomerization (e.g., Asp isomerization), clipping/hydrolysis/fragmentation (e.g., hinge region fragmentation), succinimide formation, unpaired cysteine(s), N-terminal extension, C-terminal processing, glycosylation differences, etc. Biological activity or antigen binding function can be evaluated using various techniques available to the skilled practitioner.

One or more other pharmaceutically acceptable carriers, excipients or stabilizers such as those described in Remington's Pharmaceutical Sciences 18th edition, Gennaro, A. Ed. (1990) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g., Zn-protein complexes); biodegradable polymers such as polyesters; preservatives; and/or salt-forming counterions such as sodium.

III. ANTI-C-MET ANTIBODIES

Provided herein are anti-c-met antibodies for use in the pharmaceutical formulations described herein. Useful anti-c-met antibodies include antibodies that bind with sufficient affinity and specificity to c-met and can reduce or inhibit one or more c-met activities. Anti-c-met antibodies in the pharmaceutical formulations can be used to modulate one or more aspects of HGF/c-met-associated effects, including but not limited to c-met activation, downstream molecular signaling (e.g., mitogen activated protein kinase (MAPK) phosphorylation), cell proliferation, cell migration, cell survival, cell morphogenesis and angiogenesis. These effects can be modulated by any biologically relevant mechanism, including disruption of ligand (e.g., HGF) binding to c-met, c-met phosphorylation and/or c-met multimerization. In some embodiments, the anti-c-met antibody is an antagonist anti-c-met antibody. In some embodiments, the anti-c-met antibody interferes with diseases or conditions wherein c-met/HGF activity is involved.

In some embodiments of any of the anti-c-met antibody formulations described herein, the anti-c-met antibody is an anti-c-met antibody fragment. In some embodiments, the anti-c-met antibody is an antagonist anti-c-met antibody. In some embodiments, the anti-c-met antibody is monovalent. In some embodiments, the anti-c-met antibody fragment may comprise a single antigen binding arm and an Fc region. Anti-c-met antibody fragments are described herein and are known in the art, in the one-armed format. Accordingly, in some embodiments, the anti-c-met antibody fragment is a one-armed antibody (i.e., the heavy chain variable domain and the light chain variable domain form a single antigen binding arm) comprising an Fc region, wherein the Fc region comprises a first and a second Fc polypeptide, wherein the first and second Fc polypeptides are present in a complex. In some embodiments, the first and second Fc polypeptides form a Fc region that increases stability of the anti-c-met antibody compared to a Fab molecule comprising said antigen binding arm. In some embodiments, the anti-c-met antibody comprises (a) a first polypeptide comprising the amino acid sequence of SEQ ID NO:19, a CH1 sequence, and a first Fc polypeptide and (b) a second polypeptide comprising the amino acid sequence of SEQ ID NO:20 and CL1 sequence. In some embodiments, the anti-c-met antibody further comprises (c) a third polypeptide comprising a second Fc polypeptide.

In some embodiments, the anti-c-met antibody fragment of the pharmaceutical formulation described herein comprises an antigen binding site of the bivalent antibody and thus retains the ability to bind antigen. In some embodiments, the anti-c-met antibody fragment comprises the Fc region and retains at least one of the biological functions normally associated with the Fc region when present in an bivalent antibody, such as FcRn binding, antibody half life modulation, ADCC function and complement binding. In some embodiments, the anti-c-met antibody fragment does not have ADCC function and/or complement binding activity. In some embodiments, the anti-c-met antibody fragment is a monovalent antibody that has an in vivo half life substantially similar to a bivalent antibody. For example, such an antibody fragment may comprise on antigen binding arm linked to an Fc sequence capable of conferring in vivo stability to the fragment. In some embodiments, an Fc polypeptide comprises part or all of a wild type hinge sequence (generally at its N terminus). In some embodiments, an Fc polypeptide does not comprise a functional or wild type hinge sequence. In some embodiments, the anti-c-met antibody fragment is a one-armed antibody as described in WO2005/063816. In some embodiments, the one-armed antibody comprises Fc mutations constituting "knobs" and "holes" as described in WO2005/063816; Ridgeway, J et al, *Prot Eng* (1996) 9:617-21; and Zhu Z et al. *Prot Sci* (1997) 6:781-8. In some embodiments, the Fc region comprises at least one protuberance (knob) and at least one cavity (hole), wherein presence of the protuberance and cavity enhances formation of a complex between an Fc polypeptide comprising the protuberance and an Fc polypeptide comprising the cavity, for example as described in WO 2005/063816. In some embodiments, the Fc region of the anti-c-met antibodies comprises a first and a second Fc polypeptide, wherein the first and second polypeptide each comprises one or more mutations with respect to wild type human Fc. In some embodiments, a cavity mutation is T366S, L368A and/or Y407V. In some embodiments, a protuberance mutation is T366W. In some embodiments, the first polypeptide comprises the Fc sequence depicted in FIG. 2 and the second polypeptide comprises the Fc sequence depicted in FIG. 3. In some embodiments, the anti-c-met antibody may comprise at least one characteristic that promotes heterodimerization, while minimizing homodimerization, of the Fc sequences within the antibody fragment.

In some embodiments of any of the anti-c-met antibodies described herein, the anti-c-met antibody is an antagonist anti-c-met antibody. In some embodiments, blocking anti-c-met antibodies or antagonist anti-c-met antibodies completely inhibit the biological activity of the antigen. For treatment of pathological conditions requiring an antagonistic function and where bivalency of an anti-c-met antibody results in an undesirable agonistic effect upon binding to a target antigen (even though it is an antagonistic anti-c-met antibody as a Fab fragment), the monovalent trait of a one-armed antibody (i.e., an antibody comprising a single antigen binding arm) results in and/or ensures an antagonistic function upon binding of the anti-c-met antibody to a target molecule. Furthermore, the one-armed antibody comprising a Fc region is characterized by superior pharmacokinetic attributes (such as an enhanced half life and/or reduced clearance rate in vivo) compared to Fab forms having similar/substantially identical antigen binding characteristics, thus overcoming a major drawback in the use of conventional monovalent Fab antibodies.

Anti-c-met antibodies (which may be provided as one-armed antibodies) useful in the pharmaceutical formulation described herein include those known in the art (see, e.g., Martens, T. et al., *Clin. Cancer Res.* 12 (20 Pt. 1):6144 (2006); U.S. Pat. No. 6,468,529; WO2006/015371; WO2007/063816, and WO2010/045345, which are incorporated by reference in their entirety). In some embodiments, the anti-c-met antibody for use in the pharmaceutical formulations described herein comprises one or more of the HVR sequences of the monoclonal antibody produced by the hybridoma cell line deposited under American Type Culture Collection (ATCC) Accession Number ATCC HB-11894 (hybridoma 1A3.3.13) or HB-11895 (hybridoma 5D5.11.6). In some embodiments, the anti-c-met antibody is a one-armed antibody comprising one or more of the HVRs of the light chain variable domain and/or one or more of the HVRs of the heavy chain variable domain of ATCC Accession Number ATCC HB-11894 (hybridoma 1A3.3.13) or HB-11895 (hybridoma 5D5.11.6) and an Fc polypeptide.

In some embodiments of the anti-c-met antibody pharmaceutical formulation, the anti-c-met antibody comprises a light chain variable domain comprising one or more of HVR1-LC, HVR2-LC and HVR3-LC sequence depicted in FIG. 2 (SEQ ID NOs:1-3). In some embodiments, the anti-c-met antibody comprises a heavy chain variable domain comprising one or more of HVR1-HC, HVR2-HC and HVR3-HC sequence depicted in FIG. 2 (SEQ ID NOs:4-6). In some embodiments, the anti-c-met antibody comprises a light chain variable domain comprising one or more of HVR1-LC, HVR2-LC and HVR3-LC sequence depicted in FIG. 2 (SEQ ID NOs:1-3) and one or more of HVR1-HC, HVR2-HC and HVR3-HC sequence depicted in FIG. 2 (SEQ ID NOs:4-6). In some embodiments, the heavy chain variable domain comprises one or more of HVR1-HC, HVR2-HC and HVR3-HC sequence depicted in FIG. 2 (SEQ ID NOs:4-6) and one or more of FR1-HC, FR2-HC, FR3-HC and FR4-HC sequence depicted in FIG. 2 (SEQ ID NOs:11-14). In some embodiments, the light chain variable domain comprises one or more of HVR1-LC, HVR2-LC and HVR3-LC sequence depicted in FIG. 2 (SEQ ID NOs:1-3) and one or more of FR1-LC, FR2-LC, FR3-LC and FR4-LC sequence depicted in FIG. 2 (SEQ ID NOs:7-10). In some embodiments, the anti-c-met antibody is a one-armed antibody comprising one or more of the HVRs of the light chain variable domain (SEQ ID NOs:1-3) and/or one or more of the HVRs of the heavy chain variable domain (SEQ ID NOs:4-6) and an Fc polypeptide.

In some embodiments of the anti-c-met antibody pharmaceutical formulation, the anti-c-met antibody comprises: (a) at least one, two, three, four, or five HVR sequences selected from the group consisting of: (i) HVR-L1 comprising sequence A1-A17, wherein A1-A17 is KSSQSLLYTSSQKNYLA (SEQ ID NO:23) (ii) HVR-L2 comprising sequence B1-B7, wherein B1-B7 is WASTRES (SEQ ID NO:24); (iii) HVR-L3 comprising sequence C1-C9, wherein C1-C9 is QQYYAYPWT (SEQ ID NO:25); (iv) HVR-H1 comprising sequence D1-D10, wherein D1-D10 is GYTFTSYWLH (SEQ ID NO:26); (v) HVR-H2 comprising sequence E1-E18, wherein E1-E18 is GMIDPSNSDTRFNPNFKD (SEQ ID NO:27); and (vi) HVR-H3 comprising sequence F1-F11, wherein F1-F11 is XYGSYVSPLDY (SEQ ID NO:28) and X is not R; and (b) at least one variant HVR, wherein the variant HVR sequence comprises modification of at least one residue of the sequence depicted in SEQ ID NOs:23, 24, 25, 26, 27, or 28. In some embodiments, HVR-L1 of the anti-c-met antibody comprises the sequence of SEQ ID NO:23. In some embodiments, HVR-L2 comprises the sequence of SEQ ID NO:24. In some embodiments, HVR-L3 comprises the sequence of SEQ ID NO:25. In some embodiments, HVR-H1 comprises the sequence of SEQ ID NO:26. In some embodiments, HVR-H2 comprises the sequence of SEQ ID NO:27. In some embodiments, HVR-H3 the sequence of SEQ ID NO:28. In some embodiments, HVR-H3 comprises TYGSYVSPLDY (SEQ ID NO: 29). In some embodiments, HVR-H3 comprises SYGSYVSPLDY (SEQ ID NO:30). In some embodiments, the anti-c-met antibody comprising these sequences (in combination as described herein) is humanized or human. In some embodiments, the anti-c-met antibody is a one-armed antibody comprising one or more of the HVRs of the light chain variable domain (SEQ ID NOs:23-25) and/or one or more of the HVRs of the heavy chain variable domain (SEQ ID NOs:26-30) and an Fc polypeptide.

Provided herein are also anti-c-met antibodies for use in the pharmaceutical formulation comprising one, two, three, four, five or six HVRs, wherein each HVR comprises, consists or consists essentially of a sequence selected from the group consisting of SEQ ID NOs:23, 24, 25, 26, 27, 28, and 29, and wherein SEQ ID NO:23 corresponds to an HVR-L1, SEQ ID NO:24 corresponds to an HVR-L2, SEQ ID NO:25 corresponds to an HVR-L3, SEQ ID NO:26 corresponds to an HVR-H1, SEQ ID NO:27 corresponds to an HVR-H2, and SEQ ID NOs:26, 27, or 28 corresponds to an HVR-H3. In some embodiments, the anti-c-met antibody comprises HVR-L1, HVR-L2, HVR-L3, HVR-H1, HVR-H2, and HVR-H3, wherein each, in order, comprises SEQ ID NOs:23, 24, 25, 26, 27 and 29. In some embodiments, the anti-c-met antibody comprises HVR-L1, HVR-L2, HVR-L3, HVR-H1, HVR-H2, and HVR-H3, wherein each, in order, comprises SEQ ID NOs:23, 24, 25, 26, 27 and 30.

Variant HVRs can have modifications of one or more residues within the HVR. In some embodiments, a HVR-L2 variant comprises 1-5 (1, 2, 3, 4 or 5) substitutions in any combination of the following positions: B1 (M or L), B2 (P, T, G or S), B3 (N, G, R or T), B4 (I, N or F), B5 (P, I, L or G), B6 (A, D, T or V) and B7 (R, I, M or G). In some embodiments, a HVR-H1 variant comprises 1-5 (1, 2, 3 or 5) substitutions in any combination of the following positions: D3 (N, P, L, S, A, I), D5 (I, S or Y), D6 (G, D, T, K, R), D7 (F, H, R, S, T or V) and D9 (M or V). In some embodiments, a HVR-H2 variant comprises 1-4 (1, 2, 3 or 4) substitutions in any combination of the following positions: E7 (Y), E9 (I), E10 (I), E14 (T or Q), E15 (D, K, S, T or V), E16 (L), E17 (E, H, N or D) and E18 (Y, E or H). In some embodiments, a HVR-H3 variant comprises 1-5 (1, 2, 3, 4 or 5) substitutions in any combination of the following positions: F1 (T, S), F3 (R, S, H, T, A, K), F4 (G), F6 (R, F, M, T, E, K, A, L, W), F7 (L, I, T, R, K, V), F8 (S, A), F10 (Y, N) and F11 (Q, S, H, F). Letter(s) in parenthesis following each position indicates an illustrative substitution (i.e., replacement) amino acid; as would be evident to one skilled in the art, suitability of other amino acids as substitution amino acids in the context described herein can be routinely assessed using techniques known in the art and/or described herein. In some embodiments, a HVR-L1 comprises the sequence of SEQ ID NO:23. In some embodiments, F1 in a variant HVR-H3 is T. In some embodiments, F1 in a variant HVR-H3 is S. In some embodiments, F3 in a variant HVR-H3 is R. In some embodiments, F3 in a variant HVR-H3 is S. In some embodiments, F7 in a variant HVR-H3 is T. In some embodiments, the anti-c-met antibody comprises a variant HVR-H3 wherein F1 is T or S, F3 is R or S, and F7 is T.

In some embodiments, the anti-c-met antibody of the pharmaceutical formulation comprises a variant HVR-H3 wherein F1 is T, F3 is R and F7 is T. In some embodiments, the anti-c-met antibody comprises a variant HVR-H3 wherein F1 is S. In some embodiments, the anti-c-met antibody comprises a variant HVR-H3 wherein F1 is T, and F3 is R. In some embodiments, the anti-c-met antibody comprises a variant HVR-H3 wherein F1 is S, F3 is R and F7 is T. In some embodiments, the anti-c-met antibody comprises a variant HVR-H3 wherein F1 is T, F3 is S, F7 is T, and F8 is S. In some embodiments, the anti-c-met antibody comprises a variant HVR-H3 wherein F1 is T, F3 is S, F7 is T, and F8 is A. In some embodiments, said variant HVR-H3 antibody further comprises HVR-L1, HVR-L2, HVR-L3, HVR-H1 and HVR-H2 wherein each comprises, in order, the sequence depicted in SEQ ID NOs:1, 2, 3, 4 and 5. In some embodiments, these antibodies further comprise a human subgroup III heavy chain framework consensus sequence. In some embodiments of these antibodies, the framework consensus sequence comprises substitution at position 71, 73 and/or 78. In some embodiments of these antibodies, position 71 is A, 73 is T and/or 78 is A. In some embodiments of these antibodies, these antibodies further comprise a human κI light chain framework consensus sequence.

In some embodiments, the anti-c-met antibody of the pharmaceutical formulation comprises a variant HVR-L2 wherein B6 is V. In some embodiments, said variant HVR-L2 anti-c-met antibody further comprises HVR-L1, HVR-L3, HVR-H1, HVR-H2 and HVR-H3, wherein each comprises, in order, the sequence depicted in SEQ ID NOs:23, 25, 26, 27 and 28. In some embodiments, said variant HVR-L2 anti-c-met antibody further comprises HVR-L1, HVR-L3, HVR-H1, HVR-H2 and HVR-H3, wherein each comprises, in order, the sequence depicted in SEQ ID NOs:23, 25, 26, 27 and 29. In some embodiments, said variant HVR-L2 anti-c-met antibody further comprises HVR-L1, HVR-L3, HVR-H1, HVR-H2 and HVR-H3, wherein each comprises, in order, the sequence depicted in SEQ ID NOs:23, 25, 26, 27 and 30. In some embodiments, these anti-c-met antibodies further comprise a human subgroup III heavy chain framework consensus sequence. In some embodiments of these anti-c-met antibodies, the framework consensus sequence comprises substitution at position 71, 73 and/or 78. In some embodiments of these anti-c-met antibodies, position 71 is A, 73 is T and/or 78 is A. In some embodiments of these anti-c-met antibodies, these antibodies further comprise a human κI light chain framework consensus sequence.

In some embodiments, the anti-c-met antibody of the pharmaceutical formulation comprises a variant HVR-H2 wherein E14 is T, E15 is K and E17 is E. In some embodiments, the anti-c-met antibody comprises a variant HVR-H2 wherein E17 is E. In some embodiments, said variant HVR-H3 anti-c-met antibody further comprises HVR-L1, HVR-L2, HVR-L3, HVR-H1, and HVR-H3 wherein each comprises, in order, the sequence depicted in SEQ ID NOs:23, 24, 25, 26, and 28. In some embodiments, said variant HVR-H2 anti-c-met antibody further comprises HVR-L1, HVR-L2, HVR-L3, HVR-H1, and HVR-H3, wherein each comprises, in order, the sequence depicted in SEQ ID NOs:23, 24, 25, 26, and 29. In some embodiments, said variant HVR-H2 anti-c-met antibody further comprises HVR-L1, HVR-L2, HVR-L3, HVR-H1, and HVR-H3, wherein each comprises, in order, the sequence depicted in SEQ ID NOs:23, 24, 25, 26 and 30. In some embodiments, these anti-c-met antibodies further comprise a human subgroup III heavy chain framework consensus sequence. In some embodiments of these anti-c-met antibodies, the framework consensus sequence comprises substitution at position 71, 73 and/or 78. In some embodiments of these anti-c-met antibodies, position 71 is A, 73 is T and/or 78 is A. In some embodiments of these antibodies, these anti-c-met antibodies further comprise a human κI light chain framework consensus sequence.

In some embodiments, the anti-c-met antibody of the pharmaceutical formulation comprises (a) a heavy chain variable domain comprising the sequence: EVQLVESGGGLVQPGGSLRLSCAASGYTFTSYWLHWVRQAPGKGLEWVGMIDPSNSDTR FNPNFKDRFTISADTSKNTAYLQMNSLRAEDTAVYYCATYRSYVTPLDYWGQGTLVTVS S (SEQ ID NO:19) and/or (b) a light chain variable domain comprising the sequence: DIQMTQSPSSLSASVGDRVTITCKSSQSLLYTSSQKNYLAWYQQKPGKAPKLLIYWASTR ESGVPSRFSGSGSGTDFTLTISSLQPEDFATYYCQQYYAYPWTFGQGTKVEIKR (SEQ ID NO:20). In some embodiments, the anti-c-met antibody is a one-armed antibody comprising (a) the light chain variable domain (SEQ ID NO:20) and/or (b) the heavy chain variable domain (SEQ ID NO:19) and (c) a Fc polypeptide.

In some embodiments, the anti-c-met antibody of the pharmaceutical formulation comprises (a) HVR-H1, HVR-H2, and HVR-H3 of a heavy chain variable domain comprising the sequence: EVQLVESGGGLVQPGGSLRLSCAASGYTFTSYWLHWVRQAPGKGLEWVGMIDPSNSDTR FNPNFKDRFTISADTSKNTAYLQMNSLRAEDTAVYYCATYRSYVTPLDYWGQGTLVTVS S (SEQ ID NO:19) and/or (b) HVR-L1, HVR-L2, and HVR-L3 of a light chain variable domain comprising the sequence: DIQMTQSPSSLSASVGDRVTITCKSSQSLLYTSSQKNYLAWYQQKPGKAPKLLIYWASTR ESGVPSRFSGSGSGTDFTLTISSLQPEDFATYYCQQYYAYPWTFGQGTKVEIKR (SEQ ID NO:20). In some embodiments, the anti-c-met antibody is a one-armed antibody comprising (a) the light chain variable domain (SEQ ID NO:20) and/or (b) the heavy chain variable domain (SEQ ID NO:19) and (c) a Fc polypeptide.

In some embodiments, the anti-c-met antibody of the pharmaceutical formulation is an anti-c-met antibody fragment, wherein the antibody fragment comprises (a) a first polypeptide comprising a heavy chain variable domain comprising SEQ ID NO:19, CH1 sequence (e.g., SEQ ID NO:16), and a first Fc polypeptide; and (b) a second polypeptide comprising a light chain variable domain comprising SEQ ID NO:20, and CL1 sequence (e.g., SEQ ID NO:15).

In some embodiments, the anti-c-met antibody of the pharmaceutical formulation is an anti-c-met antibody fragment, wherein the antibody fragment comprises (a) a first polypeptide comprising a heavy chain variable domain comprising SEQ ID NO:19, CH1 sequence (e.g., SEQ ID NO:16), and a first Fc polypeptide; (b) a second polypeptide comprising a light chain variable domain comprising SEQ ID NO:20, and CL1 sequence (e.g., SEQ ID NO:15); and (c) a third polypeptide comprising a second Fc polypeptide, wherein the heavy chain variable domain and the light chain variable domain are present as a complex and form a single antigen binding arm and wherein the first and second Fc polypeptides are present in a complex. In some embodiments, the first and second Fc polypeptides form a Fc region that increases stability of said antibody fragment compared to a Fab molecule comprising said antigen binding arm. In some embodiments, the Fc region is that of a human IgG (e.g., IgG1, 2, 3 or 4). In some embodiments, the first Fc polypeptide comprises the Fc sequence depicted in FIG. 2 (SEQ ID NO:17) and the second Fc polypeptide comprises the Fc sequence depicted in FIG. 3 (SEQ ID NO:18). In some embodiments, the first Fc polypeptide comprises the Fc sequence depicted in FIG. 3 (SEQ ID NO:18) and the second Fc polypeptide comprises the Fc sequence depicted in FIG. 2 (SEQ ID NO:17).

In some embodiments, the anti-c-met antibody is an anti-c-met antibody or antibody fragment thereof, wherein the antibody comprises (a) a first polypeptide comprising a heavy chain variable domain comprising SEQ ID NO:19, CH1 sequence, and a first Fc polypeptide; (b) a second polypeptide comprising a light chain variable domain comprising SEQ ID NO:20, and CL1 sequence; and (c) a third polypeptide comprising a second Fc polypeptide, wherein the heavy chain variable domain and the light chain variable domain are present as a complex and form a single antigen binding arm, wherein the first and second Fc polypeptides are present in a complex and form a Fc region that increases stability of said antibody fragment compared to a Fab molecule comprising said antigen binding arm.

In some embodiments, the anti-c-met antibody comprises (a) a first polypeptide comprising a heavy chain variable domain, said polypeptide comprising the sequence: EVQLVESGGGLVQPGGSLRLSCAASGYTFTSYWLH-WVRQAPGKGLEWVGMIDPSNSDTR FNPNFKDRFTI-SADTSKNTAYLQMNSLRAEDTAVYYCATYRSYVT-PLDYWGQGTLVTVSS ASTKGPSVFPLAPSSKSTS-GGTAALGCLVKDYFPEPVTVSWNSGALTSGVHTF-PAVLQSSG LYSLSSVVTVPSSSLGTQTYICNVNH-KPSNTKVDKKVEPKSCDKTHTCPPCPAPELLGGPS VFLFPPKPKDTLMISRTPEVTCVVVDVSHEDPEVKF-NWYVDGVEVHNAKTKPREEQYNST YRVVSVLTVL-HQDWLNGKEYKCKVSNKALPAPIEKTISKAK-GQPREPQVYTLPPSREEMT KNQVSLSCAV-KGFYPSDIAVEWESNGQPENNYKTTPPVLDSDGSF-FLVSKLTVDKSRWQQ GNVFSCSVMHEALHN-HYTQKSLSLSPGK (SEQ ID NO:21); (b) a second polypeptide comprising a light chain variable domain, the polypeptide comprising the sequence DIQMTQSPSSLSAS-VGDRVTITCKSSQSLLYTSSQKNYLAWYQQKPGKAP-KLLIYWASTRE SGVPSRFSGSGSGTDFTLTISSLQPED-FATYYCQQYYAYPWTFGQGTKVEIKRTVAAPSVFI FPPSDEQLKSGTASVVCLLNNFYPREAKVQWKVD-NALQSGNSQESVTEQDSKDSTYSLSS TLTL-SKADYEKHKVYACEVTHQGLSSPVTKSFNRGEC (SEQ ID NO:22); and a third polypeptide comprising a Fc sequence, the polypeptide comprising the sequence DKTH-TCPPCPAPELLGGPSVFLFPPKPKDTLMISRTPEVTCV-VVDVSHEDPEVKFNWYVDG VEVHNAKTKPRE-EQYNSTYRVVSVLTVLHQDWLNGKEYKCKVSNK-ALPAPIEKTISKAK GQPREPQVYTLPPSREEMTKN-QVSLWCLVKGFYPSDIAVEWESNGQPENNYKTTPPV-LDS DGSFFLYSKLTVDKSRWQQGNVFSCSVM-HEALHNHYTQKSLSLSPGK (SEQ ID NO:18), wherein the heavy chain variable domain and the light chain variable domain are present as a complex and form a single antigen binding arm and wherein the first and second Fc polypeptides are present in a complex. In some embodiments, the first and second Fc polypeptides form a Fc region that increases stability of said antibody fragment compared to a Fab molecule comprising said antigen binding arm.

In some embodiments, polynucleotides encoding any of the anti-c-met antibodies described herein are expressed such that the anti-c-met antibody is produced. In some embodiments, polynucleotides encoding any of the anti-c-met antibody are expressed in vitro or in vivo (for example, in CHO cells or *E. coli* cells).

In some embodiments, the anti-c-met antibody for use in the pharmaceutical formulation described herein is onartuzumab (interchangeably termed MetMAb), a one-armed antibody comprising a Fc region. A sequence of MetMAb is shown in FIGS. 2 and 3. MetMAb (also termed OA5D5v2 and onartuzumab) is also described in, e.g., WO2006/015371; WO2010/04345; and Jin et al, Cancer Res (2008) 68:4360. Biosimilar version of MetMAb are also contemplated and encompassed herein for use in the formulation.

In some embodiments, the anti-c-met antibody of the pharmaceutical formulation specifically binds at least a portion of c-met Sema domain or variant thereof. In some embodiments, the anti-c-met antibody is an antagonist. In some embodiments, the anti-c-met antagonist antibody specifically binds at least one of the sequences selected from the group consisting of LDAQT (SEQ ID NO:31) (e.g., residues 269-273 of c-met), LTEKRKKRS (SEQ ID NO:32) (e.g., residues 300-308 of c-met), KPDSAEPM (SEQ ID NO: 33) (e.g., residues 350-357 of c-met) and NVRCLQHF (SEQ ID NO:34) (e.g., residues 381-388 of c-met). In some embodiments, the anti-c-met antagonist antibody specifically binds a conformational epitope formed by part or all of at least one of the sequences selected from the group consisting of LDAQT (SEQ ID NO:31) (e.g., residues 269-273 of c-met), LTEKRKKRS (SEQ ID NO:32) (e.g., residues 300-308 of c-met), KPDSAEPM (SEQ ID NO: 33) (e.g., residues 350-357 of c-met) and NVRCLQHF (SEQ ID NO:34) (e.g., residues 381-388 of c-met). In some embodiments, an antagonist antibody specifically binds an amino acid sequence having at least 50%, 60%, 70%, 80%, 90%, 95%, 98% sequence identity or similarity with the sequence LDAQT (SEQ ID NO:31), LTEKRKKRS (SEQ ID NO:32), KPDSAEPM (SEQ ID NO:33) and/or NVRCLQHF (SEQ ID NO:34). In some embodiments, the anti-c-met antibody is an antagonist anti-c-met antibody. In some embodiments, the anti-c-met antibody is a one-armed antibody. In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

In some embodiments of any of the anti-c-met antibodies described herein, the anti-c-met antibody may interfere with HGF/c-met activation, including but not limited to interfering with HGF binding to the extracellular portion of c-met and receptor multimerization. In some embodiments, the anti-c-met antibody are useful in treating or diagnosing pathological conditions associated with abnormal or unwanted signaling of the HGF/c-met pathway. In some embodiments, the anti-c-met antibody may modulate the HGF/c-met pathway, including modulation of c-met ligand binding, c-met dimerization, activation, and other biological/physiological activities associated with HGF/c-met signaling. In some embodiments, the anti-c-met antibody may disrupt HGF/c-met signaling pathway. In some embodiments of any of the anti-c-met antibodies described herein, binding of the anti-c-met antibody to c-met inhibits c-met activation by HGF. In some embodiments of any of the anti-c-met antibodies described herein, binding of the anti-c-met antibody to c-met in a cell inhibits proliferation, survival, scattering, morphogenesis and/or motility of the cell.

In some instances, it may be advantageous to have an anti-c-met antibody that does not interfere with binding of a ligand (such as HGF) to c-met. Accordingly, in some embodiments, the anti-c-met antibody does not bind an HGF binding site on c-met. In some embodiment, the anti-c-met antibody does not substantially inhibit HGF binding to c-met. In some embodiments, the anti-c-met antibody does not substantially compete with HGF for binding to c-met. In one example, the anti-c-met antibody can be used in conjunction with one or more other antagonists, wherein the antagonists are targeted at different processes and/or functions within the HGF/c-met axis. Thus, in some embodiments, the anti-c-met antibody binds to an epitope on c-met distinct from an epitope bound by another c-met antagonist (such as the Fab fragment of the monoclonal antibody produced by the hybridoma cell line deposited under American Type Culture Collection Accession Number ATCC HB-11894 (hybridoma 1A3.3.13)). In another embodiment, the anti-c-met antibody is distinct from (i.e., it is not) a Fab fragment of the monoclonal antibody produced by the hybridoma cell line deposited under American Type Culture Collection Accession Number ATCC HB-11894 (hybridoma 1A3.3.13).

In some embodiments, the anti-c-met antibody binds to c-met of a first animal species, and does not specifically bind to c-met of a second animal species. In some embodiments, the first animal species is human and/or primate (e.g., cynomolgus monkey), and the second animal species is murine (e.g., mouse) and/or canine. In some embodiments, the first animal species is human. In some embodiments, the first animal species is primate, for example cynomolgus monkey. In some embodiments, the second animal species is murine, for example mouse. In some embodiments, the second animal species is canine.

In some embodiments, the anti-c-met antibody elicits little to no immunogenic response in said subject. In some embodiments, the anti-c-met antibody elicits an immunogenic response at or less than a clinically-acceptable level.

In some embodiments of any of the anti-c-met antibodies described herein, an altered antibody that possesses some but not all effector functions. In some embodiments, the anti-c-met antibody does not possess complement depletion and/or ADCC activity. In some embodiments, the Fc activities of the produced immunoglobulin are measured to ensure that only the desired properties are maintained (e.g., half-life but not complement depletion and/or ADCC activity). In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art. In some embodiments, the anti-c-met antibody is glycosylated. In some embodiments, the anti-c-met antibody is substantially aglycosylated.

The anti-c-met antibodies of the formulations described herein can be characterized for their physical/chemical properties and biological functions by various assays known in the art. The purified anti-c-met antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In some embodiments of any of the anti-c-met antibodies described herein, the anti-c-met antibody may be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue, or silver stain.

Further, in some embodiments, the anti-c-met antibody according to any of the above embodiments may incorporate any of the features, singly or in combination, as described in Sections 1-8 below:

1. Antibody Affinity

In some embodiments, the anti-c-met antibody provided herein has a dissociation constant (Kd) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M).

Binding affinity of a ligand to its receptor can be determined using any of a variety of assays, and expressed in terms of a variety of quantitative values. Antigen binding assays are known in the art and can be used herein include without limitation any direct or competitive binding assays using techniques such as western blots, radioimmunoassays, enzyme-linked immunoabsorbent assay (ELISA), "sandwich" immunoassays, surface plasmon resonance based assay (such as the BIAcore assay as described in PCT Application Publication No. WO2005/012359), immunoprecipitation assays, fluorescent immunoassays, and protein A immunoassays.

Accordingly, in some embodiments, the binding affinity is expressed as Kd values and reflects intrinsic binding affinity (e.g., with minimized avidity effects). The anti-c-met antibody selected will normally have a sufficiently strong binding affinity for c-met, for example, the antibody may bind human c-met with a Kd value of between 100 nM$^{-1}$ pM.

2. Antibody Fragments

In some embodiments, the anti-c-met antibody of the pharmaceutical formulation described herein is an antibody fragment. Antibody fragments include, but are not limited to, Fab, Fab', Fab'-SH, F(ab')$_2$, Fv, one-armed antibodies, and scFv fragments, and other fragments described below. For a review of certain antibody fragments, see Hudson et al. Nat. Med. 9:129-134 (2003). For a review of scFv fragments, see, e.g., Pluckthiin, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. Other monovalent antibody forms are described in, e.g., WO2007048037, WO2008145137, WO2008145138, and WO2007059782. One-armed antibodies are described, e.g., in WO2005/063816. Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In some embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In some embodiments, the anti-c-met antibody of the pharmaceutical formulation described herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-HVR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In some embodiments, the anti-c-met antibody of the pharmaceutical formulation described herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

The anti-c-met antibody of the pharmaceutical formulation described herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In some phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In some embodiments, the anti-c-met antibody of the pharmaceutical formulation described herein is a multispecific antibody, e.g. a bispecific antibody. Multispecific antibodies are monoclonal antibodies that have binding specificities for at least two different sites. In some embodiments, one of the binding specificities is for an antigen and the other is for any other antigen. In some embodiments, bispecific antibodies may bind to two different epitopes of an antigen. Bispecific antibodies may also be used to localize cytotoxic agents to cells which express an antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., *EMBO J.* 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (scFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to c-met as well as another, different antigen (see, US 2008/0069820, for example).

7. Antibody Variants

In some embodiments, amino acid sequence variants of the anti-c-met antibody for use in the pharmaceutical formulation described herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a. Substitution, Insertion, and Deletion Variants

In some embodiments, anti-c-met antibody variants having one or more amino acid substitutions for use in the pharmaceutical formulation described herein are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b. Glycosylation Variants

In some embodiments, the anti-c-met antibody of the pharmaceutical formulation described herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In some embodiments, one or more amino acid modifications may be introduced into the Fc region of the anti-c-met antibody of the pharmaceutical formulation described herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, contemplated are antibody variants that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.*

24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d. Cysteine Engineered Antibody Variants

In some embodiments, it may be desirable to create cysteine engineered antibodies, e.g., "thioMAbs," in which one or more residues of the anti-c-met antibody of the pharmaceutical formulation described herein are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In some embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e. Antibody Derivatives

In some embodiments, the anti-c-met antibody of the pharmaceutical formulation described herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of the anti-c-met antibody and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

8. Immunoconjugates

Immunoconjugates comprising the anti-c-met antibody conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes are contemplated for use in the pharmaceutical formulation described herein.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In some embodiments, an immunoconjugate comprises the anti-c-met antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes.

In some embodiments, an immunoconjugate comprises the anti-c-met antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example Tc99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of the anti-c-met antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

IV. RECOMBINANT METHODS AND COMPOSITIONS

The anti-c-met antibody for use in any of the pharmaceutical formulations described herein may be produced recombinant methods and compositions, e.g., as described in U.S. Pat. No. 4,816,567. In one embodiment, isolated nucleic acid encoding an antibody is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. Production of a one-armed antibody is described, e.g., in WO2005/063816.

In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523, WO/05/063816. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

V. USES AND METHODS OF TREATMENT

The pharmaceutical formulations provided herein comprising an anti-c-met antibody are useful for modulating disease states associated with dysregulation of the HGF/c-met signaling axis. The HGF/c-met signaling pathway is involved in multiple biological and physiological functions, including, e.g., cell proliferation and angiogenesis.

Provided herein are methods of inhibiting c-met activated cell proliferation, said method comprising contacting a cell or tissue with a pharmaceutical formulation described herein (e.g., upon dilution (e.g., a diluted pharmaceutical formulation described herein)) comprising an effective amount of an anti-c-met antibody, whereby cell proliferation associated with c-met activation is inhibited. In some embodiments, the cell proliferative disorder is associated with increased expression or activity of c-met or hepatocyte growth, or both. In some embodiments, the cancer is c-met positive (expresses high levels of c-met, for example, by immunohistochemistry). In some embodiments, the cell proliferation is cancer. In some embodiments, the cancer is non-small cell lung cancer (NSCLC), glioblastoma, pancreatic cancer, sarcoma, renal cell carcinoma, hepatocellular carcinoma, gastric cancer, colorectal cancer, or breast cancer. In some embodiments, the cancer is stage IIIb and/or stage IV. In some embodiments, the cancer is locally advanced or metastatic cancer. In some embodiments, the therapy is second line or third line therapy (e.g., second line or third line NSCLC therapy). In some embodiments, the cancer is EGFR mutant. In some embodiments, the cancer is EGFR wild-type. In some embodiments, the cancer is c-met positive (expresses high levels of c-met, for example, by immunohistochemistry (IHC)). In some embodiments, the pharmaceutical formulation comprises (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) a polysorbate, wherein the polysorbate concentration is greater than 0.02% w/v.

Provided herein are methods of treating a pathological condition associated with dysregulation of c-met activation in a subject, said method comprising administering to the subject a pharmaceutical formulation described herein (e.g., upon dilution (e.g., a diluted pharmaceutical formulation described herein)) comprising an effective amount of the c-met antibody, whereby said condition is treated. In some embodiments, the pathological condition is cancer. In some embodiments, the cancer is non-small cell lung cancer (NSCLC), glioblastoma, pancreatic cancer, sarcoma, renal cell carcinoma, hepatocellular carcinoma, gastric cancer, colorectal cancer, or breast cancer. In some embodiments, the cancer is stage Mb and/or stage IV cancer. In some embodiments, the cancer is locally advanced or metastatic cancer. In some embodiments, the therapy is second line or third line therapy (e.g., second line or third line NSCLC therapy). Dysregulation of c-met activation (and thus signaling) can result from a number of cellular changes, including, for example, overexpression of HGF (c-met's cognate ligand) and/or c-met itself. In some embodiments, the cancer is EGFR mutant. In some embodiments, the cancer is EGFR wild-type. In some embodiments, the cancer is c-met positive (expresses high levels of c-met, for example, by IHC). In some embodiments, the pharmaceutical formulation comprises (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v.

Also provided herein are methods of inhibiting the growth of a cell that expresses c-met or hepatocyte growth factor, or both, said method comprising contacting said cell with a pharmaceutical formulation described herein (e.g., upon dilution (e.g., a diluted pharmaceutical formulation described herein)) comprising an anti-c-met antibody thereby causing an inhibition of growth of said cell. In some embodiments, the growth of said cell is at least in part dependent upon a growth potentiating effect of c-met or hepatocyte growth factor, or both. In some embodiments, the cell is contacted by HGF expressed by a different cell (e.g., through a paracrine effect). In some embodiments, the pharmaceutical formulation comprises (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v.

Provided herein are also methods for treating or preventing cancer comprising administering a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v (e.g., upon dilution to about any of 0.75, 1, or 1.25 mg/mL (e.g., a diluted pharmaceutical formulation described herein)). In some embodiments, the pharmaceutical formulation comprises (a) an anti-c-met antibody (e.g., onartuzumab), wherein the anti-c-met antibody is present at a concentration of about 60 mg/mL; (b) a histidine acetate buffer at pH 5.4, wherein the histidine acetate buffer is at a concentration of about 10 mM; (c) sucrose, wherein the sucrose is at a concentration of about 120 mM; and (d) polysorbate 20, wherein the polysorbate 20 concentration is about 0.04% w/v. In some embodiments, the cancer is non-small cell lung cancer (NSCLC), glioblastoma, pancreatic cancer, sarcoma, renal cell carcinoma, hepatocellular carcinoma, gastric cancer, colorectal cancer, or breast cancer. In some embodiments, the cancer is stage Mb and/or stage IV cancer. In some embodiments, the cancer is locally advanced or metastatic cancer. In some embodiments, the therapy is second line or third line therapy (e.g., second line or third line NSCLC therapy). In some embodiments, the cancer is EGFR mutant. In some embodiments, the cancer is EGFR wild-type. In some embodiments, the cancer is c-met positive (expresses high levels of c-met, for example, by IHC). In some embodiments, the dose of anti-c-met antibody is about 15 mg/kg. In some embodiments, the dose of anti-c-met antibody is about 15 mg/kg administered day one of a 21 day cycle. In some embodiments, the dose of anti-c-met antibody is about 10 mg/kg. In some embodiments, the dose of anti-c-met antibody is about 10 mg/kg administered on day 1 and 15 of a 28 day cycle.

Methods described herein can be used to affect any suitable pathological state, for example, cells and/or tissues associated with dysregulation of the HGF/c-met signaling pathway. In some embodiments of any of the methods described herein, a cell that is targeted in a method described herein is a cancer cell. For example, a cancer cell can be one selected from the group consisting of a breast cancer cell, a colorectal cancer cell, a lung cancer cell, a papillary carcinoma cell (e.g., of the thyroid gland), a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell and a leukemia cell. In some embodiments, a cell that is targeted in a method described herein is a hyperproliferative and/or hyperplastic cell. In some embodiments, a cell that is targeted in a method described herein is a dysplastic cell. In yet another embodiment, a cell that is targeted in a method described herein is a metastatic cell.

In some embodiments of any of the methods described herein, the method further comprises additional treatment steps. For example, in some embodiments, the method further comprises a step wherein a targeted cell and/or tissue (e.g., a cancer cell) is exposed to radiation treatment or a second therapeutic agent (e.g., chemotherapeutic agent). For example, methods are provided for treating or preventing cancer comprising administering (i) a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v (e.g., upon dilution to about any of 0.75, 1, or 1.25 mg/mL (e.g., a diluted pharmaceutical formulation described herein)) and (ii) a second therapeutic agent. In some embodiments, the second therapeutic agent is an EGFR inhibitor (e.g., erlotinib), VEGF inhibitor (e.g., bevacizumab), taxane (e.g., paclitaxel).

In some embodiments of any of the methods described herein, the method further comprises administering an effective amount of a second therapeutic agent. In some embodiments, the dose of anti-c-met antibody is about 15 mg/kg. In some embodiments, the dose of anti-c-met antibody is about 10 mg/kg.

In some embodiments, the second therapeutic agent is an EGFR inhibitor. In some embodiments, the EGFR inhibitor is erlotinib (N-(3-ethynylphenyl)-6,7-bis(2-methoxyethoxy)-4-quinazolinamine). In some embodiments, the dose of anti-c-met antibody is about 15 mg/kg administered day one of a 21 day cycle. For example, provided are methods of treating cancer (e.g., NSCLC) comprising administering (i) a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v (e.g., upon dilution to about any of 0.75, 1, or 1.25 mg/mL (e.g., a diluted pharmaceutical formulation described herein)), wherein the anti-c-met antibody is administered at a dose of 15 mg/kg every three weeks; and (ii) erlotinib (N-(3-ethynylphenyl)-6,7-bis(2-methoxyethoxy)-4-quinazolinamine), wherein erlotinib is administered at a dose of 150 mg, each day of a three week cycle.

In some embodiments, the second therapeutic agent is a taxane (e.g., paclitaxel). In some embodiments, the cancer is breast cancer. In some embodiments, the breast cancer is an ER-negative, PR-negative, and HER2-negative (ER-, PR-, and HER2-; or triple-negative) metastatic breast cancer. In some embodiments, the dose of anti-c-met antibody is about 10 mg/kg. on day 1 and day 15 of a 28-day cycle. For example, provided are methods for treating cancer (e.g., breast cancer) comprising administering (i) a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v (e.g., upon dilution to about any of 0.75, 1, or 1.25 mg/mL (e.g., a diluted pharmaceutical formulation described herein)), wherein the anti-c-met antibody is administered at a dose of 10 mg/kg on day 1 and day 15 of a 28-day cycle; and (ii) paclitaxel, wherein paclitaxel is administered at a dose of 90 mg/m$^2$ by IV infusion on day 1, day 8, and day 15 of the 28-day cycle. In some embodiments, the method increases survival of the patient, decreases the patient's risk of cancer recurrence and/or to increases the patient's likelihood of survival. In some embodiments, the method further comprises administration of an anti-VEGF antibody (e.g., bevacizumab). For example, provided are methods for treating cancer (e.g., breast cancer) comprising administering (i) a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v (e.g., upon dilution to about any of 0.75, 1, or 1.25 mg/mL (e.g., a diluted pharmaceutical formulation described herein)), wherein the anti-c-met antibody is administered at a dose of 10 mg/kg on day 1 and day 15 of a 28-day cycle; (ii) an anti-VEGF antibody (e.g., bevacizumab), wherein the anti-VEGF antibody is administered at a dose of 10 mg/kg on Day 1 and Day 15 of the 28-day cycle; and (iii) paclitaxel, wherein paclitaxel is administered at a dose of 90 mg/m$^2$ by IV infusion on Day 1, Day 8, and Day 15 of the 28-day cycle.

Pharmaceutical formulation comprising the anti-c-met antibody can be used either alone or in combination with other agents in a therapy. For instance, pharmaceutical formulation comprising the anti-c-met antibody may be co-administered with a second therapeutic agent (e.g., another antibody, chemotherapeutic agent(s) (including cocktails of chemotherapeutic agents), other cytotoxic agent(s), anti-angiogenic agent(s), cytokines, and/or growth inhibitory agent(s)). In some embodiments, the second therapeutic agent is administered concurrently or sequentially. The second therapeutic agent can be administered separately from the pharmaceutical formulation comprising the anti-c-met antibody, but as a part of the same treatment regimen. Where the anti-c-met antibody of the pharmaceutical formulation inhibits tumor growth, it may be particularly desirable to combine it with one or more other therapeutic agent(s) which also inhibits tumor growth. For instance, pharmaceutical formulation comprising the anti-c-met antibody may be combined with an EGFR inhibitor, an anti-VEGF antibody and/or anti-ErbB antibodies in a treatment scheme, e.g. in treating any of the diseases described herein, including colorectal cancer, metastatic breast cancer and kidney cancer.

Such combined therapies noted above encompass combined administration (where two or more agents are included in the same or separate formulations), simultaneously, and separate administration, in which case, administration of the pharmaceutical formulation can occur prior to, and/or following, administration of the additional therapeutic agent and/or adjuvant.

Accordingly, in some embodiments of any of the methods described herein, the method comprises targeting a cell wherein c-met or hepatocyte growth factor, or both, is more abundantly expressed by said cell (e.g., a cancer cell) as compared to a normal cell of the same tissue origin. A c-met-expressing cell can be regulated by HGF from a variety of sources, i.e. in an autocrine or paracrine manner. C-met activation and/or signaling can also occur independent of ligand. Hence, in some embodiments of any of the methods, c-met activation in a targeted cell occurs independent of ligand.

The pharmaceutical formulation comprising the anti-c-met antibody can be administered to a human subject for therapeutic purposes. Moreover, pharmaceutical formulation comprising the anti-c-met antibody can be administered to a non-human mammal expressing an antigen with which the immunoglobulin cross-reacts (e.g., a primate, pig or mouse) for veterinary purposes or as an animal model of human disease.

The pharmaceutical formulation comprising the anti-c-met antibody can be used to treat, inhibit, delay progression of, prevent/delay recurrence of, ameliorate, or prevent diseases, disorders or conditions associated with abnormal expression and/or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In some embodiments of any of the methods, a pharmaceutical formulation comprising an immunoconjugate comprising the anti-c-met antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In some embodiments, the cytotoxic agent targets or interferes with nucleic acid in the target cell.

The pharmaceutical formulation comprising the anti-c-met antibody (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some embodiments, the pharmaceutical formulation is administered intravenously. Dosing can be by any suitable route, e.g. by injections, such as intravenous or subcutaneous injections, depending in part on whether the administration is brief or chronic. Various dosing schedules including, but not limited to, single or multiple administrations over various timepoints, bolus administration, and pulse infusion are contemplated herein.

Pharmaceutical formulation comprising the anti-c-met antibody are dosed and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The pharmaceutical formulation comprising the anti-c-met antibody need not be, but is optionally formulated with one or more agents currently used to prevent or treat the disorder in question. The effective amount of such other agents depends on the amount of antibodies present in the formulation, the type of disorder or treatment, and other factors discussed above. These are generally used in the same dosages and with administration routes as used hereinbefore or about from 1 to 99% of the heretofore employed dosages described herein, or any dosage and by any route that is empirically/clinically determined to be appropriate.

For the prevention or treatment of disease, the appropriate dosage of the anti-c-met antibody in the pharmaceutical formulation (when used alone or in combination with one or more additional therapeutic agents) will depend on the type of disease to be treated, the type of antibody, the severity and course of the disease, whether the anti-c-met antibody in the pharmaceutical formulation is administered for preventive or therapeutic purposes, previous therapy, the patient's clinical history and response to the anti-c-met antibody, and the discretion of the attending physician. The pharmaceutical formulation comprising the anti-c-met antibody is suitably administered to the patient at one time or over a series of treatments. Depending on the type and severity of the disease, about 10 mg/kg, about 15 mg/kg or greater (e.g., 15-20 mg/kg) dosage of the anti-c-met antibody is administered to the patient, whether, for example, by one or more separate administrations, or by continuous infusion. In some embodiments, the dose of anti-c-met antibody is about 15 mg/kg. In some embodiments, the dose of anti-c-met antibody is about 15 mg/kg administered day one of a 21 day cycle. In some embodiments, the dose of anti-c-met antibody is about 10 mg/kg. In some embodiments, the dose of anti-c-met antibody is about 10 mg/kg administered on day 1 and 15 of a 28 day cycle.

Doses may be administered intermittently, e.g. about any of every week, every two weeks, every three weeks, or every four weeks.

For repeated administrations over several days or longer, depending on the condition, the treatment would generally be sustained until a desired suppression of disease symptoms occurs. However, other dosage regimens may be useful. The progress of this therapy is easily monitored by conventional techniques and assays.

VI. ARTICLES OF MANUFACTURE

Article of manufacture comprising the pharmaceutical formulation comprising an anti-c-met antibody described herein for the treatment, prevention and/or diagnosis of the disorders described above is provided. The article of manufacture comprises a container and a label or package insert on or associated with the container. Suitable containers include, for example, bottles, vials, syringes, IV solution bags etc. The containers may be formed from a variety of materials such as glass or plastic. The container holds the pharmaceutical formulation comprising the anti-c-met antibody which is by itself or when combined with another composition effective for treating, preventing and/or diagnosing the condition and may have a sterile access port (for example the container may be an intravenous solution bag or a vial having a stopper pierceable by a hypodermic injection needle). For example, provided herein are articles of manufacture and kits comprising a container with a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v contained therein. In some embodiments, the pharmaceutical formulation comprises (a) an anti-c-met antibody (e.g., onartuzumab), wherein the anti-c-met antibody is present at a concentration of about 60 mg/mL; (b) a histidine acetate buffer at pH 5.4, wherein the histidine acetate buffer is at a concentration of about 10 mM; (c) sucrose, wherein the sucrose is at a concentration of about 120 mM; and (d) a polysorbate, wherein the polysorbate concentration is about 0.04% w/v. The label or package insert indicates that the composition is used for treating the condition of choice, such as cancer. In some embodiments, the cancer is non-small cell lung cancer (NSCLC), glioblastoma, pancreatic cancer, sarcoma, renal cell carcinoma, gastric cancer, colorectal cancer, or breast cancer. In some embodiments, the cancer is stage IIIb and/or stage IV cancer. In some embodiments, the cancer is locally advanced or metastatic cancer. In some embodiments, the therapy is second line or third line therapy (e.g., second line or third line NSCLC therapy). In some embodiments, the cancer is EGFR mutant. In some embodiments, the cancer is EGFR wild-type. In some embodiments, the cancer is c-met positive (expresses high levels of c-met, for example, by immunohistochemistry). In some embodiments, the dose of anti-c-met antibody is about 15 mg/kg. In some embodiments, the dose of anti-c-met antibody is about 15 mg/kg administered day one of a 21 day cycle. In some embodiments, the dose of anti-c-met antibody is about 10 mg/kg. In some embodiments, the dose of anti-c-met antibody is about 10 mg/kg administered on day 1 and 15 of a 28 day cycle.

The article of manufacture in this embodiment may further comprise a package insert indicating that the first and second antibody compositions can be used to treat a particular condition, e.g. cancer. In some embodiments, the cancer is non-small cell lung cancer (NSCLC), glioblastoma, pancreatic cancer, sarcoma, renal cell carcinoma, gastric cancer, colorectal cancer, or breast cancer. In some embodiments, the cancer is stage IIIb and/or stage IV. In some embodiments, the cancer is locally advanced or metastatic cancer. In some embodiments, the therapy is second line or third line therapy (e.g., second line or third line NSCLC therapy). In some embodiments, the cancer is EGFR mutant. In some embodiments, the cancer is EGFR wild-type. In some embodiments, the cancer is c-met positive (expresses high levels of c-met, for example, by immunohistochemistry). In some embodiments, the dose of anti-c-met antibody is about 15 mg/kg. In some embodiments, the dose of anti-c-met antibody is about 15 mg/kg administered day one of a 21 day cycle.

Alternatively, or additionally, in some embodiments of any of the articles of manufacture, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Moreover, the article of manufacture may comprise (a) a first container with a pharmaceutical formulation described herein comprising an anti-c-met antibody contained therein; and (b) a second container with a composition contained therein, wherein the composition comprises a further cytotoxic agent. For example, the article of manufacture may comprise (i) a first container with a pharmaceutical formulation comprising (a) an anti-c-met antibody (e.g., onartuzumab), wherein the anti-c-met antibody is present at a concentration between about 50 mg/mL and about 75 mg/mL; (b) a histidine acetate buffer at pH 5.0-5.4, wherein the histidine acetate buffer is at a concentration between about 1 mM and about 20 mM; (c) sucrose, wherein the sucrose is at a concentration between about 100 mM to about 150 mM; and (d) polysorbate 20, wherein the polysorbate 20 concentration is greater than 0.02% w/v; and (ii) a second container with a composition contained therein, wherein the composition comprises a second therapeutic agent.

In some embodiments, the second therapeutic agent is an EGFR inhibitor. In some embodiments, the EGFR inhibitor is erlotinib (N-(3-ethynylphenyl)-6,7-bis(2-methoxyethoxy)-4-quinazolinamine). In some embodiments, the article of manufacture comprises instructions for administration of about 15 mg/kg administered day one of a 21 day cycle of anti-c-met antibody formulation and 150 mg, each day of a three week cycle of erlotinib. In some embodiments, the article of manufacture comprises instructions for the treatment of cancer (e.g., NSCLC).

In some embodiments, the second therapeutic agent is a taxane (e.g., paclitaxel). In some embodiments, the article of manufacture comprises instructions for administration of about 10 mg/kg. on day 1 and day 15 of a 28-day cycle of the anti-c-met antibody formulation and 90 mg/m$^2$ by IV infusion on day 1, day 8, and day 15 of the 28-day cycle of paclitaxel. In some embodiments, the article of manufacture comprises a third container with a composition contained therein, wherein the composition comprises a third therapeutic agent, wherein the third therapeutic agent is an anti-VEGF antibody (e.g., bevacizumab). In some embodiments, the article of manufacture comprises instructions for administration of about 10 mg/kg. on day 1 and day 15 of a 28-day cycle of the anti-c-met antibody formulation, 90 mg/m$^2$ by IV infusion on day 1, day 8, and day 15 of the 28-day cycle of paclitaxel, and 10 mg/kg on Day 1 and Day 15 of the 28-day cycle of the anti-VEGF antibody (e.g., bevacizumab). In some embodiments, the article of manufacture comprises instructions for the treatment of cancer. In some embodiments, the cancer is breast cancer (e.g., ER-negative, PR-negative, and HER2-negative (ER-, PR-, and HER2-; or triple-negative) metastatic breast cancer). In some embodiments, the method increases survival of the patient, decreases the patient's risk of cancer recurrence and/or to increases the patient's likelihood of survival.

It is understood that any of the above articles of manufacture may include an immunoconjugate of the anti-c-met antibody disclosed herein in place or in addition to the anti-c-met antibody.

Further provided herein are methods of making any of the articles of manufacture described herein.

Exemplary Embodiments

1. A pharmaceutical formulation comprising:
   (a) an anti-c-met antibody;
   (b) a histidine buffer at pH 5.0-5.4;
   (c) a saccharide; and
   (d) a polysorbate, wherein the polysorbate is present at greater than 0.02% w/v.
2. The pharmaceutical formulation of embodiment 1, wherein the anti-c-met antibody comprises a HVR-L1 comprising sequence KSSQSLLYTSSQKNYLA (SEQ ID NO:1), a HVR-L2 comprising sequence WASTRES (SEQ ID NO:2), a HVR-L3 comprising sequence QQYYAYPWT (SEQ ID NO:3), a HVR-H1 comprising sequence GYTFT-SYWLH (SEQ ID NO:4), a HVR-H2 comprising sequence GMIDPSNSDTRFNPNFKD (SEQ ID NO:5), and a HVR-H3 comprising sequence ATYRSYVTPLDY (SEQ ID NO:6).

3. The pharmaceutical formulation of any one of embodiments 1-2, wherein the anti-c-met antibody comprises (a) a heavy chain variable domain comprising the sequence: EVQLVESGGGLVQPGGSLRLSCAASGYTFTSYWLH-WVRQAPGKGLEWVGMIDPSNSDT RFNPNFKDRFTI-SADTSKNTAYLQMNSLRAEDTAVYYCATYRSYVT-PLDYWGQGTLVTV SS (SEQ ID NO:19) and (b) a light chain variable domain comprising the sequence: DIQMTQSPSSLSASVGDRVTITCKSSQSLLYTSSQK-NYLAWYQQKPGKAPKLLIYWASTR ESGVPSRF-SGSGSGTDFTLTISSLQPEDFATYYCQQYYAYPWTF-GQGTKVEIKR (SEQ ID NO:20).

4. The pharmaceutical formulation of any one of embodiments 1-3, wherein the anti-c-met antibody comprises a single antigen binding arm and comprises a Fc region, wherein the Fc region comprises a first and a second Fc polypeptide, and wherein the first and second Fc polypeptides are present in a complex.

5. The pharmaceutical formulation of embodiment 4, wherein the first and second Fc polypeptides form a Fc region that increases stability of said antibody fragment compared to a Fab molecule comprising said antigen binding arm.

6. The pharmaceutical formulation of any one of embodiment 1-5, wherein the anti-c-met antibody comprises (a) a first polypeptide comprising the amino acid sequence of SEQ ID NO:19, a CH1 sequence, and a first Fc polypeptide and (b) a second polypeptide comprising the amino acid sequence of SEQ ID NO:20 and CL1 sequence.

7. The pharmaceutical formulation of embodiment 6, wherein the anti-c-met antibody further comprises (c) a third polypeptide comprising a second Fc polypeptide.

8. The pharmaceutical formulation of any one of embodiments 1-7, wherein the first Fc polypeptide comprises the Fc sequence depicted in FIG. 2 (SEQ ID NO: 17) and the second Fc polypeptide comprises the Fc sequence depicted in FIG. 3 (SEQ ID NO: 18).

9. The pharmaceutical formulation of any one of embodiments 1-8, wherein the anti-c-met antibody is onartuzumab.

10. The pharmaceutical formulation of any one of embodiments 1-8, wherein the anti-c-met antibody binds the same epitope as onartuzumab.

11. The pharmaceutical formulation of any one of embodiments 1-10, wherein the anti-c-met antibody is present at a concentration between about 10 mg/mL and about 100 mg/mL (e.g. about 15 mg/mL and about 75 mg/mL).

12. The pharmaceutical formulation of embodiment 11, wherein the anti-c-met antibody is present at a concentration of about 60 mg/mL.

13. The pharmaceutical formulation of any one of embodiments 1-12, wherein the saccharide is present at a concentration of about 75 mM to about 200 mM (e.g., about 100 mM to about 150 mM).

14. The pharmaceutical formulation of embodiment 13, wherein the saccharide is present at a concentration of about 120 mM.

15. The pharmaceutical formulation of any one of embodiments 1-14, wherein the saccharide is a disaccharide.

16. The pharmaceutical formulation of embodiment 15, wherein the disaccharide is trehalose.

17. The pharmaceutical formulation of embodiment 15, wherein the disaccharide is sucrose.

18. The pharmaceutical formulation of any one of embodiments 1-17, wherein the histidine buffer is at a concentration of about 1 mM to about 50 mM (e.g. about 1 mM to about 25 mM).

19. The pharmaceutical formulation of embodiment 18, wherein the histidine buffer is at a concentration of about 10 mM.

20. The pharmaceutical formulation of any one of embodiments 1-19, wherein the histidine buffer is histidine acetate.

21. The pharmaceutical formulation of any one of embodiments 1-20, wherein the polysorbate is present at a concentration greater than 0.02% and less than about 0.1%.

22. The pharmaceutical formulation of embodiment 21, wherein the polysorbate is present at a concentration of about 0.04%.

23. The pharmaceutical formulation of any one of embodiments 1-22, wherein the polysorbate is polysorbate 20.

24. The pharmaceutical formulation of any one of embodiments 1-23, wherein the formulation is diluted with a diluent (e.g., 0.9% NaCl).

25. The pharmaceutical formulation of embodiment 24, wherein the anti-c-met antibody is present at a concentration of about 1 mg/mL.

26. A method of inhibiting c-met activated cell proliferation, said method comprising contacting a cell or tissue with an effective amount of the pharmaceutical formulation of any one of embodiments 1-25.

27. A method of modulating a disease associated with dysregulation of the HGF/c-met signaling axis, said method comprising administering to a subject an effective amount of the pharmaceutical formulation of any one of embodiments 1-25.

28. A method of treating a subject having a proliferative disorder, said method comprising administering to the subject an effective amount of the pharmaceutical formulation of any one of embodiments 1-25.

29. The method of embodiment 28, wherein the proliferative disorder is cancer.

30. The method of embodiment 29, wherein the cancer is lung cancer (e.g., non-small cell lung cancer (NSCLC)), glioblastoma, pancreatic cancer, sarcoma, renal cell carcinoma, hepatocellular carcinoma, gastric cancer, colorectal cancer, and/or breast cancer.

31. The method of any one of embodiments 26-30, further comprising a second therapeutic agent.

32. A method of making a pharmaceutical formulation of any one of embodiments 1-25.

33. An article of manufacture comprising a container with the pharmaceutical formulation of any one of embodiments 1-25 contained therein.

34. A method of making the article of manufacture of embodiment 33.

The following are examples of the pharmaceutical formulations. It is understood that various other embodiments may be practiced, given the general description provided above.

EXAMPLES

Example 1

Effect of pH and Buffer on Aggregation and Chemical Stability in Liquid Onartuzumab Formulations Initial anti-c-met antibody, onartuzumab, formulations showed increased low molecule weight species (LMWS)

detected by size exclusion chromatography (SEC) when stored at 5° C. over time. Because of the increase in LMWS, a liquid formulation was not initially pursued, and a lyophilized formulation was developed with 20 mg/mL of onartuzumab, 10 mM histidine succinate, 4% trehalose dihydrate, 0.02% polysorbate 20, pH 5.7.

In an effort to develop and determine feasibility of a liquid formulation and increase antibody concentration, pH and excipient screens were performed.

The viscosity and stability of onartuzumab at various concentrations (20-100 mg/mL) was evaluated in different buffers: a) 10 mM histidine-acetate, 0.02% polysorbate 20, and 120 mM trehalose, b) 10 mM histidine-succinate, 0.02% polysorbate 20, and 120 mM trehalose, and c) 200 mM arginine-succinate and 0.02% polysorbate 20. The formulation including arginine succinate had faster aggregate formation at accelerated temperatures (data not shown). The viscosity was acceptable for all formulations evaluated.

The effect of pH on onartuzumab aggregation and chemical stability was evaluated with the following liquid formulations: a) 20 mg/mL of onartuzumab in 10 mM histidine acetate, 120 mM trehalose, 0.02% polysorbate 20, pH 5.2, b) 20 mg/mL of onartuzumab in 10 mM histidine acetate, 120 mM trehalose, 0.02% polysorbate 20, pH 5.7, and c) 20 mg/mL of onartuzumab in 10 mM histidine acetate, 120 mM trehalose, 0.02% polysorbate 20, pH 6.2. Samples were kept at 25° C. or 40° C. over time, and aggregate formulation and chemical stability was evaluated approximately every fifteen days. Aggregate formation was measured using size exclusion chromatography which characterizes changes in size heterogeneity using a TSK G3000 SWXL size-exclusion column.

Figure 1:
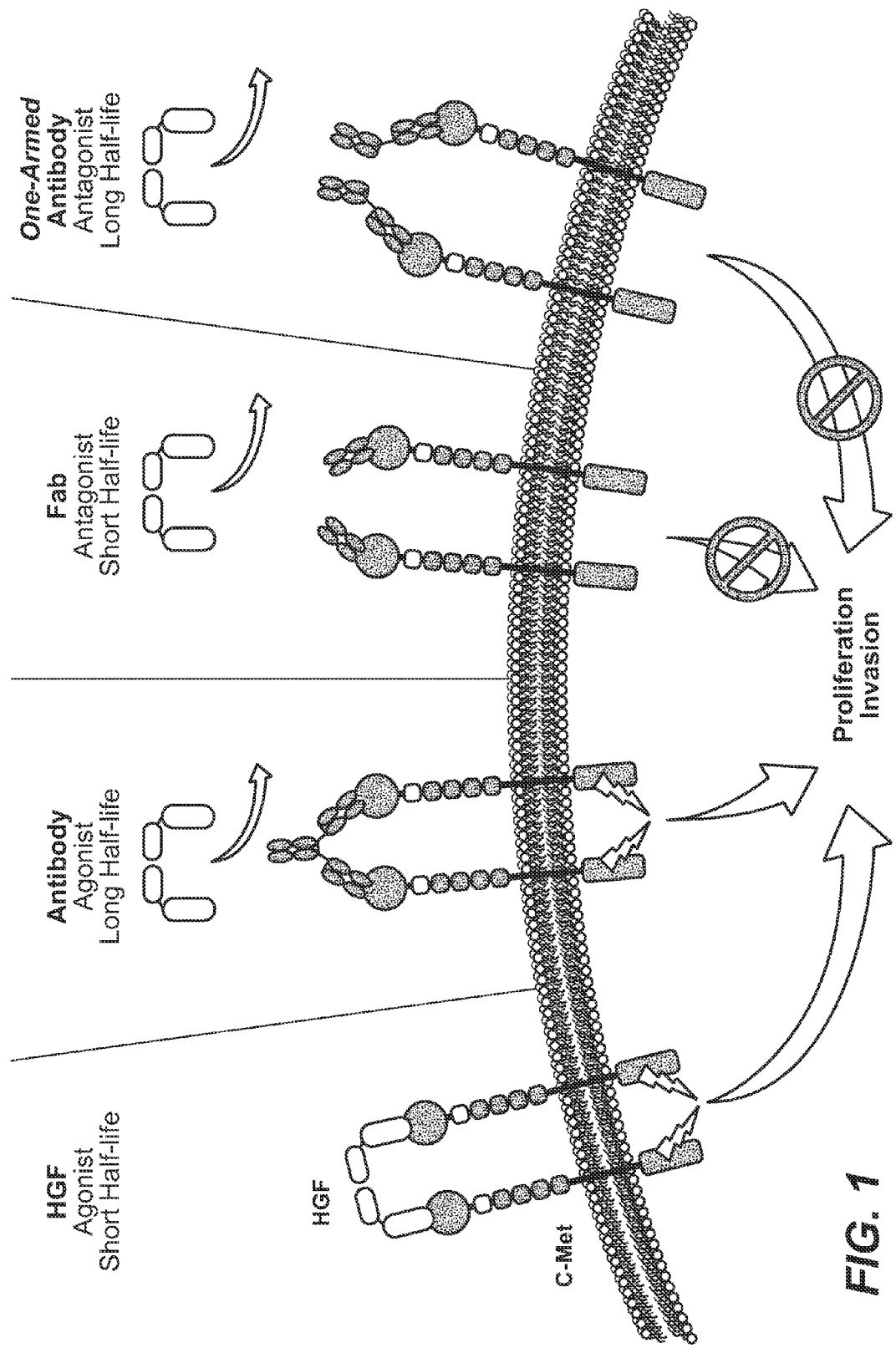
FIG. 1 depicts the general structures of short half-life and long half-life agonists and antagonists of c-Met.
Figure 4:
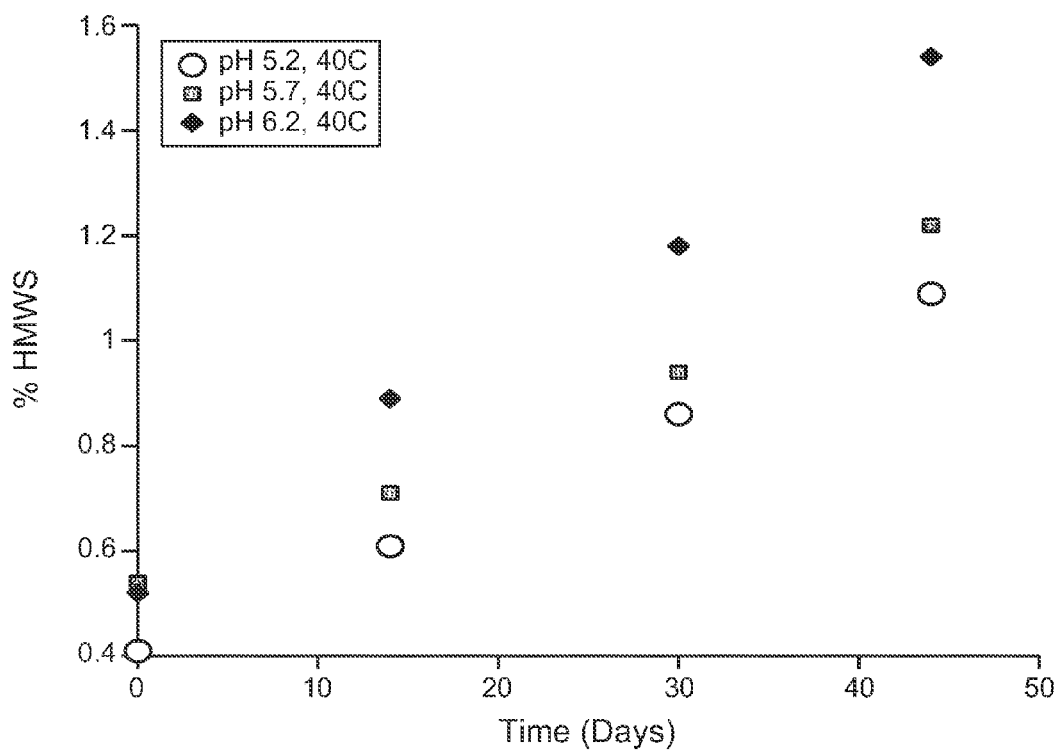
FIG. 4 depicts the rate of aggregate formation as indicated by the percentage of high molecular weight species (HMWS) over time (days) at 40° C. for formulations of 20 mg/mL onartuzumab, 10 mM histidine acetate, 120 mM trehalose, and 0.02% polysorbate 20 at pH 5.2, 5.7, and 6.2.

As shown in FIG. 4, the higher pH of 6.2 resulted in increased aggregate formation as indicated by % of high molecule weight species (HMWS) at 40° C. compared to either pH 5.2 or 5.7. The formulation with a pH 5.2 displayed the lowest aggregate formation as indicated by % HMWS.

Figure 5:
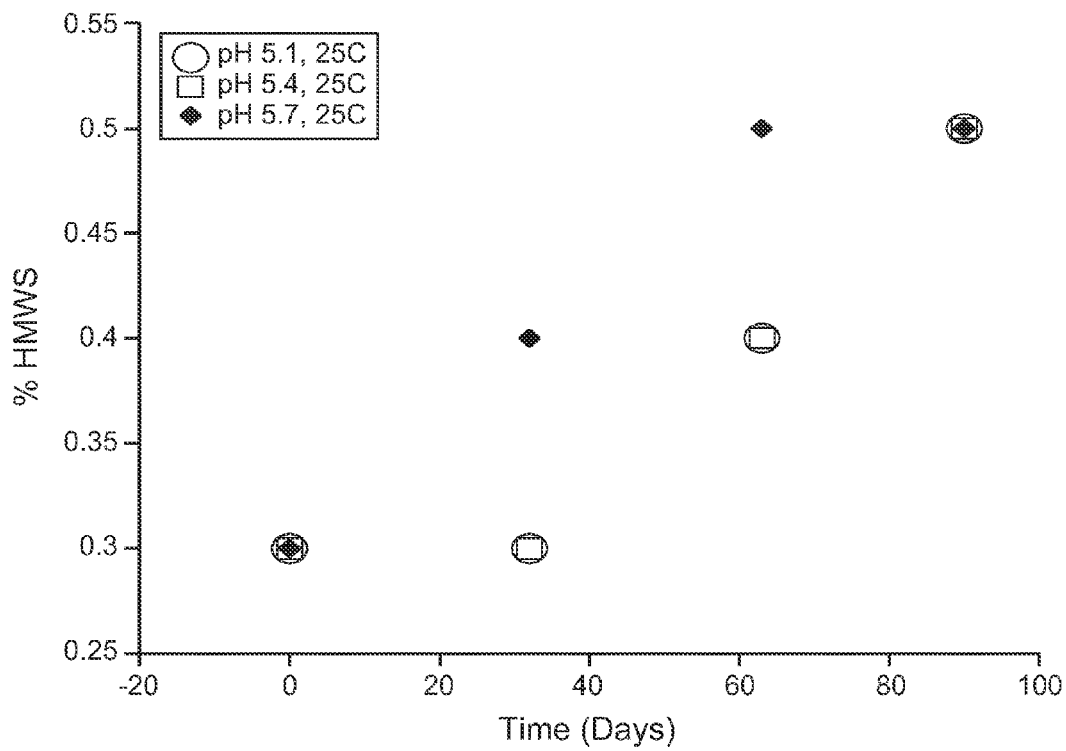
FIG. 5 depicts the rate of aggregate formation as indicated by the percentage of high molecular weight species (HMWS) over time (days) at 25° C. for formulations of 40 mg/mL onartuzumab, 10 mM histidine acetate, 120 mM trehalose, and 0.02% polysorbate 20 at pH 5.1, 5.4, and 5.7.

The effect of pH on onartuzumab aggregation and chemical stability was further evaluated using a higher antibody concentration with the following liquid formulations: a) 40 mg/mL of onartuzumab in 10 mM histidine acetate, 120 mM trehalose, 0.02% polysorbate 20, pH 5.1, b) 40 mg/mL of onartuzumab in 10 mM histidine acetate, 120 mM trehalose, 0.02% polysorbate 20, pH 5.4, and c) 40 mg/mL of onartuzumab in 10 mM histidine acetate, 120 mM trehalose, 0.02% polysorbate 20, pH 5.7. Samples were kept at 25° C. or 40° C. over time, and aggregate formulation and chemical stability was evaluated approximately every four weeks. Aggregate formation was measured as detailed above. As shown in FIGS. 5 and 6, lower pH (e.g., pH 5.4 and 5.1) resulted in decreased aggregate formation as indicated by % HMWS at accelerated temperatures (25° C. and 40° C.) compared to pH 5.7.

Chemical stability was measured using cation exchange chromatography which characterizes changes in charge heterogeneity using a Dionex WCX-10 ion-exchange column (IEC) and elution with a salt gradient.

As shown in FIG. 7, while the lower pH resulted in decreased aggregate formation, there was similar chemical stability as measured by IEC between pH 5.1 and 5.7 at accelerated temperatures at 25° C. and 40° C. Based on these findings, a formulation including histidine buffer (e.g., histidine acetate) and pH 5.4 was utilized for further experimentation.

Example 2

Effect of Polysorbate Concentration on Rate and Extent of Polysorbate Degradation Polysorbate is utilized in polypeptide formulations to minimize adsorption to surfaces and reduce the air-liquid interfacial surface tension and thus the rate of protein denaturation. Loss of polysorbate in a pharmaceutical formulation can result in instability of the formulation. Further, polysorbates can be degraded by oxidation and hydrolysis which can lead to a decrease in the apparent concentration of polysorbate in the pharmaceutical formulation over long shelf life. These polysorbate degradants are less surface-active than nondegraded polysorbate and hence the chemical and physical stability of the pharmaceutical formulation may be compromised. Further, some polysorbate degradants are insoluble and may form particles if they are not solubilized by intact polysorbate, i.e., if the ratio of degraded polysorbate 20:intact polysorbate 20 is too high.

The rate and extent of degradation of polysorbate was evaluated in an onartuzumab formulation including 60 mg/mL of onartuzumab in 10 mM histidine acetate, 120 mM sucrose, 0.02% polysorbate 20, pH 5.4 at 40° C. over time. The concentration of polysorbate 20 was assessed with an assay based on the retention of polysorbate by a mixed-mode ion-exchange column and subsequent elution with a step gradient. Detection was performed using an evaporative light scattering detector (ELSD). The rate of degradation and the ratio of degraded polysorbate 20:intact polysorbate 20 was higher than expected in the onartuzumab formulation at 40° C. over time. The higher than expected rate of degradation and the ratio of degraded polysorbate 20:intact polysorbate 20 could result in instability of the onartuzumab formulation and particulate formation after extended storage.

The percentage of polysorbate 20 was increased in the onartuzumab formulation and the rate and extent of degradation of polysorbate was evaluated in onartuzumab formulations: a) 60 mg/mL of onartuzumab in 10 mM histidine acetate, 120 mM sucrose, 0.02% polysorbate 20, pH 5.4 and b) 60 mg/mL onartuzumab in 10 mM histidine acetate, 120 mM sucrose, 0.04% polysorbate 20, pH 5.4 at 40° C. over time as described above. Surprisingly, as shown in FIG. 8, the increase in polysorbate 20 concentration not only increased the overall levels of polysorbate 20 available to stabilize the onartuzumab formulation, but further decreased the ratio of degraded polysorbate 20:intact polysorbate 20 at 40° C. over time, thereby further increasing the stability of the onartuzumab formulation after extended storage.

Example 3

Effect of Polysorbate Concentration on % High Molecular Weight Species Upon Dilution and Agitation Prior to administration, the onartuzumab formulation is diluted with a diluent (e.g., saline solution) for intravenous infusion. Upon dilution, the polysorbate 20 concentration is significantly reduced, and the stability of the onartuzumab in the formulation could be compromised, for example, by polypeptide aggregation as evidenced by % HMWS, when the diluted onartuzumab formulation (e.g., IV bag and/or IV administration set) is agitated (e.g., during transportation). As previously discussed, aggregation of the monovalent onartuzumab (formation of multimer and oligomers) and/or failure to maintain monovalent structure could lead to an undesirable agonistic effect.

To evaluate the stability of the polypeptide and extent of aggregation upon dilution, onartuzumab formulations, a) 60 mg/mL of onartuzumab in 10 mM histidine acetate, 120 mM trehalose, 0.02% polysorbate 20, pH 5.4 and b) 60 mg/mL onartuzumab in 10 mM histidine acetate, 120 mM sucrose, 0.04% polysorbate 20, pH 5.4, were diluted to 1 mg/mL in IV bags (PVC) with 0.9% NaCl. The bags were agitated (orbital shaker, 100 rpm) at room temperature for formulation (a) and 30° C. for formulation (b).

As shown in FIG. 9, the % HMWS upon agitation was significantly reduced in formulation (b) comprising 0.04% polysorbate 20 compared to formulation (a) comprising 0.02% polysorbate.

PARTIAL REFERENCE LIST

Angeloni, D. et al. (2003). The soluble sema domain of the Ron receptor inhibits MSP-induced receptor activation. J Biol Chem.

Antipenko, A. et al. (2003). Structure of the semaphorin-3A receptor binding module. Neuron 39, 589-598.

Bardelli, A. et al. (1997). Gab1 coupling to the HGF/Met receptor multifunctional docking site requires binding of Grb2 and correlates with the transforming potential. Oncogene 15, 3103-3111.

Bertotti, A., and Comoglio, P. M. (2003). Tyrosine kinase signal specificity: lessons from the HGF receptor. Trends Biochem Sci 28, 527-533.

Bladt, F. et al. (1995). Essential role for the c-met receptor in the migration of myogenic precursor cells into the limb bud. Nature 376, 768-771.

Blechman, J. M. et al. (1995). The fourth immunoglobulin domain of the stem cell factor receptor couples ligand binding to signal transduction. Cell 80, 103-113.

Boix, L. et al. (1994). c-met mRNA overexpression in human hepatocellular carcinoma. Hepatology 19, 88-91.

Bottaro, D. P. et al. (1991). Identification of the hepatocyte growth factor receptor as the c-met proto-oncogene product. Science 251, 802-804.

Bussolino, F. et al. (1992). Hepatocyte growth factor is a potent angiogenic factor which stimulates endothelial cell motility and growth. J Cell Biol 119, 629-641.

Coltella, N. et al. (2003). Role of the MET/HGF receptor in proliferation and invasive behavior of osteosarcoma. Faseb J 17, 1162-1164.

Cooper, C. S. et al. (1984). Molecular cloning of a new transforming gene from a chemically transformed human cell line. Nature 311, 29-33.

Di Renzo, M. F. et al. (1995). Overexpression and amplification of the met/HGF receptor gene during the progression of colorectal cancer. Clin Cancer Res 1, 147-154.

Ferguson, K. M. et al. (2003). EGF activates its receptor by removing interactions that autoinhibit ectodomain dimerization. Mol Cell 11, 507-517.

Furge, K. A. et al. (2000). Met receptor tyrosine kinase: enhanced signaling through adapter proteins. Oncogene 19, 5582-5589.

Garrett, T. P. et al. (2002). Crystal structure of a truncated epidermal growth factor receptor extracellular domain bound to transforming growth factor alpha. Cell 110, 763-773.

Gherardi, E. et al. (2003). Functional map and domain structure of MET, the product of the c-met protooncogene and receptor for hepatocyte growth factor/scatter factor. Proc Natl Acad Sci USA.

Giancotti, F. G., and Ruoslahti, E. (1999). Integrin signaling. Science 285, 1028-1032.

Giordano, S. et al. (2002). The semaphorin 4D receptor controls invasive growth by coupling with Met. Nat Cell Biol 4, 720-724.

Giordano, S. et al. (1989). Biosynthesis of the protein encoded by the c-met proto-oncogene. Oncogene 4, 1383-1388.

Giordano, S. et al. (2000). Different point mutations in the met oncogene elicit distinct biological properties. Faseb J 14, 399-406.

Hamanoue, M. et al. (1996). Neurotrophic effect of hepatocyte growth factor on central nervous system neurons in vitro. J Neurosci Res 43, 554-564.

Hartmann, G. et al. (1994). The motility signal of scatter factor/hepatocyte growth factor mediated through the receptor tyrosine kinase met requires intracellular action of Ras. J Biol Chem 269, 21936-21939.

Jeffers, M. et al. (1996). Enhanced tumorigenicity and invasion-metastasis by hepatocyte growth factor/scatter factor-met signaling in human cells concomitant with induction of the urokinase proteolysis network. Mol Cell Biol 16, 1115-1125.

Jeffers, M., Schmidt et al. (1997). Activating mutations for the met tyrosine kinase receptor in human cancer. Proc Natl Acad Sci USA 94, 11445-11450.

Jin, L. et al. (1997). Expression of scatter factor and c-met receptor in benign and malignant breast tissue. Cancer 79, 749-760.

Kuniyasu, H. et al. (1993). Aberrant expression of c-met mRNA in human gastric carcinomas. Int J Cancer 55, 72-75.

Lev, S., et al. (1992). A recombinant ectodomain of the receptor for the stem cell factor (SCF) retains ligand-induced receptor dimerization and antagonizes SCF-stimulated cellular responses. J Biol Chem 267, 10866-10873.

Liu, C. et al. (1992). Overexpression of c-met proto-oncogene but not epidermal growth factor receptor or c-erbB-2 in primary human colorectal carcinomas. Oncogene 7, 181-185.

Lokker, N. A. et al. (1992). Structure-function analysis of hepatocyte growth factor: identification of variants that lack mitogenic activity yet retain high affinity receptor binding. Embo J 11, 2503-2510.

Lorenzato, A. et al. (2002). Novel somatic mutations of the MET oncogene in human carcinoma metastases activating cell motility and invasion. Cancer Res 62, 7025-7030.

Love, C. A. et al. (2003). The ligand-binding face of the semaphorins revealed by the high-resolution crystal structure of SEMA4D. Nat Struct Biol 10, 843-848.

Maim, F. et al. (1996). Uncoupling of Grb2 from the Met receptor in vivo reveals complex roles in muscle development. Cell 87, 531-542.

Matsumoto, K., and Nakamura, T. (1993). Roles of HGF as a pleiotropic factor in organ regeneration. Exs 65, 225-249.

Maulik, G. et al. (2002). Role of the hepatocyte growth factor receptor, c-Met, in oncogenesis and potential for therapeutic inhibition. Cytokine Growth Factor Rev 13, 41-59.

Meiners, S. et al. (1998). Role of morphogenetic factors in metastasis of mammary carcinoma cells. Oncogene 16, 9-20.

Morello, S. et al. (2001). MET receptor is overexpressed but not mutated in oral squamous cell carcinomas. J Cell Physiol 189, 285-290.

Naka, D. et al. (1992). Activation of hepatocyte growth factor by proteolytic conversion of a single chain form to a heterodimer. J Biol Chem 267, 20114-20119.

Naldini, L. et al. (1991). Scatter factor and hepatocyte growth factor are indistinguishable ligands for the MET receptor. Embo J 10, 2867-2878.

Natali, P. G. et al. (1996). Overexpression of the met/HGF receptor in renal cell carcinomas. Int J Cancer 69, 212-217.

Nguyen, L. et al. (1997). Association of the multisubstrate docking protein Gab1 with the hepatocyte growth factor receptor requires a functional Grb2 binding site involving tyrosine 1356. J Biol Chem 272, 20811-20819.

Nusrat, A. et al. (1994). Hepatocyte growth factor/scatter factor effects on epithelia. Regulation of intercellular junctions in transformed and nontransformed cell lines, basolateral polarization of c-met receptor in transformed and natural intestinal epithelia, and induction of rapid wound repair in a transformed model epithelium. J Clin Invest 93, 2056-2065.

Ogiso, H. et al. (2002). Crystal structure of the complex of human epidermal growth factor and receptor extracellular domains. Cell 110, 775-787.

Olivero, M. et al. (1996). Overexpression and activation of hepatocyte growth factor/scatter factor in human non-small-cell lung carcinomas. Br J Cancer 74, 1862-1868.

Olivero, M. et al. (1999). Novel mutation in the ATP-binding site of the MET oncogene tyrosine kinase in a HPRCC family. Int J Cancer 82, 640-643.

Orian-Rousseau, V. et al. (2002). CD44 is required for two consecutive steps in HGF/c-Met signaling. Genes Dev 16, 3074-3086.

Park, M. et al. (1986). Mechanism of met oncogene activation. Cell 45, 895-904.

Peek, M. et al. (2002). Unusual proteolytic activation of pro-hepatocyte growth factor by plasma kallikrein and coagulation factor XIa. J Biol Chem 277, 47804-47809.

Pelicci, G. et al. (1995). The motogenic and mitogenic responses to HGF are amplified by the Shc adaptor protein. Oncogene 10, 1631-1638.

Plotnikov, A. N. et al. (1999). Structural basis for FGF receptor dimerization and activation. Cell 98, 641-650.

Ponzetto, C. et al. (1994). A multifunctional docking site mediates signaling and transformation by the hepatocyte growth factor/scatter factor receptor family. Cell 77, 261-271.

Ponzetto, C. et al. (1996). Specific uncoupling of GRB2 from the Met receptor. Differential effects on transformation and motility. J Biol Chem 271, 14119-14123.

Robertson, S. C. et al. (2000). RTK mutations and human syndromes when good receptors turn bad. Trends Genet 16, 265-271.

Royal, I., and Park, M. (1995). Hepatocyte growth factor-induced scatter of Madin-Darby canine kidney cells requires phosphatidylinositol 3-kinase. J Biol Chem 270, 27780-27787.

Schmidt, C. et al. (1995). Scatter factor/hepatocyte growth factor is essential for liver development. Nature 373, 699-702.

Schmidt, L. et al. (1997). Germline and somatic mutations in the tyrosine kinase domain of the MET proto-oncogene in papillary renal carcinomas. Nat Genet 16, 68-73.

Schmidt, L. et al. (1999). Novel mutations of the MET proto-oncogene in papillary renal carcinomas. Oncogene 18, 2343-2350.

Suzuki, K. et al. (1994). Expression of the c-met protooncogene in human hepatocellular carcinoma. Hepatology 20, 1231-1236.

Tamagnone, L. et al. (1999). Plexins are a large family of receptors for transmembrane, secreted, and GPI-anchored semaphorins in vertebrates. Cell 99, 71-80.

Tempest, P. R. et al. (1988). Structure of the met protein and variation of met protein kinase activity among human tumour cell lines. Br J Cancer 58, 3-7.

Trusolino, L. et al. (2001). A signaling adapter function for alpha6beta4 integrin in the control of HGF-dependent invasive growth. Cell 107, 643-654.

Uehara, Y. et al. (1995). Placental defect and embryonic lethality in mice lacking hepatocyte growth factor/scatter factor. Nature 373, 702-705.

Van Vactor, D. V., and Lorenz, L. J. (1999). Neural development: The semantics of axon guidance. Curr Biol 9, R201-204.

Weidner, K. M. et al. (1996). Interaction between Gab1 and the c-Met receptor tyrosine kinase is responsible for epithelial morphogenesis. Nature 384, 173-176.

Wiesmann, C. et al. (1997). Crystal structure at 1.7 A resolution of VEGF in complex with domain 2 of the Flt-1 receptor. Cell 91, 695-704.

Wiesmann, C. et al. (1999). Crystal structure of nerve growth factor in complex with the ligand-binding domain of the TrkA receptor. Nature 401, 184-188.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A pharmaceutical formulation comprising:
   (a) an anti-c-met antibody, wherein the anti-c-met antibody is onartuzumab present at a concentration between about 10 mg/mL and about 100 mg/mL;
   (b) a histidine buffer at pH 5.0-5.4;
   (c) a saccharide; and
   (d) polysorbate 20, wherein the polysorbate 20 is present at a concentration of about 0.04% w/v.

2. The pharmaceutical formulation of claim 1, wherein the saccharide is present at a concentration of about 75 mM to about 200 mM.

3. The pharmaceutical formulation of claim 1, wherein the saccharide is a disaccharide.

4. The pharmaceutical formulation of claim 3, wherein the disaccharide is trehalose.

5. The pharmaceutical formulation of claim 3, wherein the disaccharide is sucrose.

6. The pharmaceutical formulation of claim 1, wherein the histidine buffer is at a concentration of about 1 mM to about 50 mM.

7. The pharmaceutical formulation of claim 1, wherein the formulation is diluted with a diluent.

8. A method of treating a subject having a proliferative disorder, said method comprising administering to the subject an effective amount of the pharmaceutical formulation of claim 1.

9. The method of claim 8, wherein the proliferative disorder is cancer.

10. The method of claim 9, wherein the cancer is lung cancer, glioblastoma, pancreatic cancer, sarcoma, renal cell carcinoma, hepatocellular carcinoma, gastric cancer, colorectal cancer, and/or breast cancer.

11. The method of claim 8, further comprising a second therapeutic agent.

12. A method of making a pharmaceutical formulation of claim 1 comprising combining:
(a) the anti-c-met antibody;
(b) the histidine buffer;
(c) the saccharide; and
(d) the polysorbate 20.

13. The pharmaceutical formulation of claim 6, wherein the histidine buffer is at a concentration of about 1 mM to about 20 mM.

14. The pharmaceutical formulation of claim 6, wherein the histidine buffer is at a concentration of about 5 mM to about 15 mM.

15. The pharmaceutical formulation of claim 6, wherein the histidine buffer is at a concentration of about 5 mM.

16. The pharmaceutical formulation of claim 6, wherein the histidine buffer is at a concentration of about 7.5 mM.

17. The pharmaceutical formulation of claim 6, wherein the histidine buffer is at a concentration of about 10 mM.

18. A pharmaceutical formulation comprising:
(a) an anti-c-met antibody, wherein the anti-c-met antibody is present at a concentration of about 60 mg/ml, wherein the anti-c-met antibody is onartuzumab;
(b) a histidine buffer at pH 5.4, wherein the histidine buffer is at a concentration of about 5 mM to about 15 mM, wherein the histidine buffer is histidine acetate;
(c) a saccharide, wherein the saccharide is present at a concentration of about 120 mM, wherein the saccharide is sucrose; and
(d) polysorbate 20, wherein the polysorbate 20 is present at a concentration of about 0.04%.

19. A pharmaceutical formulation comprising:
(a) an anti-c-met antibody, wherein the anti-c-met antibody is present at a concentration of about 60 mg/ml, wherein the anti-c-met antibody is onartuzumab;
(b) a histidine buffer at pH 5.4, wherein the histidine buffer is at a concentration of about 7.5 mM, wherein the histidine buffer is histidine acetate;
(c) a saccharide, wherein the saccharide is present at a concentration of about 120 mM, wherein the saccharide is sucrose; and
(d) polysorbate 20, wherein the polysorbate 20 is present at a concentration of about 0.04%.

20. The pharmaceutical formulation of any one of claim 1, 6, or 13-17, wherein the histidine buffer is histidine acetate.

* * * * *